United States Patent
Liu et al.

(10) Patent No.: US 9,606,125 B2
(45) Date of Patent: *Mar. 28, 2017

(54) METHODS OF DETECTING CONJUGATION SITE-SPECIFIC AND HIDDEN EPITOPE/ANTIGEN

(71) Applicants: Chunli Liu, Baltimore, MD (US); Bingren Hu, Baltimore, MD (US)

(72) Inventors: Chunli Liu, Baltimore, MD (US); Bingren Hu, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 14/658,164

(22) Filed: Mar. 14, 2015

(65) Prior Publication Data

US 2015/0241450 A1  Aug. 27, 2015

Related U.S. Application Data

(63) Continuation of application No. 13/312,285, filed on Dec. 6, 2011, now Pat. No. 9,383,367.

(60) Provisional application No. 61/420,354, filed on Dec. 7, 2010.

(51) Int. Cl.

| | |
|---|---|
| *G01N 33/573* | (2006.01) |
| *G01N 33/68* | (2006.01) |
| *C07K 16/18* | (2006.01) |
| *C12Q 1/34* | (2006.01) |
| *C12Q 1/37* | (2006.01) |
| *C12Q 1/61* | (2006.01) |

(52) U.S. Cl.
CPC .............. *G01N 33/68* (2013.01); *C07K 16/18* (2013.01); *C12Q 1/34* (2013.01); *G01N 33/6878* (2013.01); *C07K 2317/21* (2013.01); *C12Q 1/37* (2013.01); *C12Q 1/61* (2013.01)

(58) Field of Classification Search
CPC .... G01N 33/6878; G01N 33/68; C07K 16/18; C07K 16/44; C12Q 1/34; C12Q 1/61; C12Q 1/37

See application file for complete search history.

(56) References Cited

U.S. PATENT DOCUMENTS 9,383,367 B1 * 7/2016 Liu .................... G01N 33/6878

OTHER PUBLICATIONS

Kirkpatrick et al. Quantitative analysis of in vitro ubiquitinated cyclin B1 reveals compex chain topology. Nature Cell Biol. 2006, vol. 8, No. 7, pp. 700-710 and supporting online material.*
Koivunen et al. Principles of immunochemical techniques used in clinical laboratories. Labmedicine 2006, Vo.37, No. 8, pp. 490-497.*
Wang et al. Analysis of nondegradative protein ubiquitylation with a monoclonal antibody specific for lysine-63-linked polyubiquitin., PNAS 2008, vol. 105, No. 51, pp. 20197-20202.*

* cited by examiner

*Primary Examiner* — Shafiqul Hao

(57) ABSTRACT

This invention discloses "Artificially Cleaved Epitope (ACE)" methods, antibodies, reagents, immunoassays, and kits for designing and detecting hidden epitopes/antigens. The ACE methods can detect epitopes that are either absent or poorly accessible naturally to antibodies, and thus must be specifically and artificially created (free terminals) and/or exposed in samples and sample preparations for antibody detection. The ACE structures include, but are not limited to, macromolecule-to-macromolecule conjugation sites, and any types of linear hidden epitopes. The ACE methods comprise ACE antigen design and ACE antigen detection. The ACE methods, antibodies, reagents, immunoassays, and kits are useful in research and discovery, diagnostic, and therapeutic applications. In another aspect, the ACE methods can artificially and specifically expose hidden antigens while reducing the antibody non-specific bindings in all antibody-based applications.

9 Claims, 28 Drawing Sheets

Figure 1:
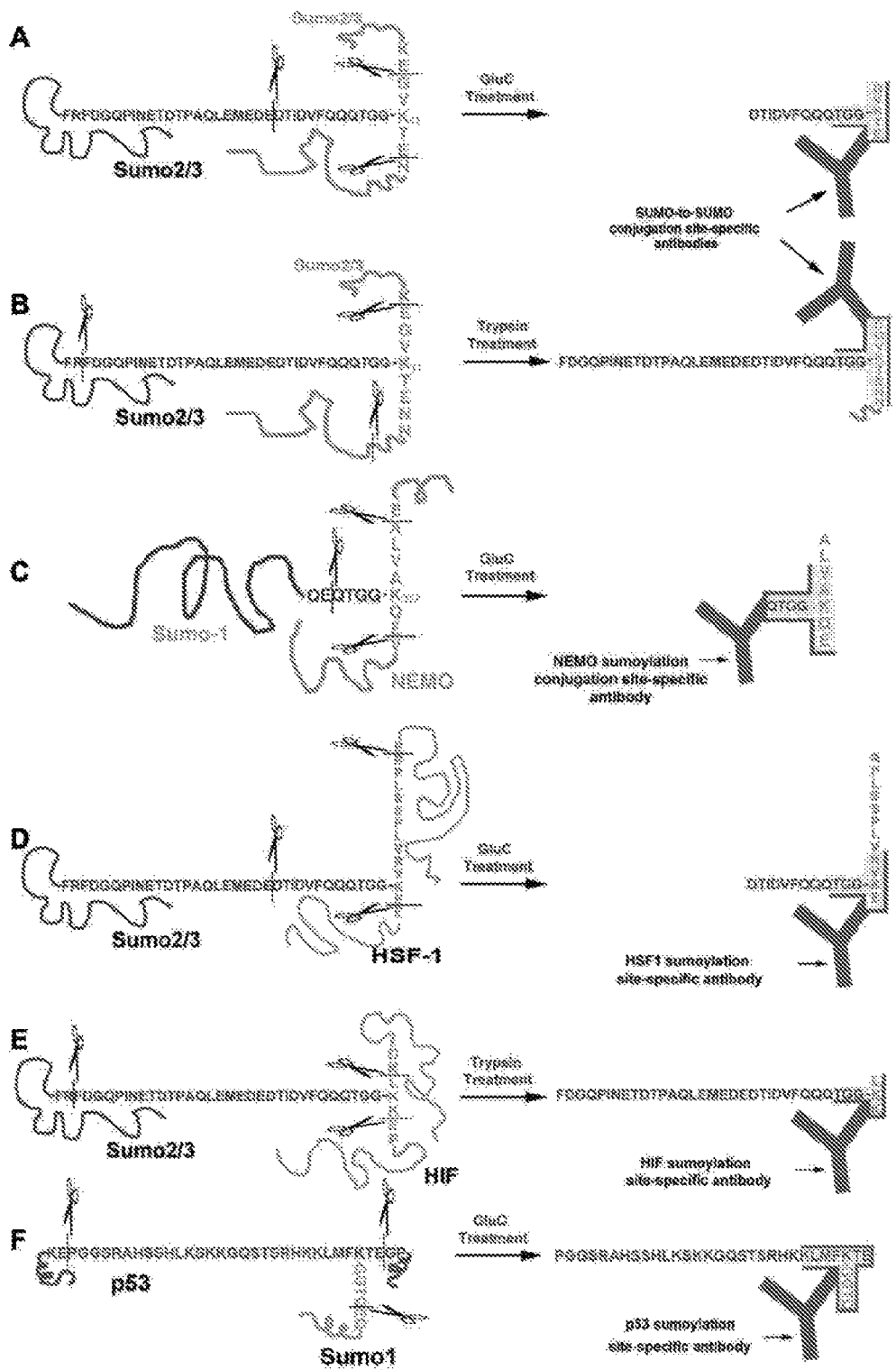

Fig. 1. A-F: Examples of protein sumoylation conjugation site-specific antigens

Figure 2:
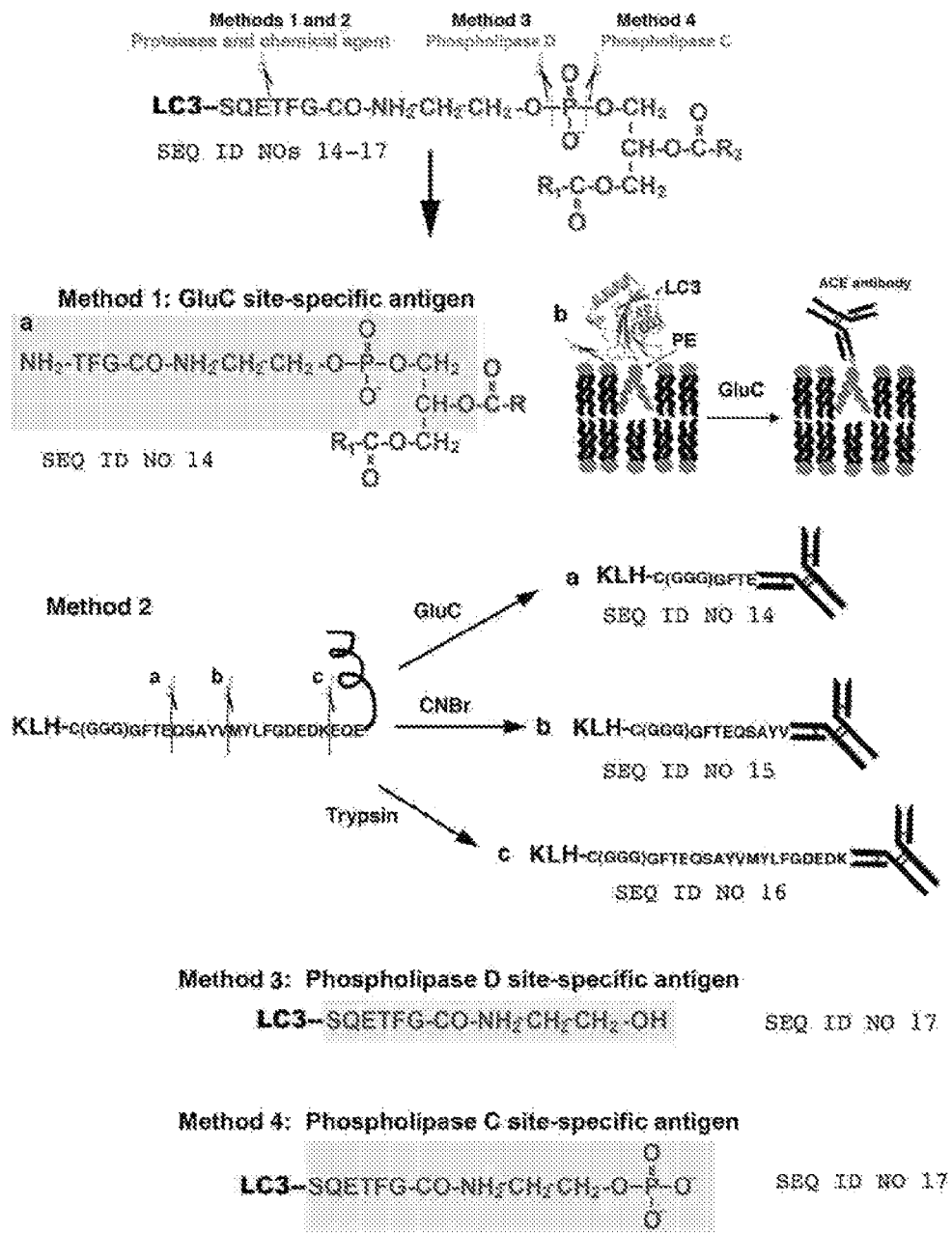

Fig. 2. The ACE Methods

Figure 3:
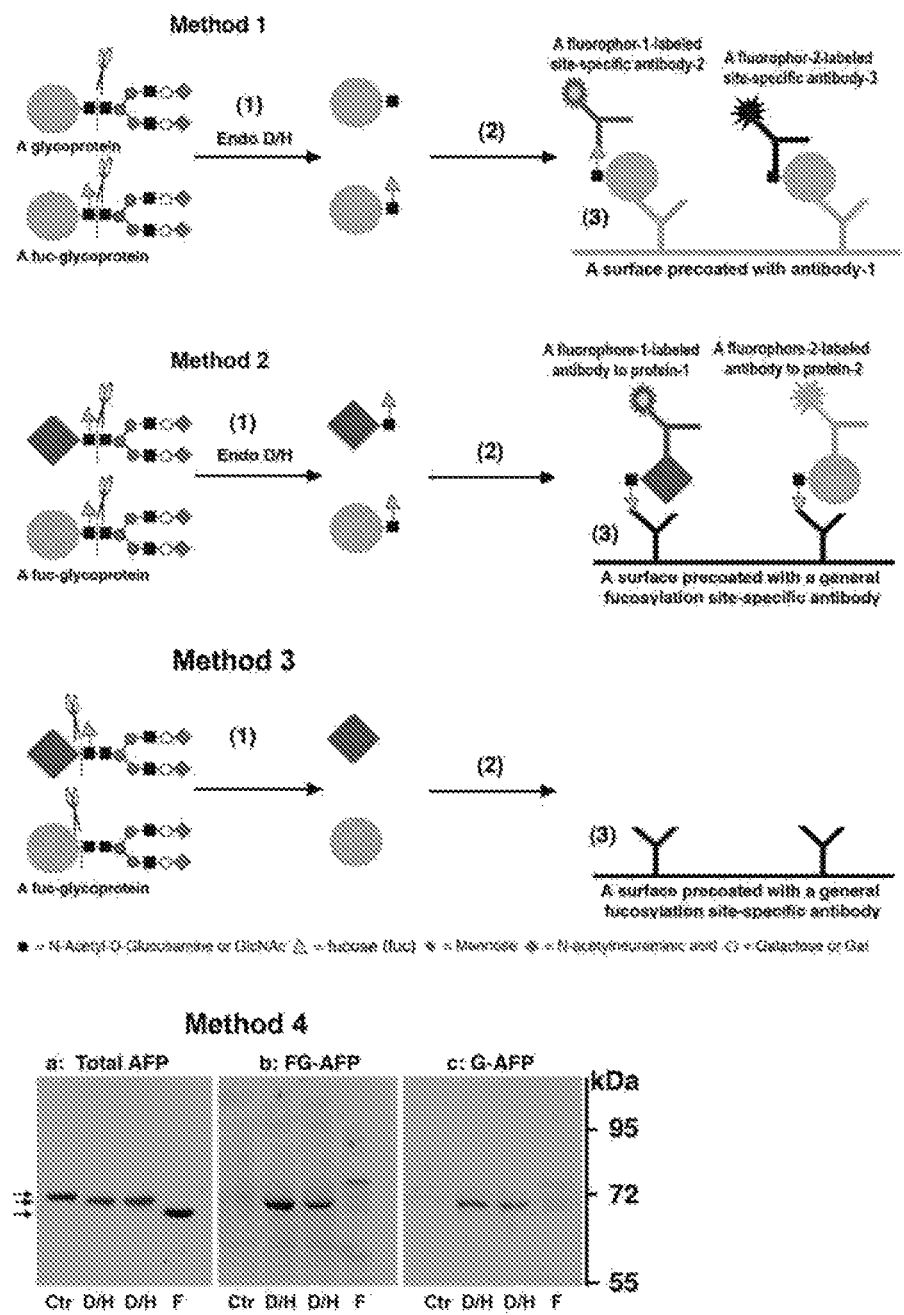

Fig. 3. Glycoform conjugation site-specific immunoassay design and Western blotting Fig. 4. Rationales for the hydrolysis-guided ACE methodology Fig. 6. Examples of making fatty acid-to-protein conjugation site-pseicific antibodies Fig. 7. Two examples of making GPI-to-protein conjugation site-specific antibodies Fig. 8. An example of making a conjugation site-specific antibody to transglutaminase-mediated protein conjugates Fig. 9 Confocal microscopic images Fig. 10. Western blotting of ubiquitin-to-ubiquitin conjugation Fig. 12. Confocal microscopic images Fig. 15. A-B: Examples of Protein Glycosylation Conjugation Site-Specific ACE Structures.

In the following sequences, the ACE structure with branch (GlcNAc or Fuc-alpha1,6-GlcNAc) conjugation is created in a sample preparation by endoglycosidases treatment.

Fig. 15A. Protein Glycosylation Sequence ID NOS: 1 and 18-28

| | SEQ ID NO*: |
|---|---|
| KV*N*(GlcNAc)FTEI | 1 |
| KV*N*(Fucalpha1,6-GlcNAc)FTEI, | 1 |
| NY*N*(GlcNAc)KSD; | 18 |
| NY*N*(Fucalpha1,6-GlcNAc)KSD; | 18 |
| QDQCIY*N*(GlcNAc)TTYLNVQR; | 19 |
| QNQCFY*N*(Fuc-alpha1,6-GlcNAc)SSYLNVQR; | 20 |
| ADTHDEILEG LNF*N*(GlcNAc)LTEIPEAQI; | 21 |
| ADTHDEILEG LNF*N*(Fucalpha1,6-GlcNAc)LTEIPEAQI; | 21 |
| VCQDCPLLAPL*N*(GlcNAc)DTRVVHAAK | 22 |
| VCQDCPLLAPL*N*(Fucalpha1,6-GlcNAc)DTRVVHAAK; | 22 |
| DIVEYYNDS*N*(GlcNAc)GSHVLQGR; | 23 |
| DIVEYYNDS*N*(Fucalpha1,6-GlcNAc)GSHVLQGR; | 23 |
| ADGTVNQI EGEATPV*N*(GlcNAc)LTEPAK; | 24 |
| ADGTVNQI EGEATPV*N*(Fucalpha1,6-GlcNAc)LTEPAK; | 24 |
| IPCSQPPQIEHGTI*N*(GlcNAc)SSR; | 25 |
| IPCSQPPQIEHGTI*N*(Fucalpha1,6-GlcNAc)SSR; | 25 |
| NLFL*N*(GlcNAc)HSE*N*(GlcNAc)ATAKDIAPT; | 26 |
| NLFL*N*(Fucalpha1,6-GlcNAc)HSE*N*(Fucalpha1,6-GlcNAc)ATAKDIAPT | 26 |
| SWPAVG*N*(GlcNAc)CSSALR; | 27 |
| SWPAVG*N*(Fucalpha1,6-GlcNAc)CSSALR; | 27 |
| GLTFQQ*N*(GlcNAc)ASSMCVPDQDT; | 28 |
| GLTFQQ*N*(Fucalpha1,6-GlcNAc)ASSMCVPDQDT; | 28 |

Fig. 15B. Protein Glycosylation Sequence ID NOS: 29-39

| | SEQ ID NO*: |
|---|---|
| HGIQYFN*N*(GlcNAc)NTQHSSLFMLN; | 29 |
| HGIQYFN*N*(Fucalpha1,6-GlcNAc)NTQHSSLFMLN; | 29 |
| LNAEN*N*(GlcNAc)ATFYFK; | 30 |
| LNAEN*N*(Fucalpha1,6-GlcNAc)ATFYFK; | 30 |
| CGLVPVLAENY*N*(GlcNAc)KSDNCEDT; | 31 |
| CGLVPVLAENY*N*(Fucalpha1,6-GlcNAc)KSDNCEDT; | 31 |
| QQQHLFGSN(GlcNAc)VTDCSGNFCL; | 32 |
| QQQHLFGSN(Fucalpha1,6-GlcNAc)VTDCSGNFCL; | 32 |
| EHEGAIYPDN(GlcNAc)TTDFQR; | 33 |
| EHEGAIYPDN(Fucalpha1,6-GlcNAc)TTDFQR; | 33 |
| VVFTAN(GlcNAc)DSGPR; | 34 |
| VVFTAN(Fucalpha1,6-GlcNAc)DSGPR; | 34 |
| YFYN(GlcNAc)GTSMACETFQ; | 35 |
| YFYN(Fucalpha1,6-GlcNAc)GTSMACETFQ; | 35 |
| PFYLTN(GlcNAc)SSGVD; | 36 |
| PFYLTN(Fucalpha1,6-GlcNAc)SSGVD; | 36 |
| AVLVNN(GlcNAc)ITTGER; | 37 |
| AVLVNN(Fucalpha1,6-GlcNAc)ITTGER; | 37 |
| EHVKN(GlcNAc)STYTA; | 38 |
| EHVKN(Fucalpha1,6-GlcNAc)STYTA; | 38 |
| ELTHGASAN(GlcNAc)WTIQY; and | 39 |
| ELTHGASAN(Fucalpha1,6-GlcNAc)WTIQY. | 39 |

*The SEQ ID NO repeats indicate the same peptide sequence with different modification.

No SEQ ID NOs in Fig. 16 are assigned because these are branched peptides

Fig. 16. A-E: Examples of Protein Sumoylation Conjugation Site-Specific ACE Structures. In the following sequences, the branch structure (GGTQ) is derived from any isoform of SUMO proteins.

Fig. 16A. Part A of Branched Sumoylation Conjugation Site-Specific ACE Structures

AHQWFLK(GGTQ)HE;

AIK(GGTQ)SEYPEPYASPPQPGLPYGYPEPFSGGPNVPELILQLLQLEPDEDQVR;

ALVAK(GGTQ)QE;

APPNVK(GGTQ)NEGPLNVVK(GGTQGGGC)TEK;

CFEAHQWFLK(GGTQ)HEAR;

CGGGALVAK(GGTQ)QE;

CLPPKK(GGTQ)RE;

CNGKRKRSQYQRFTYLPANVPIIK(GGTQ)TE;

CPEALFQPSFLGMESCGIHETTFNSIMK(GGTQ)CDVDIR;

CQPPPPCPSQTGSPPVGLIK(GGTQ)GE;

CSGLSTQNHANHNHRIRTNPAIVK(GGTQ)TE;

DELK(GGTQ)SEPGSNCDNSELPGTLHNSHK;

DFARLRLKGMK(GGTQ)DDDYDDQLC;

DGSPNLAPIPVTVK(GGTQ)RE;

DSK(GGTQ)PGIWRD;

DVK(GGTQ)E;

DVLALPIFK(GGTQ)QEEPQLSPEN;

EDEELVKGQKLIK(GGTQ)KEFIETGK;

EGMFLPK(GGTQ)PEAGSAISDVFEGR;

EGVK(GGTQ)TENNDHINLK;

EGVK(GGTQ)TENN;

EHYNQHNSGSYLRDVLALPIFK(GGTQ)QE;

EMADTVIPQK(GGTQ)EEAAICGQMDLSHPPPR;

EPDK(GGTQ)K;

EGK(GGTQ)KEVESK;

GPLGDFGAPALPMAVPGAHGPLAGYLYPAFPGRAIK(GGTQ)SE;

EQCLAGKAHSTGEQPPQLSLATRVK(GGTQ)HE;

No SEQ ID NOs in Fig. 16 are assigned because these are branched peptides

Fig. 16B. Part B of Branched Sumoylation Conjugation Site-Specific ACE Structures

EQPLPAQDPVSV*K(GGTQ)*EEPEAEVR;

ERVITL*K(GGTQ)*ME;

EVPPTETVPQV*K(GGTQ)*KEK;

FEV*K(GGTQ)*K;

FEV*K(GGTQ)*KEPPEAER;

FGV*K(GGTQ)*TEQEDVLAK;

FIVSV*K(GGTQ)*E;

FTYLPANVPII*K(GGTQ)*TEPTDDYEPAPTCGPVSQGLSPLPR;

G*K(GGTQ)*KE;

GLSHTPTV*K*(GGTQ)HLE;

GLSLSLI*K(GGTQ)*SE;

GMFLP*K(GGTQ)*PE;

GM*K(GGTQ)*DDDYDDQLC;

GV*K*(GGTQ)TE;

LLNEPGVQPTSVYGDFSC*K275(GGTQ)*EEPEIDSPGGDIGLSLQR

HPYLPINSAAI*K*(GGTQ)AECTAR;

ENDHPEFIVSV*K302(GGTQ)*EEPVEDDLVPELGISNLLSSSHCPK;

II*K*(GGTQ)QEPVLENCSQDLLQHHA;

I*K(GGTQ)*EEEEGAEASAR;

I*K(GGTQ)*K;

I*K*(GGTQ)ADPDGPEAQAEACSGER;

I*K*(GGTQ)ME;

IKNSL*K(GGTQ)*IDNLDVNRCIE;

ILMGL*K*(GGTQ)SE;

ILRPWHAARHPYLPINSAAI*K*(GGTQ)AE;

IMTPSV*K(GGTQ)*VEK;

K*K(GGTQ)*R;

KKAKKAKIKV*K*(GGTQ)VE;

KKKRPMSQISGVKKLMHSSSLTNSSIPRFGV*K(GGTQ)*TE;

KLM*K(GGTQ)*AFE;

No SEQ ID NOs in Fig. 16 are assigned because these are branched peptides

Fig. 16C. Part C of Branched Sumoylation Conjugation Site-Specific ACE Structures

KLQLRGNTRPMHPIQQSRVPHGRIMTPSV*K(GGTQ)*VE;

KTKAPPNV*K(GGTQ)*NE

KV*K*(GGTQ)EEEEEEK;

LI*K(GGTQ)*TENPAEK;

L*K*(GGTQ)K;

L*K(GGTQ)*SE;

LLPEVHEDGSPNLAPIPVTV*K(GGTQ)*R;

LLVHMGLL*K*(GGTQ)SEDK;

LVHMGLL*K*(GGTQ)SEDK;

LMF*K*(GGQT)TEGPDGGGC;

LM*K(GGTQ)*AFESLK;

LP*K(GGTQ)*FE;

LVKGQKLI*K(GGTQ)*KE;

MADTVIPQ*K(GGTQ)*E;

MSDQDHSMDEMTAVV*K(GGTQ)*IEK;

MSSQVVGIEPLYI*K(GGTQ)*AEPASPDSPK;

MTKI*K*(GGTQ)ADPDGPE;

NGENMG*K(GGTQ)*K;

NLAFHSPTTRI*K(GGTQ)*KE;

NMG*K*(GGTQ)KDKVQDNHLSPNKWKWTKRTLSE;

NPYTYHHQFNLNGLAGTGAYSP*K*(GGTQ)SE;

NPYTYHHQFNLNGLAGTGAYSP*K*(GGTQ)SEYTYGASYR;

NSL*K(GGTQ)*IDNLDVNR;

NTNTLFSV*K(GGTQ)*LEEELSVEGNTDINTDLK;

NTTI*K(GGTQ)*EESK;

PCTVTPGAV*K(GGTQ)*LE;

PCVTHI*K(GGTQ)*TE;

PD*K(GGTQ)*KE;

PGAKTSSRNDYIHSGLYSSFTLNSLNSSNVKLFKLI*K(GGTQ)*TE;

PGGSRAHSSHLKSKKGQSTSRHKKLMF*K*(GGTQ)TE;

No SEQ ID NOs in Fig. 16 are assigned because these are branched peptides

Fig. 16D. Part D of Branched Sumoylation Conjugation Site-Specific ACE Structures

PGPQAPSRTPSPRSPAPARV*K(GGTQ)*AE;

PGVQPTSVYGDFSC*K(GGTQ)*E;

PKDDAYPLYSDFQPPALKI*K(GGTQ)*E;

PLAQNGGSSEPPAAPRSI*K(GGTQ)*VE;

PLEVNAI*K(GGTQ)*KEAGTK;

PLVLEIPSETESQANVVV*K281(GGTQ)*IEEAPLSPSENDHPEFIVS;

PLYI*K(GGTQ)*AE;

PNGEV*K(GGTQ)*SELCESLETNSK;

PPLHV*K(GGTQ)*SE;

PSTGLCSPDLVNRII*K*(GGTQ)QE;

PSV*K(GGTQ)*VEDK;

QPLPAQDPVSV*K(GGTQ)*E;

RHPGVAEV*K(GGTQ)*TEMMQVDEVPSQDSPGAAESSISGGMGDK;

GLPVKTDITPGPSRLCSGARRSFFCRMKCNRPSV*K(GGTQ)*VE;

RV*K(GGTQ)*RE;

RV*K*(GGTQ)E;

SEEAQDMGPGPPDPTEPPLHV*K(GGTQ)*SEDQPGEEEDDER;

SI*K(GGTQ)*VEAVEEPEAAPILGPGEPGPQAPSR;

SIMRDKMPKKGGRWWFSWRGRNTTI*K(GGTQ)*E;

SPEPCTVTPGAV*K(GGTQ)*LEK;

SQANVVV*K(GGTQ)*IE;

SSKPQSKRSLR*K*(GGTQ)VDVE;

SSKPQSKRSLR*K*(GGTQ)VDVE;

SVQDKNTNTLFSV*K(GGTQ)*LE;

SYWSQTILEILMGL*K(GGTQ)*SESGER;

TGRTV*K(GGTQ)*E;

TGRTV*K(GGTQ)*E;

TKMSSHHLSHHPCSPAHPPSTAEGLSLSLI*K(GGTQ)*SECG;

TNPAIV*K(GGTQ)*TE NSWSNK;

TFNSIM*K(GGTQ)*CDVDIRKDLYANTVLSGGTTMYPGIADRMQKE;

No SEQ ID NOs in Fig. 16 are assigned because these are branched peptides

Fig. 16E. Part E of Branched Sumoylation Conjugation Site-Specific ACE Structures

TV*K(GGTQ)*EPEGPPPSPGK;

VITL*K(GGTQ)*MEIPGSMPPLIQEMLENSEGLDTLSGQPGGGGR;

V*K(GGTQ)*HESSSSDEERAAAK

V*K(GGTQ)*KE;

V*K(GGTQ)*R;

V*K(GGTQ)*TE;

V*K*(GGTQ)SELCE;

V*K*(GGTQ)AE;

V*K(GGTQ)*AELSSPTPGSSPVPGELGLAGALFLPQYVFGPD;

V*K(GGTQC)*KE;

VNAI*K(GGTQ)*KE;

VPPTETVPQV*K(GGTQ)*KE;

VVSKIAQY*K*(GGTQ)RE;

WDLSELP*K(GGTQ)*FEK;

WEDV*K(GGTQ)*EEMTSALATMR;

WNLDELP*K(GGTQ)*FEK;

ILSSQSLIQTI*K(GGTQ)*NDIVGLK;

TKVDRILSSQSLIQTI*K(GGTQ)*NDIVGLKAGMATLE;

TVEGAGSIAAATGFV*K(GGTQ)*K;

DQLG*K(GGTQ)*NEEGAP;

EGAGSIAAATGFV*K(GGTQ)*KDQLG*K(GGTQ)*NE;

PV*K(GGTQ)*E;

SEPV*K(GGTQ)*EESSELEQPFAQDTSSVGPD;

CQL*K(GGTQ)*GEATHGQVDCSPGIWQLDCTHLEG;

IVASCDKCQL*K(GGTQ)*GE;

AACWWAGI*K(GGTQ)*QEFGIPYNPQSQGVVESMN;

TAYFILKLAGRWPVRVIHTDNGSNFTSNAVKAACWWAGI*K(GGTQ)*QE;

LLW*K(GGTQ)*GEGAVVIQDNSDIK;

ELQKQITKIQNFRVYYRDSRDPIWKGPAKLLW*K(GGTQ)*GE; and

ALVA*K(GGTQ)*QE.

No SEQ ID NOs in Fig. 17 are assigned because these are branched peptides

Fig. 17. A-D: Examples of Ubiquitination Conjugation Site-Specific ACE structures.
In the following sequences, the ACE structure with branch (GG) conjugation is created in a sample preparation.

Fig. 17A. Part A of the Conjugation Site-Specific ACE structures
AAGTSGLIL*K(GG)*R;
A*K*(GG)EGVVAAAEK;
A*K(GGRLRLVLHLTS)KSK*TAAKKNDKE;
ALIHRDL*K*(GG)PPNLLLVAGGTVLK;
ANQMV*K(GG)*CDPR;
AVYQLTRMCTIRMSFV*K(GGRLRLVLHLTS)*GWGAE;
DAVVISCA*K(GG)*DGVK;
DD*K*(GG)VNFHFILFNNVDGHLYELDGR;
DGFTEDS*K*(GG)PGIWR;
DL*K*(GG)PENLLLASK;
DL*K(GG)*PQNLLINR;
DL*K*(GG)PQNLLINR;
DLSHIGDAVVISCA*K(GG)*DGVK;
DLSHIGDAVVISCA*K(GG)*DGVK;
EEAEQH*K*(GG)IVMETVPVLKAQADIYK;
EGVVAAAE*K*(GG)TK;
ELAKHAV*S(O-GLCNAC)*EGTKAVT*K(GG)*YTSSK;
EQRLIH*K(GGRLRLVLHLTS)*IIDLGYAKE;
ERLLK*K(GGRLRLVLHLST)*KYE;
FARICRDLSHIGDAVVISCA*K(GGRLRLVLHLTS)*DGVKFSASGE;
FDDHWVFWIGPLVGAILGSLLYNYVLFPPA*K(GG)*SLSER;
GIHTLLQNLA*K(GG)*ASPVYLDILG (This is the C-terminal of the protein);
GIYAYGFE*K(GG)*PSAIQQR;
G*K(GGRLRLVLHLST)*GSGLQGHIIE;
G*K(GGRLRLVLHLTS)*LHMATALQIAQLTLKHRQNKVQHQRIVAFVCSPISDSRDE;
GLS*K*(GG)AK;
GLS*K*(GG)A*K(GG)*EGVVAAAE*K(GG)*T*K(GG)*QGVAEAAGK;
GTLAYLPEEYI*K*(GG)TGR;
HAV*S(O-GLCNAC)*EGTKAVT*K(GG)*YTSSK;

No SEQ ID NOs in Fig. 17 are assigned because these are branched peptides

Fig. 17B. Part B of the Conjugation Site-Specific ACE structures

HDSATSFVDAGNAY*K(GG)*K;

HLS*K*(GG)MQQNGYENP;

HV*K*(GG)GILLYGPPGCGK;

HVPGGGSVQIVY*K(GG)*PVDLSK;

ICLDIL*K(GG)*DK;

IDIL*K*(GG)DKWSPALQIR;

IEEELGS*K*(GG)AK;

CIHIGE*K(GG)*VDPVIEQASK

ILAGLHDTQIEG*K(GG)*LHMATALQIAQLTLK;

IMELH*K(GG)*TYR;

*K(GG)*AMFANQLDAR;

*K*(GG)GNFFMGGSDGGYTIW;

*K(GG)K(GG)*GQSTSR;

*K*(GG)QIEELQQEAR;

*K(GG)*QLSSTVFK;

*K(GG)*TSATVGPK;

*K(GGRLRLVLHLTS)*T*K(GGRLRLVLHLTS)*QGVAE;

K*K*(GG)GQSTR;

K*K*(GG)TESHHK;

KLM*K(GGRLRLVLHLTS)*AFE;

KLPNS*K(GG)*QSPDEPLR;

LA*K*(GG)NYGMTR;

LDIL*K(GG)*DK;

LD*K*(GG)AQIHDLVLVGGSTR;

LFHPEQLITG*K*(GG)EDAANNYAR;

LIFAG*K*(GG)QLEDGR;

LIH*K(GG)*IIDLGYAK;

L*K(GG)*EEAEQHK;

LK*K*(GG)EEAEQHK;

LLCLRRSSL*K(GGRLRLVLHLTS)*AYGNGYSSNGNTGE

LL*K*(GG)HPNIVR;

LLVQNIL*K(GG)*R;

LMF*K(GG)*TEGPD (This is the C-terminal of the protein);

No SEQ ID NOs in Fig. 17 are assigned because these are branched peptides

Fig. 17C. Part C of the Conjugation Site-Specific ACE structures

LQTAPVPMPDL*K*(GG)NVK;

LS*K(GG)*AK;

LTP*K*(GG)LGDFGLAR;

LVSHFVEEF*K*(GG)R;

MAMRELVEAECGGANPLM*K(GG)*LAGHFTQDK;

MATLE*K*(GG)LMK;

MATLE*K*(GG)LMK;

MDVFMKGLS*KAK(GGRLRLVLHLTS)*E;

M*K(GG)*K;

MLTINPS*K*(GG)R;

MQL*K*(GG)PMEINPEMLNK;

S*K(GGRLRLVLHLTS)*K;

MSFV*K(GG)*GWGAEYR;

MVNEF*K*(GG)ELVEK;

NGNTGEQSGYHVEQE*K(GG)*EN*K(GG)*LLCEDLPGTEDFVGHQGTVPSDNIDSQGR;

NIFLGE*K*(GG)AAK;

N*K(GGRLRLVLHLST)*LLCE

PAVLAPEDGLAMSLHFMTLGGSSLSPTEG*K(GG)*GSGLQGHIIENPQYFSDACVHHI

PAVVTGKFDDHWVFWIGPLVGAILGSLLYNYVLFPPA*K(GGRLRLVLHLTS)*SLSE

QAQDLARSYGIPFIETSA*K(GG)*TRQRVEDAFYTLVR

QIEEL*K*(GG)GQEVSPK;

QNGYENPTY*K*(GG)FFEQMQN (This is the C-terminal of the protein);

QPAPFSDEIEVDFS*K(GG)*PYVR;

QSGYHVEQE*K(GGRLRLVLHLST)*E;

QSVELHSPQSLPRGT*K*(GG)A (This is the C-terminal of the protein);

SFICNY*K*(GG)EHWFTVR;

SFLQPHSSNPQVVSAVSHQG*K*(GG)R;

SGENFD*K*(GG)FFTR;

SGGSGGGGGGGL*K(GG)*PSITK;

S*K*(GG)K;

S*K(GG)K(GG)*NSLALSLTADQMVSALLDAEPPILYSEYDPT;

SLG*K*(GG)GSAPPGPVPEGQIR;

SPF*K*(GG)CDACLR;

No SEQ ID NOs in Fig. 17 are assigned because these are branched peptides

Fig. 17D. Part D of the Conjugation Site-Specific ACE structures

SPNTAILI*K*(GG)DEAR;
SPPEEPPDFCCP*K*(GG)CQYQAPD;
SQNL*K((GG)*ECFR;
SSHIQDDMHLVIR*K(GGRLRLVLHLST)*QLSSTVFKYKLIGIIGAVTMAGIMAADRSE;
SSHL*K(GG)*SK;
SVDYCRR*K(GG)*IDRMKLQFSLGSIGGLSLHIKI;
SVHSLISDF*K*(GG)DPPTAK;
TAEGLSHTPTV*K*(GG)HLEALR;
TEPEA*K(GG)K*
TEPEA*K(GG)K(GG)SK(GG)*TAAK;
TIPVQAFEV*K(GG)*LDVTLGDLTK;
T*K(GG)*EGVLYVGS*K(GG)*TK;
TQNF*K*(GG)PAPATNTQNYATYR;
TSA*K(GGRLRLVLHLTS)*TRQRVE;
TTIAQQV*K(GG)*GK;
VDFS*K(GGRLRLVLHLTS)*PYVRVTME;
VIDKL*K(GGRLRLVLHLTS)*E;
V*K(GGRLRLVLHLST)*LDVTLGDLTKIGKSQKFTLSVDVEGKFTLSVDVE;
V*K(GGRLRLVLHLTS)*LDVTLGDLTKIGKSQKFTLSVDVE;
VQS*K*(GG)ISGSLDNITHVPGGGNK;
VSADAY*K*(GG)IIPGSR;
VYGTI*K*(GG)PAFNQNPVAK;
WLL*K*(GG)QGELQQM;
YGWHPATVC*K(GG)*IPPGCNLK;
Y*K(GGRLRLVLHLST)*VDPVIE, and
YTRPTPVQ*K*(GG)HAIPIIK.

No SEQ ID NOs are assigned because these are branched peptides

Fig. 18. Examples of Protein Neddylation Conjugation Site-Specific ACE Structures.

LIEFCY*K(GG)*SRSES*K(GG)*RM*K(GG)*GFCLIPQQSINGR

NGRVVSHDFP*K(GGRLRLVLHLTS)*SMQSIPCMSHSSGMPLGATGL (In this case, there is no E residue between the conjugation site and the protein C-terminal)

DRKLLIQAAIVRIM*K(GGRLRLVLHLTS)*MRKVLKHQQLLGE

IM*K(GG)*MR

Fig. 19. Examples of Linear Hidden ACE Structures.

| | SEQ ID NO: |
|---|---|
| *IVIV*MSK; | 40 |
| PADLPPAAALPQPE*VILL*DSDLDEPIDLR; | 41 |
| *VILL*DSDLDE; | 42 |
| *VEVI*DLTIDSSSDEEEEPSAK; | 43 |
| HQVASHHQSSNKNKK*VEVI*DLTIDSSSDE; | 44 |
| *VVVI*SSSEDSDAENSVSSSPQSEVLYWK; | 45 |
| R*VVVI*SSSE; | 46 |
| PEDSPSDDD*VLIV*YELTPTAEQK; | 47 |
| DSPSDDD*VLIV*YE; | 48 |
| YISVGSQADTN*VIDL*TGDDK; | 49 |
| TTYYQTALPGNDRYISVGSQADTN*VIDL*TGDDKDDLQRAIALSLAE; | 50 |
| EATSTPEISLEAEPIELVETAGDEIVDLTCESLEPVVVDLTHNDS*VVIV*DER; and | 51 |
| PVVVDLTHNDS*VVIV*DE. | 52 |
| EGVPQPSGPPARC | 53 |

SEQUENCE LISTING

```
<160> NUMBER OF SEQ ID NOS: 52

<210> SEQ ID NO 1
<211> LENGTH: 11
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide KVNFTEI is a segment of P02771
      (FETA_HUMAN), wherein residue-7 N is covalently conjugated to
      N-acetyl-D-glucosamine (GlcNAc) or alpha-1,6-fucosylated GlcNAc.
      The glycopeptides are made artificially or extracted after
      artifacial cleavage.
<300> PUBLICATION INFORMATION:
<308> DATABASE ACCESSION NUMBER: P02771
<309> DATABASE ENTRY DATE: 2012-03-29
<313> RELEVANT RESIDUES IN SEQ ID NO: (249)..(255)

<400> SEQUENCE: 1

Cys Gly Gly Gly Lys Val Asn Phe Thr Glu Ile
1               5                   10

<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide CPEYPTRR is a segment of P2RX7_HUMAN,
      wherein residue-7 R is modified via ADP-ribosylarginine.
<300> PUBLICATION INFORMATION:
<308> DATABASE ACCESSION NUMBER: Q99572
<309> DATABASE ENTRY DATE: 2012-03-29
<313> RELEVANT RESIDUES IN SEQ ID NO: (119)..(126)

<400> SEQUENCE: 2

Cys Pro Glu Tyr Pro Thr Arg Arg
1               5

<210> SEQ ID NO 3
<211> LENGTH: 11
<212> TYPE: PRT
<213> ORGANISM: Homo sapiens
<220> FEATURE:
<221> NAME/KEY: LIPID
<222> LOCATION: (9)..(9)
<223> OTHER INFORMATION: PALMITATE. Peptide AVVPCIK is a part of a
      specific trypsin-digested segment of CAV1_HUMAN, wherein residue-9
      C is palmitated.
<300> PUBLICATION INFORMATION:
<308> DATABASE ACCESSION NUMBER: Q03135
<309> DATABASE ENTRY DATE: 2012-03-29
<313> RELEVANT RESIDUES IN SEQ ID NO: (129)..(135)

<400> SEQUENCE: 3

Cys Gly Gly Gly Ala Val Val Pro Cys Ile Lys
1               5                   10
```

<210> SEQ ID NO 4
<211> LENGTH: 4
<212> TYPE: PRT
<213> ORGANISM: Homo sapiens
<220> FEATURE:
<221> NAME/KEY: LIPID
<222> LOCATION: (1)..(1)
<223> OTHER INFORMATION: Residue-1 G of the trypsin-digested peptide of
      SRC_HUMAN is myristated.
<300> PUBLICATION INFORMATION:
<308> DATABASE ACCESSION NUMBER: P12931
<309> DATABASE ENTRY DATE: 2012-03-29
<313> RELEVANT RESIDUES IN SEQ ID NO: (2)..(5)

<400> SEQUENCE: 4

Gly Ser Asn Lys
1

<210> SEQ ID NO 5
<211> LENGTH: 9
<212> TYPE: PRT
<213> ORGANISM: Homo sapiens
<220> FEATURE:
<221> NAME/KEY: LIPID
<222> LOCATION: (7)..(7)
<223> OTHER INFORMATION: Peptide SGG*CF is a part of a specific
      trypsin-digested segment of SHH_HUMAN, wherein residue-7 G* is
      covalently conjugated with cholesterol, and peptide CGGGS is
      artificially designed for conjugation of an immunogenic carrier.
<300> PUBLICATION INFORMATION:
<308> DATABASE ACCESSION NUMBER: Q15465
<309> DATABASE ENTRY DATE: 2012-03-29
<313> RELEVANT RESIDUES IN SEQ ID NO: (195)..(199)

<400> SEQUENCE: 5

Cys Gly Gly Gly Ser Gly Gly Cys Phe
1               5

<210> SEQ ID NO 6
<211> LENGTH: 9
<212> TYPE: PRT
<213> ORGANISM: Homo sapiens
<220> FEATURE:
<221> NAME/KEY: LIPID
<222> LOCATION: (6)..(6)
<223> OTHER INFORMATION: Peptide KCVLS is a part of a specific
      trypsin-digested terminal segment of RASH_HUMAN, wherein residue-6
      C is farnesylated.
<300> PUBLICATION INFORMATION:
<308> DATABASE ACCESSION NUMBER: P01112
<309> DATABASE ENTRY DATE: 2012-03-29
<313> RELEVANT RESIDUES IN SEQ ID NO: (186)..(190)

<400> SEQUENCE: 6

Cys Gly Gly Gly Lys Cys Val Leu Ser
1               5

<210> SEQ ID NO 7
<211> LENGTH: 9
<212> TYPE: PRT
<213> ORGANISM: Homo sapiens
<220> FEATURE:
<221> NAME/KEY: LIPID
<222> LOCATION: (6)..(6)
<223> OTHER INFORMATION: Peptide KCLLL is a LysN-cleaved or peptidyl-Lys
      metalloendopeptidase-cleaved segment of RAC1_HUMAN, wherein
      residue-6 C is geranylgeranylated.
<300> PUBLICATION INFORMATION:
<308> DATABASE ACCESSION NUMBER: P63000
<309> DATABASE ENTRY DATE: 2012-03-29
<313> RELEVANT RESIDUES IN SEQ ID NO: (189)..(193)

<400> SEQUENCE: 7

Cys Gly Gly Gly Lys Cys Leu Leu Leu
1               5

<210> SEQ ID NO 8
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Residue-3 X is a phosphoethanolamine derived
      from a GPI linker, GC is a trypsin-digested segment of PrP
      protein, and SGGGC is artificially designed for conjugation of an
      immunogenic carrier.
<300> PUBLICATION INFORMATION:
<308> DATABASE ACCESSION NUMBER: P04156
<309> DATABASE ENTRY DATE: 2012-03-29
<313> RELEVANT RESIDUES IN SEQ ID NO: (3)..(3)

<400> SEQUENCE: 8

Gly Cys Xaa Ser Gly Gly Gly Cys
1               5

<210> SEQ ID NO 9
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Residue-3 X is a phosphoethanolamine derived
      from a GPI linker, TS is a trypsin-digested segment of Glypican
      protein, and SGGGC is artificially designed for conjugation of an
      immunogenic carrier.
<300> PUBLICATION INFORMATION:
<308> DATABASE ACCESSION NUMBER: P35052
<309> DATABASE ENTRY DATE: 2012-03-29
<313> RELEVANT RESIDUES IN SEQ ID NO: (529)..(530)

<400> SEQUENCE: 9

Thr Ser Xaa Ser Gly Gly Gly Cys
1               5

<210> SEQ ID NO 10
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Residue-6 K is covalently conjugated to the Q
      of another synuclein via a transglutaminase. QKTV is a specific
      trypsin-digested segment of synuclein. CGGG is artificially
      desiged for conjugation of an immunogenic carrier.
<300> PUBLICATION INFORMATION:
<308> DATABASE ACCESSION NUMBER: P37840
<309> DATABASE ENTRY DATE: 2012-03-29
<313> RELEVANT RESIDUES IN SEQ ID NO: (79)..(82)

<400> SEQUENCE: 10

Cys Gly Gly Gly Gln Lys Thr Val
1               5

<210> SEQ ID NO 11
<211> LENGTH: 5
<212> TYPE: PRT
<213> ORGANISM: Homo sapiens
<220> FEATURE:
<221> NAME/KEY: MISC_FEATURE

```
<222> LOCATION: (2)..(2)
<223> OTHER INFORMATION: Peptide DQLGK is a specific trypsin-digested
      segment of synuclein, wherein residue-2 Q is covalently conjugated
      to the K of another synuclein via a transglutaminase.
<300> PUBLICATION INFORMATION:
<308> DATABASE ACCESSION NUMBER: P37840
<309> DATABASE ENTRY DATE: 2012-03-29
<313> RELEVANT RESIDUES IN SEQ ID NO: (98)..(102)

<400> SEQUENCE: 11

Asp Gln Leu Gly Lys
1               5

<210> SEQ ID NO 12
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Residue-4 K is covalently conjugated to the
      residue Q of another A4_HUMAN via a transglutaminase. GSNKGAII is
      a part of a trypsin-digested segment of A4_HUMAN.
<300> PUBLICATION INFORMATION:
<308> DATABASE ACCESSION NUMBER: P05067
<309> DATABASE ENTRY DATE: 2012-03-29
<313> RELEVANT RESIDUES IN SEQ ID NO: (96)..(103)

<400> SEQUENCE: 12

Gly Ser Asn Lys Gly Ala Ile Ile
1               5

<210> SEQ ID NO 13
<211> LENGTH: 7
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Residue-6 Q is covalently conjugated to the
      residue K of another A4_HUMAN via a transglutaminase. Peptide
      YEVHHQK is a specific trypsin-digested segment of A4_HUMAN.
<300> PUBLICATION INFORMATION:
<308> DATABASE ACCESSION NUMBER: P05067
<309> DATABASE ENTRY DATE: 2012-03-29
<313> RELEVANT RESIDUES IN SEQ ID NO: (681)..(687)

<400> SEQUENCE: 13

Tyr Glu Val His His Gln Lys
1               5

<210> SEQ ID NO 14
<211> LENGTH: 7
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: Peptide TFG is a specific GluC-cleaved segment
      of LC3B_HUMAN, and peptide GGGC is artificially desiged for
      conjugation of an immunogenmic carrier.
<300> PUBLICATION INFORMATION:
<308> DATABASE ACCESSION NUMBER: Q9GZQ8
<309> DATABASE ENTRY DATE: 2012-03-29
<313> RELEVANT RESIDUES IN SEQ ID NO: (118)..(120)

<400> SEQUENCE: 14

Thr Phe Gly Gly Gly Gly Cys
1               5

<210> SEQ ID NO 15
```

```
<211> LENGTH: 10
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: Peptide VYASQETFG is a specific cyanogen
      bromide (CNBr)-cleaved segment of LC3B_HUMAN.
<300> PUBLICATION INFORMATION:
<308> DATABASE ACCESSION NUMBER: Q9GZQ8
<309> DATABASE ENTRY DATE: 2012-03-29
<313> RELEVANT RESIDUES IN SEQ ID NO: (112)..(120)

<400> SEQUENCE: 15

Val Tyr Ala Ser Gln Glu Thr Phe Gly Cys
1               5                   10

<210> SEQ ID NO 16
<211> LENGTH: 19
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: Peptide KDEDGFLYMVYASQETFG is the
      trypsin-cleaved C-terminal segment of LC3B_HUMAN.
<300> PUBLICATION INFORMATION:
<308> DATABASE ACCESSION NUMBER: Q9GZQ8
<309> DATABASE ENTRY DATE: 2012-03-29
<313> RELEVANT RESIDUES IN SEQ ID NO: (104)..(120)

<400> SEQUENCE: 16

Lys Asp Glu Asp Gly Phe Leu Tyr Met Val Tyr Ala Ser Gln Glu Thr
1               5                   10                  15

Phe Gly Cys

<210> SEQ ID NO 17
<211> LENGTH: 11
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: Residue-11 X is a phosphoethanolamine and is
      covalently linked to the N-terminal G of LC3B_HUMAN
<300> PUBLICATION INFORMATION:
<308> DATABASE ACCESSION NUMBER: Q9GZQ8
<309> DATABASE ENTRY DATE: 2012-03-29
<313> RELEVANT RESIDUES IN SEQ ID NO: (116)..(120)

<400> SEQUENCE: 17

Cys Gly Gly Gly Ser Gln Glu Thr Phe Gly Xaa
1               5                   10

<210> SEQ ID NO 18
<211> LENGTH: 6
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Peptide NYNKSD is a segment of TRFE_HUMAN,
      wherein residue-3 N is covalently conjugated either to N-acetyl-D-
      glucosamine (GlcNAc) or alpha-1,6-fucosylated GlcNAc.
<300> PUBLICATION INFORMATION:
<308> DATABASE ACCESSION NUMBER: P02787
<309> DATABASE ENTRY DATE: 2012-03-30
<313> RELEVANT RESIDUES IN SEQ ID NO: (430)..(435)

<400> SEQUENCE: 18

Asn Tyr Asn Lys Ser Asp
```

```
<210> SEQ ID NO 19
<211> LENGTH: 15
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide QDQCIYNTTYLNVQR is a segment of
      A1AG1_HUMAN, wherein residue-7 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P02763
<309> DATABASE ENTRY DATE: 2012-03-30
<313> RELEVANT RESIDUES IN SEQ ID NO: (88)..(102)

<400> SEQUENCE: 19

Gln Asp Gln Cys Ile Tyr Asn Thr Thr Tyr Leu Asn Val Gln Arg
1               5                   10                  15

<210> SEQ ID NO 20
<211> LENGTH: 15
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide QNQCFYNSSYLNVQR is a segment of
      A1AG2_HUMAN, wherein residue-7 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P19652
<309> DATABASE ENTRY DATE: 2012-03-30
<313> RELEVANT RESIDUES IN SEQ ID NO: (87)..(101)

<400> SEQUENCE: 20

Gln Asn Gln Cys Phe Tyr Asn Ser Ser Tyr Leu Asn Val Gln Arg
1               5                   10                  15

<210> SEQ ID NO 21
<211> LENGTH: 23
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Peptide ADTHDEILEGLNFNLTEIPEAQI is a aprt of a
      segment of P01009_A1AT_HUMAN, wherein residue-14 N is covalently
      conjugated either to N-acetyl-D-glucosamine (GlcNAc) or alpha-1,6-
      fucosylated GlcNAc.
<300> PUBLICATION INFORMATION:
<308> DATABASE ACCESSION NUMBER: P01009
<309> DATABASE ENTRY DATE: 2012-03-30
<313> RELEVANT RESIDUES IN SEQ ID NO: (94)..(116)

<400> SEQUENCE: 21

Ala Asp Thr His Asp Glu Ile Leu Glu Gly Leu Asn Phe Asn Leu Thr
1               5                   10                  15

Glu Ile Pro Glu Ala Gln Ile
            20

<210> SEQ ID NO 22
<211> LENGTH: 21
<212> TYPE: PRT
<213> ORGANISM: Homo sapiens
<220> FEATURE:
<221> NAME/KEY: MISC_FEATURE
<222> LOCATION: (13)..(13)
```

```
<223> OTHER INFORMATION: Peptide VCQDCPLLAPLNDTRVVHAAK is a segment of
      FETUA_HUMAN, wherein residue-13 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P02765
<309> DATABASE ENTRY DATE: 2012-03-30
<313> RELEVANT RESIDUES IN SEQ ID NO: (145)..(159)

<400> SEQUENCE: 22

Val Cys Gln Asp Cys Pro Leu Leu Ala Pro Leu Asn Asp Thr Arg Val
1               5                   10                  15

Val His Ala Ala Lys
            20

<210> SEQ ID NO 23
<211> LENGTH: 18
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Peptide DIVEYYNDSNGSHVLQGR is a segment of
      P25311 (ZA2G_HUMAN), wherein residue-10 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: P25311
<309> DATABASE ENTRY DATE: 2012-03-30
<313> RELEVANT RESIDUES IN SEQ ID NO: (103)..(120)

<400> SEQUENCE: 23

Asp Ile Val Glu Tyr Tyr Asn Asp Ser Asn Gly Ser His Val Leu Gln
1               5                   10                  15

Gly Arg

<210> SEQ ID NO 24
<211> LENGTH: 22
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: Peptide ADGTVNQIEGEATPVNLTEPAK is a segment of
      P05090 (APOD_HUMAN), wherein residue-16 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: P05090
<309> DATABASE ENTRY DATE: 2012-03-30
<313> RELEVANT RESIDUES IN SEQ ID NO: (83)..(104)

<400> SEQUENCE: 24

Ala Asp Gly Thr Val Asn Gln Ile Glu Gly Glu Ala Thr Pro Val Asn
1               5                   10                  15

Leu Thr Glu Pro Ala Lys
            20

<210> SEQ ID NO 25
<211> LENGTH: 18
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: Peptide IPCSQPPQIEHGTINSSR is a segment of
      P08603 (CFAH_HUMAN), wherein residue-15 N is covalently conjugated
      either to N-acetyl-D-glucosamine (GlcNAc) or alpha-1,6-fucosylated
      GlcNAc.
<300> PUBLICATION INFORMATION:
```

<308> DATABASE ACCESSION NUMBER: P08603
<309> DATABASE ENTRY DATE: 2012-03-30
<313> RELEVANT RESIDUES IN SEQ ID NO: (868)..(885)

<400> SEQUENCE: 25

Ile Pro Cys Ser Gln Pro Pro Gln Ile Glu His Gly Thr Ile Asn Ser
1               5                   10                  15

Ser Arg

<210> SEQ ID NO 26
<211> LENGTH: 18
<212> TYPE: PRT
<213> ORGANISM: Homo sapiens
<220> FEATURE:
<221> NAME/KEY: MISC_FEATURE
<222> LOCATION: (5)..(9)
<223> OTHER INFORMATION: Peptide NLFLNHSENATAKDIAPT is a segment of
      P00738 (HPT_HUMAN), wherein residues N-5 and N-9 are covalently
      conjugated either to N-acetyl-D-glucosamine (GlcNAc) or alpha-1,6-
      fucosylated GlcNAc.
<300> PUBLICATION INFORMATION:
<308> DATABASE ACCESSION NUMBER: P00738
<309> DATABASE ENTRY DATE: 2012-03-30
<313> RELEVANT RESIDUES IN SEQ ID NO: (203)..(220)

<400> SEQUENCE: 26

Asn Leu Phe Leu Asn His Ser Glu Asn Ala Thr Ala Lys Asp Ile Ala
1               5                   10                  15

Pro Thr

<210> SEQ ID NO 27
<211> LENGTH: 13
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide SWPAVGNCSSALR is a segment of P02790
      (HEMO_HUMAN), wherein residue-7 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P02790
<309> DATABASE ENTRY DATE: 2012-03-30
<313> RELEVANT RESIDUES IN SEQ ID NO: (181)..(193)

<400> SEQUENCE: 27

Ser Trp Pro Ala Val Gly Asn Cys Ser Ser Ala Leu Arg
1               5                   10

<210> SEQ ID NO 28
<211> LENGTH: 18
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Peptide GLTFQQNASSMCVPDQDT is a segment of
      P01871 (IGHM_HUMAN), wherein residue-7 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: P01871
<309> DATABASE ENTRY DATE: 2012-03-30
<313> RELEVANT RESIDUES IN SEQ ID NO: (203)..(220)

<400> SEQUENCE: 28

Gly Leu Thr Phe Gln Gln Asn Ala Ser Ser Met Cys Val Pro Asp Gln
1               5                   10                  15

-continued

Asp Thr

<210> SEQ ID NO 29
<211> LENGTH: 19
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Peptide HGIQYFNNNTQHSSLFMLN is a segment of
      P01042 (KNG1_HUMAN), wherein residue-8 N is covalently conjugated
      either to N-acetyl-D-glucosamine (GlcNAc) or alpha-1,6-fucosylated
      GlcNAc
<300> PUBLICATION INFORMATION:
<308> DATABASE ACCESSION NUMBER: P01042
<309> DATABASE ENTRY DATE: 2012-03-30
<313> RELEVANT RESIDUES IN SEQ ID NO: (162)..(180)

<400> SEQUENCE: 29

His Gly Ile Gln Tyr Phe Asn Asn Asn Thr Gln His Ser Ser Leu Phe
1               5                   10                  15

Met Leu Asn

<210> SEQ ID NO 30
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Peptide LNAENNATFYFK is a segment of P01042
      (KNG1_HUMAN), wherein residue-6 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P01042
<309> DATABASE ENTRY DATE: 2012-03-30
<313> RELEVANT RESIDUES IN SEQ ID NO: (289)..(300)

<400> SEQUENCE: 30

Leu Asn Ala Glu Asn Asn Ala Thr Phe Tyr Phe Lys
1               5                   10

<210> SEQ ID NO 31
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Peptide CGLVPVLAENYNKSDNCEDT is a segment of
      P02787 (TRFE_HUMAN), wherein residue-12 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: P02787
<309> DATABASE ENTRY DATE: 2012-03-30
<313> RELEVANT RESIDUES IN SEQ ID NO: (421)..(440)

<400> SEQUENCE: 31

Cys Gly Leu Val Pro Val Leu Ala Glu Asn Tyr Asn Lys Ser Asp Asn
1               5                   10                  15

Cys Glu Asp Thr
            20

<210> SEQ ID NO 32
<211> LENGTH: 19
<212> TYPE: PRT
<213> ORGANISM: Homo sapiens
<220> FEATURE:

```
<221> NAME/KEY: MISC_FEATURE
<222> LOCATION: (9)..(9)
<223> OTHER INFORMATION: Peptide QQQHLFGSNVTDCSGNFCL is a segment of
      P02787 (TRFE_HUMAN), wherein residue-9 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: P02787
<309> DATABASE ENTRY DATE: 2012-03-30
<313> RELEVANT RESIDUES IN SEQ ID NO: (622)..(640)

<400> SEQUENCE: 32

Gln Gln Gln His Leu Phe Gly Ser Asn Val Thr Asp Cys Ser Gly Asn
1               5                   10                  15

Phe Cys Leu

<210> SEQ ID NO 33
<211> LENGTH: 16
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Peptide EHEGAIYPDNTTDFQR is a segment of P00450
      (CERU_HUMAN), wherein residue-10 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P00450
<309> DATABASE ENTRY DATE: 2012-03-30
<313> RELEVANT RESIDUES IN SEQ ID NO: (129)..(144)

<400> SEQUENCE: 33

Glu His Glu Gly Ala Ile Tyr Pro Asp Asn Thr Thr Asp Phe Gln Arg
1               5                   10                  15

<210> SEQ ID NO 34
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Peptide VVFTANDSGPR is a segment of P02766
      (TTHY_HUMAN), wherein residue-6 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P02766
<309> DATABASE ENTRY DATE: 2012-03-30
<313> RELEVANT RESIDUES IN SEQ ID NO: (113)..(123)

<400> SEQUENCE: 34

Val Val Phe Thr Ala Asn Asp Ser Gly Pro Arg
1               5                   10

<210> SEQ ID NO 35
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Peptide YFYNGTSMACETFQ is a segment of B7Z8R6
      (B7Z8R6_HUMAN), wherein residue-4 N is covalently conjugated
      either to N-acetyl-D-glucosamine (GlcNAc) or alpha-1,6-fucosylated
      GlcNAc.
<300> PUBLICATION INFORMATION:
<308> DATABASE ACCESSION NUMBER: B7Z8R6
<309> DATABASE ENTRY DATE: 2012-03-30
<313> RELEVANT RESIDUES IN SEQ ID NO: (188)..(201)
```

-continued

```
<400> SEQUENCE: 35

Tyr Phe Tyr Asn Gly Thr Ser Met Ala Cys Glu Thr Phe Gln
1               5                   10

<210> SEQ ID NO 36
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Peptide PFYLTNSSGVD is a segment of Q08380
      (LG3BP_HUMAN), wherein residue-6 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: Q08380
<309> DATABASE ENTRY DATE: 2012-03-30
<313> RELEVANT RESIDUES IN SEQ ID NO: (575)..(585)

<400> SEQUENCE: 36

Pro Phe Tyr Leu Thr Asn Ser Ser Gly Val Asp
1               5                   10

<210> SEQ ID NO 37
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Peptide AVLVNNITTGER is a segment of Q8NBJ4
      (GOLM1_HUMAN), wherein residue-6 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: Q8NBJ4
<309> DATABASE ENTRY DATE: 2012-03-30
<313> RELEVANT RESIDUES IN SEQ ID NO: (104)..(115)

<400> SEQUENCE: 37

Ala Val Leu Val Asn Asn Ile Thr Thr Gly Glu Arg
1               5                   10

<210> SEQ ID NO 38
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Peptide EHVKNSTYTA is a segment of P12830
      (CADH1_HUMAN), wherein residue-5 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P12830
<309> DATABASE ENTRY DATE: 2012-03-30
<313> RELEVANT RESIDUES IN SEQ ID NO: (554)..(563)

<400> SEQUENCE: 38

Glu His Val Lys Asn Ser Thr Tyr Thr Ala
1               5                   10

<210> SEQ ID NO 39
<211> LENGTH: 14
<212> TYPE: PRT
<213> ORGANISM: Homo sapiens
<220> FEATURE:
<221> NAME/KEY: MISC_FEATURE
<222> LOCATION: (9)..(9)
```

-continued

<223> OTHER INFORMATION: Peptide ELTHGASANWTIQY is a segment of P12830
      (CADH1_HUMAN), wherein residue-9 N is covalently conjugated either
      to N-acetyl-D-glucosamine (GlcNAc) or alpha-1,6-fucosylated
      GlcNAc.
<300> PUBLICATION INFORMATION:
<308> DATABASE ACCESSION NUMBER: P12830
<309> DATABASE ENTRY DATE: 2012-03-30
<313> RELEVANT RESIDUES IN SEQ ID NO: (629)..(642)

<400> SEQUENCE: 39

Glu Leu Thr His Gly Ala Ser Ala Asn Trp Thr Ile Gln Tyr
1               5                   10

<210> SEQ ID NO 40
<211> LENGTH: 7
<212> TYPE: PRT
<213> ORGANISM: Homo sapiens
<220> FEATURE:
<221> NAME/KEY: BINDING
<222> LOCATION: (1)..(4)
<223> OTHER INFORMATION: Peptide IVIVMSK is a specific trypsin-digested
      segment of O00257 (CBX4_HUMAN), wherein IVIV is the hidden binding
      site epitope.
<300> PUBLICATION INFORMATION:
<308> DATABASE ACCESSION NUMBER: O00257
<309> DATABASE ENTRY DATE: 2012-03-30
<313> RELEVANT RESIDUES IN SEQ ID NO: (262)..(268)

<400> SEQUENCE: 40

Ile Val Ile Val Met Ser Lys
1               5

<210> SEQ ID NO 41
<211> LENGTH: 29
<212> TYPE: PRT
<213> ORGANISM: Homo sapiens
<220> FEATURE:
<221> NAME/KEY: BINDING
<222> LOCATION: (15)..(18)
<223> OTHER INFORMATION: Peptide PADLPPAAALPQPEVILLDSDLDEPIDLR is a
      specific trypsin-digested segment of O00257 (CBX4_HUMAN), wherein
      VILL is the hidden binding site epitope.
<300> PUBLICATION INFORMATION:
<308> DATABASE ACCESSION NUMBER: O00257
<309> DATABASE ENTRY DATE: 2012-03-30
<313> RELEVANT RESIDUES IN SEQ ID NO: (462)..(465)

<400> SEQUENCE: 41

Pro Ala Asp Leu Pro Pro Ala Ala Ala Leu Pro Gln Pro Glu Val Ile
1               5                   10                  15

Leu Leu Asp Ser Asp Leu Asp Glu Pro Ile Asp Leu Arg
            20                  25

<210> SEQ ID NO 42
<211> LENGTH: 10
<212> TYPE: PRT
<213> ORGANISM: Homo sapiens
<220> FEATURE:
<221> NAME/KEY: BINDING
<222> LOCATION: (1)..(4)
<223> OTHER INFORMATION: Peptide VILLDSDLDE is a specific GluC-digested
      segment of O00257 (CBX4_HUMAN), wherein VILL is the hidden binding
      site epitope.
<300> PUBLICATION INFORMATION:
<308> DATABASE ACCESSION NUMBER: O00257
<309> DATABASE ENTRY DATE: 2012-03-30
<313> RELEVANT RESIDUES IN SEQ ID NO: (462)..(465)

<400> SEQUENCE: 42

Val Ile Leu Leu Asp Ser Asp Leu Asp Glu
1               5                   10

```
<210> SEQ ID NO 43
<211> LENGTH: 22
<212> TYPE: PRT
<213> ORGANISM: Homo sapiens
<220> FEATURE:
<221> NAME/KEY: BINDING
<222> LOCATION: (1)..(4)
<223> OTHER INFORMATION: Peptide VEVIDLTIDSSSDEEEEEPSAK is a specific
      trypsin-digested segment of O75925 (PIAS1_HUMAN), wherein VEVI is
      the hidden binding site epitope.
<300> PUBLICATION INFORMATION:
<308> DATABASE ACCESSION NUMBER: O75925
<309> DATABASE ENTRY DATE: 2012-03-30
<313> RELEVANT RESIDUES IN SEQ ID NO: (458)..(461)

<400> SEQUENCE: 43

Val Glu Val Ile Asp Leu Thr Ile Asp Ser Ser Ser Asp Glu Glu
1               5                   10                  15

Glu Glu Pro Ser Ala Lys
            20

<210> SEQ ID NO 44
<211> LENGTH: 29
<212> TYPE: PRT
<213> ORGANISM: Homo sapiens
<220> FEATURE:
<221> NAME/KEY: BINDING
<222> LOCATION: (16)..(19)
<223> OTHER INFORMATION: Peptide HQVASHHQSSNKNKKVEVIDLTIDSSSDE is a
      specific GluC-digested segment of O75925 (PIAS1_HUMAN), wherein
      VEVI is the hidden hydrophobic site epitope and folded inside of
      the protein.
<300> PUBLICATION INFORMATION:
<308> DATABASE ACCESSION NUMBER: O75925
<309> DATABASE ENTRY DATE: 2012-03-30
<313> RELEVANT RESIDUES IN SEQ ID NO: (457)..(460)

<400> SEQUENCE: 44

His Gln Val Ala Ser His His Gln Ser Ser Asn Lys Asn Lys Lys Val
1               5                   10                  15

Glu Val Ile Asp Leu Thr Ile Asp Ser Ser Ser Asp Glu
            20                  25

<210> SEQ ID NO 45
<211> LENGTH: 28
<212> TYPE: PRT
<213> ORGANISM: Homo sapiens
<220> FEATURE:
<221> NAME/KEY: BINDING
<222> LOCATION: (1)..(4)
<223> OTHER INFORMATION: Peptide VVVISSSEDSDAENSVSSSPQSEVLYWK is a
      specific trypsin-digested segment of P29590 (PML_HUMAN), wherein
      VVVI is the hidden hydrophobic site epitope and is folded inside
      of the protein.
<300> PUBLICATION INFORMATION:
<308> DATABASE ACCESSION NUMBER: P29590
<309> DATABASE ENTRY DATE: 2012-03-30
<313> RELEVANT RESIDUES IN SEQ ID NO: (556)..(559)

<400> SEQUENCE: 45

Val Val Val Ile Ser Ser Ser Glu Asp Ser Asp Ala Glu Asn Ser Val
1               5                   10                  15

Ser Ser Ser Pro Gln Ser Glu Val Leu Tyr Trp Lys
            20                  25

<210> SEQ ID NO 46
<211> LENGTH: 9
<212> TYPE: PRT
```

```
<213> ORGANISM: Homo sapiens
<220> FEATURE:
<221> NAME/KEY: BINDING
<222> LOCATION: (2)..(5)
<223> OTHER INFORMATION: Peptide RVVVISSSE is a specific GluC-digested
      segment of P29590 (PML_HUMAN), wherein VVVI is the hidden
      hydrophobic site epitope and is folded inside of the protein.
<300> PUBLICATION INFORMATION:
<308> DATABASE ACCESSION NUMBER: P29590
<309> DATABASE ENTRY DATE: 2012-03-30
<313> RELEVANT RESIDUES IN SEQ ID NO: (556)..(559)

<400> SEQUENCE: 46

Arg Val Val Val Ile Ser Ser Ser Glu
1               5

<210> SEQ ID NO 47
<211> LENGTH: 23
<212> TYPE: PRT
<213> ORGANISM: Homo sapiens
<220> FEATURE:
<221> NAME/KEY: BINDING
<222> LOCATION: (10)..(13)
<223> OTHER INFORMATION: Peptide PEDSPSDDDVLIVYELTPTAEQK is a specific
      trypsin-digested segment of P49792 (RBP2_HUMAN), wherein VLIV is
      the hidden hydrophobic binding site epitope and is folded inside
      of the protein.
<300> PUBLICATION INFORMATION:
<308> DATABASE ACCESSION NUMBER: P49792
<309> DATABASE ENTRY DATE: 2012-03-30
<313> RELEVANT RESIDUES IN SEQ ID NO: (2632)..(2635)

<400> SEQUENCE: 47

Pro Glu Asp Ser Pro Ser Asp Asp Asp Val Leu Ile Val Tyr Glu Leu
1               5                   10                  15

Thr Pro Thr Ala Glu Gln Lys
            20

<210> SEQ ID NO 48
<211> LENGTH: 13
<212> TYPE: PRT
<213> ORGANISM: Homo sapiens
<220> FEATURE:
<221> NAME/KEY: BINDING
<222> LOCATION: (8)..(11)
<223> OTHER INFORMATION: Peptide DSPSDDDVLIVYE is a specific
      GluC-digested segment of P49792 (RBP2_HUMAN), wherein VLIV is the
      hidden binding site epitope.
<300> PUBLICATION INFORMATION:
<308> DATABASE ACCESSION NUMBER: P49792
<309> DATABASE ENTRY DATE: 2012-03-30
<313> RELEVANT RESIDUES IN SEQ ID NO: (2632)..(2635)

<400> SEQUENCE: 48

Asp Ser Pro Ser Asp Asp Asp Val Leu Ile Val Tyr Glu
1               5                   10

<210> SEQ ID NO 49
<211> LENGTH: 20
<212> TYPE: PRT
<213> ORGANISM: Homo sapiens
<220> FEATURE:
<221> NAME/KEY: BINDING
<222> LOCATION: (12)..(15)
<223> OTHER INFORMATION: Peptide YISVGSQADTNVIDLTGDDK is a specific
      trypsin-digested segment of Q9UHP3 (UBP25_HUMAN), wherein VIDL is
      the hidden binding site epitope.
<300> PUBLICATION INFORMATION:
<308> DATABASE ACCESSION NUMBER: Q9UHP3
<309> DATABASE ENTRY DATE: 2012-03-30
<313> RELEVANT RESIDUES IN SEQ ID NO: (91)..(94)
```

```
<400> SEQUENCE: 49

Tyr Ile Ser Val Gly Ser Gln Ala Asp Thr Asn Val Ile Asp Leu Thr
1               5                   10                  15

Gly Asp Asp Lys
            20

<210> SEQ ID NO 50
<211> LENGTH: 46
<212> TYPE: PRT
<213> ORGANISM: Homo sapiens
<220> FEATURE:
<221> NAME/KEY: BINDING
<222> LOCATION: (25)..(28)
<223> OTHER INFORMATION: Peptide
      TTYYQTALPGNDRYISVGSQADTNVIDLTGDDKDDLQRAIALSLAE is a specific
      GluC-digested segment of Q9UHP3 (UBP25_HUMAN), wherein VIDL is the
      hidden binding site epitope.
<300> PUBLICATION INFORMATION:
<308> DATABASE ACCESSION NUMBER: Q9UHP3
<309> DATABASE ENTRY DATE: 2012-03-30
<313> RELEVANT RESIDUES IN SEQ ID NO: (91)..(94)

<400> SEQUENCE: 50

Thr Thr Tyr Tyr Gln Thr Ala Leu Pro Gly Asn Asp Arg Tyr Ile Ser
1               5                   10                  15

Val Gly Ser Gln Ala Asp Thr Asn Val Ile Asp Leu Thr Gly Asp Asp
            20                  25                  30

Lys Asp Asp Leu Gln Arg Ala Ile Ala Leu Ser Leu Ala Glu
        35                  40                  45

<210> SEQ ID NO 51
<211> LENGTH: 52
<212> TYPE: PRT
<213> ORGANISM: Homo sapiens
<220> FEATURE:
<221> NAME/KEY: BINDING
<222> LOCATION: (46)..(49)
<223> OTHER INFORMATION: Peptide
      EATSTPEISLEAEPIELVETAGDEIVDLTCESLEPVVVDLTHNDSVVIVDER is a specific
      trypsin-digested segment of P78317 (RNF4_HUMAN), wherein VVIV is
      the hidden binding site epitope.
<300> PUBLICATION INFORMATION:
<308> DATABASE ACCESSION NUMBER: P78317
<309> DATABASE ENTRY DATE: 2012-03-30
<313> RELEVANT RESIDUES IN SEQ ID NO: (67)..(70)

<400> SEQUENCE: 51

Glu Ala Thr Ser Thr Pro Glu Ile Ser Leu Glu Ala Glu Pro Ile Glu
1               5                   10                  15

Leu Val Glu Thr Ala Gly Asp Glu Ile Val Asp Leu Thr Cys Glu Ser
            20                  25                  30

Leu Glu Pro Val Val Val Asp Leu Thr His Asn Asp Ser Val Val Ile
        35                  40                  45

Val Asp Glu Arg
    50

<210> SEQ ID NO 52
<211> LENGTH: 17
<212> TYPE: PRT
<213> ORGANISM: Homo sapiens
<220> FEATURE:
<221> NAME/KEY: BINDING
<222> LOCATION: (12)..(15)
<223> OTHER INFORMATION: Peptide PVVVDLTHNDSVVIVDE is a specific
      trypsin-digested segment of P78317 (RNF4_HUMAN), wherein VVIV is
      the hidden hydrophobic binding site epitope and is folded inside
      of the protein.
```

-continued

```
<300> PUBLICATION INFORMATION:
<308> DATABASE ACCESSION NUMBER: P78317
<309> DATABASE ENTRY DATE: 2012-03-30
<313> RELEVANT RESIDUES IN SEQ ID NO: (67)..(70)

<400> SEQUENCE: 52

Pro Val Val Val Asp Leu Thr His Asn Asp Ser Val Val Ile Val Asp
1               5                   10                  15

Glu
```

METHODS OF DETECTING CONJUGATION SITE-SPECIFIC AND HIDDEN EPITOPE/ANTIGEN

CROSS-REFERENCE TO RELATED APPLICATIONS

This application is a continuation of U.S. patent application Ser. No. 13/312,285, filed Dec. 6, 2011, which claims priority to Ser. No. 61/420,354 filed on Dec. 7, 2010, both incorporated herein by reference in their entirety.

TECHNICAL FIELD

The present description relates to methods, antibodies, reagents, immunoassays and kits for designing and detecting hidden antigens, including, but not limited to macromolecule-to-macromolecule conjugation sites or any types of hidden antigens, either in situ or ex situ in sample preparations, collectively defined as the ACE methods, and their use thereof.

BACKGROUND OF THE INVENTION

It is estimated that about 50,000-100,000 antibodies are currently available worldwide representing about 5,000-10,000 different genes/proteins. This number is significantly below 400,000 proteins in the proteome, and millions of other "antibodiable" antigens. Furthermore, most antibodies don't work as the users intend, and about 75% of antibodies do not work in all antibody-based applications (http://www.sdix.com/Products/Custom-Antibody-Services/Engagement/Antibodies.aspx?Q=2). A key reason of much fewer antibodies than "antibodiable" antigens is that many antigens are hidden in samples or sample preparations and thus poorly accessible to antibodies. This invention discloses a method of designing and detecting hidden antigens.

Post-translational conjugation of a protein by another protein, polysaccharide, lipid and nucleic acid, or any combination of the above plays a key role virtually in every aspect of cellular functions. A conjugated molecule is either a monomeric single-molecule or a polymeric macromolecule with either a linear or a branched structure. Macromolecules include, but are not limited to, proteins or polypeptides, polysaccharides, adenosine diphosphate (ADP)-ribosyls, fatty acids, polynucleotides, glycosylphosphatidylinositol (GPI) anchors, ubiquitin, small ubiquitin-like modifier (SUMO), neural precursor cell expressed, developmentally down-regulated 8 (NEDD8), interferon-stimulated gene 15 kDa (ISG15), and other ubiquitin-like molecules (UBLs).

Many types of human diseases display abnormal molecular conjugation. For example, abnormal glycosylation occurs in many types of cancers (Mehta and Block, 2008). Ubiquitin-containing conjugates are present virtually in all types of neurodegenerative diseases (Dohm et al., 2008). Telomeric aggregates accumulate in tumor cells (Mai and Garini, 2006). Advanced glycation adducts are found in samples obtained from patients with heart disease and/or diabetes (Thornalley, 2002; Meerwaldt et al., 2008). Disease-specific macromolecule-to-macromolecule conjugates are present in body fluids such as blood serum or cerebrospinal fluid (CSF), but few reliable methods are currently available to detect them. However, most, if not all, macromolecule-to-macromolecule conjugation sites are hidden antigens (see FIG. 4 below). Therefore, antibodies to macromolecule-to-macromolecule conjugation sites are difficult to make and are not currently available for assays of macromolecule-to-macromolecule conjugation sites in all antibody-based applications.

Methods of making antibodies against post-translational modified proteins in the form of a small monomeric molecule, including phosphorylation, acetylation, methylation, and nitrolization, are well established. In comparison to monomeric modification site-specific antibodies, there is no effective method currently available for making polymeric macromolecular conjugation site-specific antibodies. Macromolecular conjugation can be defined as covalent conjugation between two polymeric biomolecules, including, but not limited to, protein glycosylation, lipidation, ADP-ribosylation, ubiquitination, sumoylation, NEDDylation, ISGylation, GPI-anchor, transglutaminase-mediated cross-links, and the like.

In the post-genomic era, our knowledge of macromolecule-to-macromolecule conjugation and its relation to diseases has grown exponentially. This provides an opportunity to develop novel methods for detecting macromolecule-to-macromolecule conjugation in a conjugation site-specific manner. For that reason, investigators have devoted extensive efforts to generation of macromolecule-to-macromolecule conjugation site-specific antibodies by conventional antigen design, antibody-making, and antigen detection methods. However, these efforts have been so far proven futile (Matsumoto et al., 2008). As a result, there are few conjugation site-specific antibodies currently available. Therefore, new methods for detecting hidden antigen/epitopes, including but not limited to macromolecular conjugation-sites and linear hidden antigens, are desperately needed, and can provide useful tools for all antibody- and antigen-based applications.

An example is making ubiquitin-to-protein conjugation site-specific antibodies. Protein ubiquitination involves virtually all protein degradation as well as other biological processes. There are a few previous reports of generation of anti-polyubiquitin antibodies. Pirim (1998) reported an anti-polyubiquitin antibody. However, this antibody does not recognize isopeptide bond-branched ubiquitin-to-ubiquitin conjugation, which are dominant forms of cellular ubiquitin conjugates. Rather this antibody recognizes head-to-tail (c- to n-terminal conjugation) poly-ubiquitins, which represent a very tiny/small fraction of polyubiquitin transiently formed during synthesis of free ubiquitin.

Fujimuro et al. (2005) reported anti-polyubiquitin monoclonal antibodies named as FK1 and FK2. Both FK1 and FK2 antibodies recognize the polyubiquitin chain. However, there are two fundamental differences between making FK1 and FK2 antibodies and the methods described in the claims of the present invention: (i) FK1 and FK2 were made by using regular polyubiquitin antigens; and (ii) FK1 and FK2 cannot recognize specific conjugation sites of ubiquitinated proteins (Fujimuro et al., 2005). Therefore, FK1 and FK2 are not conjugation site-specific antibodies, rather than general polyubiquitin antibodies.

Similarly, there are reports of using antibodies to the glycine-glycine-to-(lysine) structure for profiling of ubiquitinated proteins and identification of the peptides with liquid chromatography-tandem mass spectrometry (LC-MS/MS) (Peng et al., 2003; Denis et al., 2007; Xu et al., 2010). The glycine-glycine-to-(lysine) structure was prepared by reacting lysine-rich histone III-S protein with t-butyloxycarbonyl-Gly-Gly-N-hydroxysuccinimide (Boc-Gly-Gly-NHS) (Xu et al., 2010). However, the glycine-glycine-to-(lysine) antibodies recognize only the glycine-glycine-to-(lysine), rather than the lysine surrounding sequence of a specific ubiquitinated protein, and thus they are also not conjugation site-specific antibodies, and cannot be used to detect individual ubiquitin-to-protein conjugation sites. In addition, the glycine-glycine-to-(lysine) antibodies cannot be used in regular antibody-based applications, rather they were developed for the pre-LC-MS/MS profiling applications (Peng et al., 2003; Denis et al., 2007; Xu et al., 2010). In comparison, the inventive methods are for designing and detecting the specific conjugation sites of both conjugation moieties. Therefore, conjugation site-specific antibodies developed by the inventive ACE methods, can recognize specifically both the branched glycine-glycine and the conjugation site lysine surrounding sequence as well as can be used for detecting hidden antigens in all antibody-based applications (see FIGS. 1-13).

Matsumoto et al. (2008) generated two linkage-specific antibodies that recognize polyubiquitin chains through lysine 63 (K63) or 48 (K48) linkage (US patent 20070218069A). However, there are several fundamental differences between the method of making these two linkage-specific antibodies and the methods of the present invention. The "antibodies" made by Matsumoto et al. (2008) were not generated by conventional animal immunization methods, rather by a phage display approach of random screening of the ubiquitin conjugation site binders. This phage display approach has advantage to be able to select binding partners from millions of other irrelevant proteins, but these binding partners are "antibody-like" fusion proteins. Also, the phage display approach usually has technical challenges associated with it. For instance, it is acknowledged that the affinity and specificity of binding partners generated by phage display are often suboptimal, relative to conventional antibody, and the loss of the original heavy- and light-chain pairings is also a challenge. Perhaps for these reasons, phage display has not been widely used to make "antibodies" (Ward, 2002). In comparison, the present invention uses the Artificially Cleaved Epitope (ACE, see below) strategy for designing and detecting macromolecular conjugation site-specific and linear hidden antigens, which are proven to be more effective and reliable (see FIGS. 1-14 below).

There are several patented methods for making peptide antibodies. Patent WO 02/25287 describes methods for analysis of proteins by producing a mixture of peptides and contacting the mixture of peptides to filtering agents or antibodies in order to decrease the complexity of a mixture prior to the application of an analytical technique such as mass spectrometry. U.S. Pat. No. 7,460,960 described methods by the use of capture agents or antibodies that interact with the Proteome Epitope Tags (PETs) in a sample. However, these methods cannot be used to design and detect hidden antigens, and they are also principally and profoundly different with the methods of the present invention.

Currently, there are several cleavage site-specific antibodies commercially available. U.S. Pat. No. 7,803,553 by Kojima et al. described an antibody for detecting an active form of TGF-β1 naturally cleaved in vivo. U.S. Pat. No. 6,762,045 by Krebs et al. described an antibody to naturally cleaved caspase-3. All currently available cleavage-specific antibodies were developed to detect the naturally occurring cleavage sites in vivo, and cannot be used to detect hidden antigens such as macromolecule-to-macromolecule conjugation sites. In contrast, the present inventive methods are to design and detect "Artificially Cleaved Epitopes (ACEs, see below)" of hidden antigens that are not naturally present or exposed. The inventive ACE methods do not include those for detecting naturally cleaved epitopes in samples.

Macromolecules other than polypeptides can also be used to generate antibodies successfully, including, but not limited to, antibodies to lipids, nucleic acids, and saccharide. For example, a mouse monoclonal antibody (e.g., CTD110.6) recognizing the single O-linked N-acetylglucosamine is commercially available. A mouse antibody (e.g., clone 26-5) to a lipid structure is also reported (Young et al., 1987). However, polysaccharide-to-protein and lipid-to-protein conjugation site-specific antibodies are not currently available, most probably because they are hidden antigen and no reliable methods can successfully make them.

SUMMARY OF THE INVENTION

The present invention discloses the "Artificially Cleaved Epitope" or ACE methods, antibodies, reagents, immunoassays and kits for designing and detecting hidden antigens, collectively defined as the ACE methods, and their use thereof.

The ACE methods encompass all or part of these steps: (a) Make an ACE antigen by designing, synthesizing or isolating the ACE structure; (b) Make ACE antibody with the ACE antigen by any antibody-making, antibody-like molecule-making methods, and the like; (c) The ACE structure in sample preparations is not naturally or poorly accessible by antibody, and thus must be exposed artificially and precisely either in situ or ex situ by the designated hydrolytic enzyme or chemical agent treatment in a sequence-dependent and residue chemical bond-specific manner; and (d) Detect ACE in situ or ex situ by any antibody-based method in any types of sample preparations. This invention also includes utilities and applications of the ACE methods, antibodies, reagents, immunoassays and kits.

In one embodiment, this invention provides unique ACE antigen design methods, wherein the ACE structure must possess one or combinations of these characters: (a) must be antigenic, (b) must be a complete or truncated form of an artificially chemical bond-specific hydrolytic enzyme- or agent-cleaved segment (i.e., ACE); (c) either a branched conjugation site derived from both conjugation moieties, or a linear hidden antigen segment that is folded/buried inside its parent or surrounding macromolecule/structures; (d) must be artificially and specifically created and/or exposed in a sequence-dependent and residue chemical bond-specific manner in samples or sample preparations (e.g., in Western blot membranes, tissues or cell lysates, tissue sections, isolated or culture cells, isolated fractions, any ACE-containing surfaces/matrices/materials, and the likes); and (e) the hidden conjugation sites or linear hidden epitopes may be amino acids/peptides, sugar monomers/polymers, lipids/lipid linkers (e.g., ethanolamine), nucleic acids, ADP-ribose, or their combinations.

As mentioned, most macromolecule-to-macromolecule conjugation sites are hidden antigens. A general hidden macromolecule-to-macromolecule conjugation site-specific ACE structure is: Ln---L2-L1(-S1-S2---Sm)-L1'-L2'---Lm', wherein the ACE structure is a branched segment of an intact macromolecule-to-macromolecule conjugate composed of L and S oligomeric residue chains (e.g., peptides, saccharides, lipids, nucleic acids, ADP-ribosyls, or their conjugates); wherein S1 is covalently conjugated to L1 sidechain; wherein Ln, Lm', or Sm are continuously counted from L1, L1' or S1 residues; wherein Ln, Lm', or Sm are not free ends naturally, and have covalent chemical bonds with residues outside of the hidden ACE structure; and wherein said covalent chemical bonds must be artificially and specifically cleaved by specifically designed and chemical bond-specific hydrolysis in sample preparations to create and/or expose said hidden ACE structure for antibody detection.

The designs of hidden conjugation site-specific ACE structures of SUMO-to-protein, ubiquitin-to-protein, saccharide-to-protein, fatty acid-to-protein, GPI-to-protein, transglutaminase-mediated crosslink, and the like, are shown in FIGS. 1-8. By using the inventive ACE methods, we have successfully made several ACE antibodies that are highly specific to individual hidden macromolecule-to-macromolecule conjugation sites in biological samples including alpha-fetoprotein (AFP) core-fucosylation, ubiquitin-to-histon 2A K120, $Na^+/K^+$ ATPase, and ubiquitin-to-ubiquitin K48 conjugation site-specific antibodies, as shown in FIGS. 3, and 9-13.

In addition to macromolecular conjugation site, the inventive ACE methods can also be used to design and detect linear hidden antigens either in situ or ex situ in a sample preparation. An linear hidden ACE structure is "L1-L2------Ln" which is a hidden segment of an intact polymeric macromolecule (e.g., polypeptide, polysaccharide, lipid, nucleic acids, ADP-ribosyls, or their conjugates), wherein L1 and Ln are not free ends or terminals, and have covalent chemical bonds naturally or in vivo with residues outside of said ACE structure; and wherein said nature covalent chemical bonds can be artificially, specifically and precisely cleaved by designed chemical bond-specific hydrolysis in samples and sample preparations to create (the new terminals) and/or expose said hidden ACE structure for antibody detection.

In another embodiment, the invention provides methods of using ACE antigen to make antibodies including, but not limited to, polyclonal, monoclonal, bi-specific, recombinant, humanized, antibody-like molecules, and the like.

In a further embodiment, the invention provides methods of detecting ACE structures in samples and sample preparations, wherein ACE in a sample is poorly accessible or unrecognizable by antibodies, and thus must be artificially created (with new terminals) and/or exposed specifically and precisely, rather than randomly or accidentally, by residue chemical bond-specific hydrolytic enzymes or agents; wherein said hydrolytic enzymes and agents are specifically selected and should be mostly the same, but may also be occasionally different, with the one(s) used for the hydrolysis-guided ACE antigen design; wherein artificially, specifically and precisely creating (new terminals) and/or exposing hidden ACE antigens can be carried out in any samples or sample preparations including, but not limited to, in vivo or in vitro, in whole or part of biological bodies or organisms, in isolated organs or organelles, in tissues or tissue sections (with or without fixation), in isolated or cultured cells, in tissue or cell lysates, in body fluids or cell culture medium, as well as in biochemical assay mixtures, on Western blot or chromatographic membranes or any supporting matrices or surfaces, in chromatographic and centrifuge fractions, in cellular or subcellular fractions, and the likes. Examples are given below in FIGS. 1-13.

In additional embodiment, the inventive ACE methods can be used to reduce non-specific bindings in all antibody-based applications. This utility is owing to the fact that the chemical bond-specific hydrolysis is able to specifically and precisely create and/or expose the ACE structures, while breaking up other structures/epitopes that are otherwise able to bind to the ACE antibody non-specifically.

The inventive ACE methods, antibodies, reagents, immunoassays and kits can be used in all antibody-based applications, including, but not limited to, Western blot, immunocytochemistry, immunofluorescence, immunoelectron microscopy, immunoprecipitation, flow cytometry, Enzyme-Linked Immuno-Sorbent Assay (ELISA), peptide array, antibody array, or any other types of immunoassays, and the like.

The inventive ACE methods, antibodies, reagents, immunoassays and kits can be employed in a number of areas, including, but not limited to: (a) determination of specific conjugation sites and their sequences, (b) monitoring changes in molecule-to-molecule conjugation sites in vivo and in vitro, (c) diagnosis of diseases, (d) determination of molecular conjugation enzyme and chemical agent activities, (e) determination of molecular conjugation enzyme modulator or cofactor activities, (f) development of therapeutic agents for treatment of diseases, and (g) the like.

A few examples of diagnosing diseases with the ACE methods, antibodies, reagents, immunoassays, and kits may include, but are not limited to: (a) lysosomal storage diseases by assaying LC3II-related autophagy activities; (b) different types of cancers by assaying the cancer-specific core-fucosylated proteins; (c) neurological, neurodegenerative, and conformational diseases, as well as heart disease, muscle diseases (e.g., dermatomyositis), alcoholic liver disease, stroke and diabetes by assaying cell-, tissue-, or organ-specific or disease-specific macromolecule-to-macromolecule conjugation sites including, but not limited to, ubiquitin and ubiquitin-like conjugates, transglutaminase-mediated protein cross-links, telomeric aggregates, advanced glycation adducts, and the like; (d) diseases-related biomarkers, such as aberrant p53 ubiquitination-, sumoylation- and neddylation, and (e) the like.

The ACE methods, antibodies and reagents can be used in therapeutic applications including, but not limited to, those related to abnormal macromolecule-to-macromolecule conjugation.

The ACE methods, antibodies, reagents, immunoassays, and kits can be used in the area of biomaterials such as collagen-like biomaterials.

The ACE methods, antibodies, reagents, and immunoassays can be assembled to kits for research, diagnostic and therapeutic applications.

BRIEF DESCRIPTION OF THE DRAWINGS

All hidden antigens designed below are derived from the common structures of either linear L1-L2------Ln or branched Ln---L2-L1(-S1-S2---Sm)-L1'-L2'---Lm' ACE structures described above in the section (SUMMARY OF THE INVENTION). In exemplary ACE structures described in this invention, the single capital letters represent one-letter standard amino acid abbreviations. For instance, G=glycine, K=lysine, Q=glutamine, etc. The bold/italic (K) represents the conjugation site lysine. KLH all together is the abbreviation for Keyhole Limpet Hemocyanin, which is one of the most commonly used immunogenic carriers for antibody production. The dash "-" represents covalent chemical bond conjugation. The peptide sequence inside the brackets "( )" often represents the branched monomers or oligomers including, but not limited to amino acid(s)/peptide(s), lipid(s), saccharide(s), nucleic acid(s), and the likes.

The patent or application file contains at least one drawing executed in color. Copies of this patent or patent application publication with color drawing(s) will be provided by the Office upon request and payment of the necessary fee.

FIG. 1. A conjugation site-specific hidden antigen can be designed by the ACE methods in different ways depending on which hydrolytic enzyme(s) or agent(s) will be used for detection. The following are exemplary designs of SUMOto-protein conjugation site-specific hidden ACE antigens. Sequences in FIG. 1 are branched peptides, and no SEQ ID NOS are assigned to these branched sequences and other branched sequences throughout this application.

FIG. 1A: A GluC-cleaved ACE antigen is designed as GVK(GGTQQQFVDITDC-KLH)TE, and can be used to make the SUMO-to-SUMO K11 conjugation site-specific antibody. After treatment with GluC to artificially, specifically and precisely create and/or expose the GluC-cleaved ACE structure either in situ or ex situ in a sample, the SUMO-to-SUMO K11 conjugation sites can then be detected with the ACE antibody by all antibody-based methods.

FIG. 1B: A trypsin-cleaved ACE antigen is designed as EGVK(GGTQQQGGGC-KLH)TENN, and can be used to make the SUMO-to-SUMO K11 conjugation site-specific antibody. After treatment with trypsin to artificially, specifically and precisely create (new terminals) and/or expose the trypsin-cleaved ACE structure either in situ or ex situ in a sample, the SUMO-to-SUMO K11 conjugation site can then be detected with the ACE antibody by all antibody-based methods.

FIG. 1C: A GluC-cleaved ACE antigen is designed as KLH-CGGGALVAK(GGTQ)QE, and can be used to make the SUMO-to-NF-kappa-B essential modifier (NEMO) K277 conjugation site-specific antibody. After treatment with GluC to artificially, specifically and precisely create (new terminals) and/or expose the GluC-cleaved ACE structure either in situ or ex situ in a sample, the SUMO-to-NEMO conjugation site can then be detected with the ACE antibody by all antibody-based methods.

FIG. 1D: A GluC-cleaved ACE antigen is designed as RVK(GGTQQQGGGC-KLH)E and can be used to make the Sumo2/3-to-Heat shock factor protein 1 (HSF1) K298 conjugation site-specific antibody. After treatment with GluC to artificially, specifically and precisely create (new terminals) and/or expose the GluC-cleaved ACE structure either in situ or ex situ in a sample, the SUMO2/3-to-HSF1 K298 conjugation site can then be detected with the ACE antibody by all antibody-based methods.

FIG. 1E: A trypsin-cleaved ACE antigen is designed as LK(GGTQQQGGGC-KLH)K and can be used to make the Sumo2/3-to-Hypoxia-inducible factor 1 alpha (HIF1alpha) K391 conjugation site-specific antibody. After treatment with trypsin to artificially, specifically and precisely create (new terminals) and/or expose the trypsin-cleaved ACE structure either in situ or ex situ in a sample, the SUMO2/3-to-HIF1alpha K391 conjugation site can then be detected with the ACE antibody by all antibody-based methods.

FIG. 1F: A GluC-cleaved ACE antigen is designed as KLH-CGGGKLMFK(GGTQ)TE and can be used to make the Sumo1-to-p53 K386 conjugation site-specific antibody. After treatment with GluC to artificially, specifically and precisely create (new terminals) and/or expose the GluC-cleaved ACE structure in a sample, the SUMO1-to-p53 K386 conjugation site can then be detected with the ACE antibody by all immunological or antibody-based methods.

FIG. 2. Method 1a: A GluC-cleaved ACE antigen is designed as TFG-phosphotidylethanolamine (PE)-liposome and can be used to make the LC3II-specific antibody. The shaded area indicates the ACE structure. After treatment with GluC to artificially, specifically and precisely create and/or expose the GluC-cleaved ACE structure in a sample, the LC3II active form can then be specifically detected with the ACE antibody by all immunological methods. Method 1b illustrates how the TFG-PE ACE structure is artificially, specifically and precisely created and/or exposed by GluC treatment in a lipid membrane sample preparation.

FIG. 2. Method 2a: A GluC-cleaved ACE antigen is designed as TFGGGGC-KLH (SEQ ID NO: 14) and can be used to make the LC3II-specific antibody. After treatment with GluC to artificially, specifically and precisely create and/or expose the GluC-cleaved ACE structure in a sample, the LC3II active form can then be detected with the ACE antibody by all immunological or antibody-based methods.

FIG. 2. Method 2b: A cyanogen bromide (CNBr)-cleaved ACE antigen is designed as VYASQETFGC-KLH (SEQ ID NO: 15) and can be used to make the LC3II-specific antibody. After treatment with CNBr to artificially, specifically and precisely create and/or expose the CNBr-cleaved ACE structure in a sample, the LC3II active form can then be specifically detected with the ACE antibody by all antibody-based methods.

FIG. 2. Method 2c: A trypsin-cleaved ACE antigen is designed as KDEDGFLYMVYASQETFGC-KLH (SEQ ID NO: 16) and can be used to make the LC3II-specific antibody. After treatment with trypsin to artificially, specifically and precisely create and/or expose the trypsin-cleaved ACE structure in a sample, the LC3II active form can then be detected with the ACE antibody by all antibody-based methods.

FIG. 2. Method 3: A phospholipase D-cleaved ACE antigen is designed as KLH-CGGGSQETFG-ethanolamine (SEQ ID NO: 17) and can be used to make the LC3II-specific antibody. After treatment with phospholipase D to artificially, specifically and precisely create and/or expose the phospholipase D-cleaved ACE structure in a sample, the LC3II can be detected with the antibody by all immunological or antibody-based methods.

FIG. 2. Method 4: A phospholipase C-cleaved ACE antigen is designed as KLH-CGGGSQETFG-phosphoethanolamine (SEQ ID NO: 17) and can be used to make the LC3II-specific antibody. After treatment with phospholipase C to artificially, specifically and precisely create and/or expose the phospholipase C-cleaved ACE structure in a sample, the LC3II can then be specifically detected with the antibody by all immunological or antibody-based methods.

FIG. 3, Method 1: Two or more different glycoforms of the same protein backbone in a sample are digested with endo-beta-N-acetylglucosaminidase-D, F- and/or -H (Endo D/F/H) to artificially, specifically and precisely create and/or expose (monosaccharide) GlcNAc- and (disaccharide) Fuc-GlcNAc-glycoprotein hidden ACE structures. The hidden ACE structures can then be captured first with a surface precoated with an antibody to a non-glycan portion of the protein (antibody 1). The fluorophor-1-labeled GlcNAc-to-protein conjugation site-specific antibody (antibody 2), and/or the fluorophor-2-labeld Fuc-GlcNAc-to-protein conjugation site-specific antibody (antibody-3) can bind to their corresponding ACE structures captured on the surface. After washing, the fluorophors can be detected or imaged with a dual wavelength fluorometer.

FIG. 3, Method 2: Similarly, two or more different glycoproteins with the same core-fucosylated N-glycan, e.g., glycoproteins-1 and -2 in a sample, are digested with Endo D/F/H to artificially, specifically and precisely expose the ACE hidden structures. The Fuc-GlcNAc-proteins-1 and -2 in the samples are then captured with a surface precoated with the Fuc-GlcNAc-protein glycoform-specific ACE antibody. After washing, a fluorophor-1-labeled antibody against a non-glycan portion of glycoprotein-1, and/or fluorophor-2-labeled antibody against a non-glycan portion of glycoprotein-2, are then added to label the captured glycoproteins. After washing, the fluorophors can then be detected or imaged with a dual wavelength fluorometer.

FIG. 3, Method 3: N-glycan glycoproteins in a sample are digested with peptide:N-glycosidase F (PNGase F) which cleaves the chemical bond between the innermost GlcNAc and asparagine residue of the proteins. This digestion removes all of the N-glycans from the protein. The PNGase F-deglycosylated protein can still bind to the general antibody against the non-glycan portion of the protein, but cannot be recognized by the (monosaccharide) GlcNAc or (disaccharide) Fuc-GlcNAc glycoform-specific antibodies. This method can be used as a negative control of the glycoform-specific antibodies described above in Methods 1 and 2.

FIG. 3, Method 4: Western blot application of the glycoform-specific antibody. Samples from hepato-cellular carcinoma cell culture media were treated with non-enzyme solution (Ctr), a mixture of endo-D/H, or with the general PNGase-F (F), and then subjected to immunoblot analysis. Immunoblots were labeled with: (a) a general alpha-fetal protein (AFP) antibody, (b) the glycosylation site-specific antibody to disaccharide Fuc-GlcNAc (core-fucosylation) AFP, and (c) the glycosylation site-specific antibody to monosaccharide GlcNAc (no core-fucosylation) AFP. The general AFP antibody detects all glycosylated and de-glycosylated AFP bands (FIG. 3, Method 4a), the core-fucosylated site-specific AFP antibody labels only the core-fucosylated AFP (FIG. 3, Method 4b), and the monosaccharide GlcNAc site-specific AFP antibody labels only the GlcNAc-AFP (FIG. 3, Method 4c).

Figure 4:
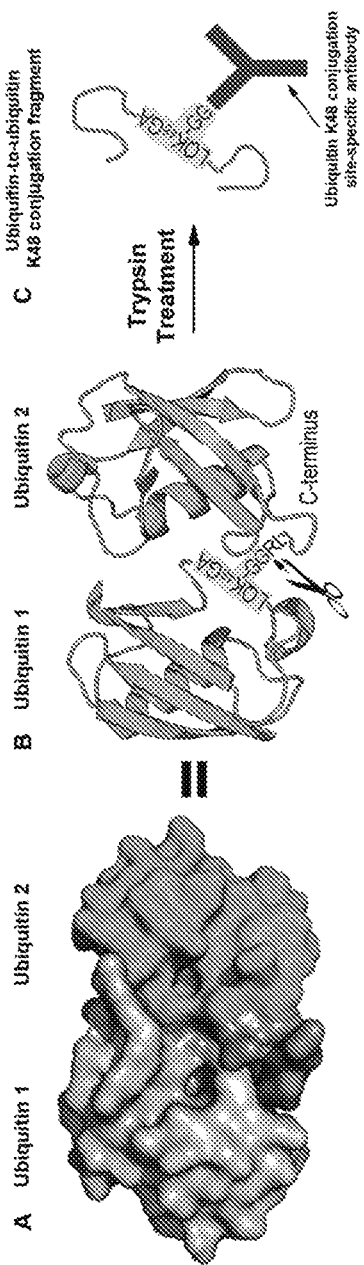

FIG. 4. Exemplary rationales for the ACE hidden antigen design. The ubiquitin-to-ubiquitin K48 conjugation site peptide LIFAGK$_{48}$(GG)QLEDGR is concealed inside the ubiquitin-to-ubiquitin conjugate structure (FIG. 4A). Furthermore, the conjugation site-specific ACE peptide LIFAGK$_{48}$(GG)QLEDGR within the intact K48 conjugate has no charged free terminals and thus is less antigenic (FIG. 4B). The trypsin treatment artificially, specifically and precisely: (i) creates three new antigenic free terminals, and (ii) opens up to expose the conjugation site-specific ACE structure LIFAGK$_{48}$(GG)QLEDGR, and thus makes this hidden epitope more antigenic and accessible to antibody (FIG. 4C).

FIG. 5: Trypsin-cleaved ACE hidden antigens: (A) ubiquitin-to-HIF1alpha; and (B) ubiquitin-to-histone 2A, are designed as KLH-CGGGMVNEFK(GG)LEL and LLPKK(GG)TESHHGGGC-KLH, respectively. These two antigens can be used to make the ubiquitin-to-HIF1alpha and ubiquitin-to-histone 2A conjugation site-specific antibodies, respectively. After treatment with trypsin to artificially, specifically and precisely create and/or expose the corresponding trypsin-cleaved hidden ACE structures in sample preparations, the ubiquitin-to-HIF1alpha and ubiquitin-to-histone 2A conjugation sites can then be detected with their corresponding ACE antibodies by all antibody-based methods.

FIG. 6. Trypsin-cleaved ACE hidden antigens are designed as: (1) KLH-CGGGAVVPC$_{133}$(palmitate)IK (SEQ ID NO. 3) for making the C133 palmitoylated caveolin-1 lipidation site-specific ACE antibodies; (2) liposome-Myristate-GSNK (SEQ ID NO. 4) for making p60c-src myristoylation site-specific ACE antibodies; (3) KLH-CGGGSGG$_{197}$(cholesterol)CF (SEQ ID NO. 5) for making the Hedgehog cholesterol-conjugation site-specific ACE antibodies; and (4) KLH-CGGGKC$_{186}$(farnesol)VLS (SEQ ID NO. 6) for making p21-Ras farnesylation conjugation site-specific ACE antibodies. After treatment with trypsin to artificially, specifically and precisely create and/or expose the corresponding trypsin-cleaved hidden ACE structures in sample preparations, the lipidation-specific ACE structures can then be detected with their corresponding ACE antibodies, respectively, by all antibody-based methods. Similarly, (also in FIG. 6) a LysN-cleaved or peptidyl-Lys metalloendopeptidase-cleaved hidden ACE antigen is designed as KLH-CGGGKC$_{189}$(geranylgeranyl isoprene)LLL (SEQ ID NO. 7) for making p21-Rac1 (ras-related C3 botulinum toxin substrate 1) geranylgeranylation conjugation site-specific antibodies. After treatment with LysN or peptidyl-Lys metalloendopeptidase to artificially, specifically and precisely create and/or expose the ACE structure in sample preparations, the geranylgeranylated p21-Rac1 conjugation site can then be specifically detected with the antibodies by all antibody-based methods.

FIG. 7. Two trypsin-cleaved ACE hidden antigens are designed as: (1) GC-phosphoethanolamine-SGGGC-KLH (SEQ ID NO: 8); and (2) TS-phosphoethanolamine-SGGGC-KLH (SEQ ID NO: 9) for making the glycosylphosphatidylinositol (GPI)-to-prion protein (PrP), and GPI-to-glypican, conjugation site-specific antibodies, respectively. After treatment with trypsin to artificially, specifically and precisely create and/or expose the trypsin-cleaved ACE structures in samples or sample preparations, the PrP-to-GPI or glypican-to-GPI conjugation sites can then be detected, respectively, with their corresponding ACE antibodies by all antibody-based methods.

FIG. 8. A trypsin-cleaved ACE antigen is designed as KLH-CGGGQK(DQLGK)TV (SEQ ID NOS: 10-11) for making the transglutaminase-mediated synuclein-to-synuclein conjugation site-specific antibodies. After treatment with trypsin to artificially, specifically and precisely create and/or expose the trypsin-cleaved hidden ACE structure in samples or sample preparations, the synuclein-to-synuclein conjugation site can then be detected with this ACE antibody by all antibody-based methods.

FIG. 9. Immunohistochemistry labeling of the ubiquitin-to-ubiquitin K48 conjugation site-specific ACE structure in tissue sections. Tissue sections were treated without (FIG. 9A) or with (FIG. 9B) trypsin, and then double-labeled with the ubiquitin-to-ubiquitin K48 ACE antibody and propidium iodide (PI). PI stains nuclei in a red color, while the ubiquitin-to-ubiquitin K48 conjugation site-specific antibody-labeled conjugation site is shown in a green color. In FIG. 9A, without trypsin treatment, the hidden ubiquitin K48 conjugation site ACE structure was not artificially, specifically and precisely created and/or exposed, and thus could not be labeled with the K48 ACE antibody in the green color. In comparison, in FIG. 9B, because the hidden ubiquitin K48 conjugation site ACE structure were exposed artificially and specifically by trypsin treatment, the ubiquitin K48 conjugation site-specific antibody labeled the hidden ACE structure in the green color. PI-stained nucleic acids in the red color were not affected by trypsin treatment, and thus are seen in both trypsin-treated and -untreated tissue sections.

FIG. 10. Immunoblots of the ubiquitin-to-ubiquitin K48 ACE structure on Western blot membranes. Equal volumes of tissue lysates with equalized protein concentration were subjected to Western blot analysis. The Western blot membranes were treated either with (FIG. 10A) or without (FIG. 10B) trypsin. A: The ubiquitin-to-ubiquitin K48 conjugation site ACE structure was labeled with the conjugation site-specific antibody because the hidden ACE structure was artificially, specifically and precisely created and/or exposed with trypsin treatment. B: The hidden ubiquitin-to-ubiquitin K48 conjugation site ACE structure was not labeled with the ACE antibody because, without trypsin treatment, the hidden conjugation site ACE structure remained hidden, and thus was not artificially, specifically and precisely created and/or exposed on Western blot membrane.

Figure 11:
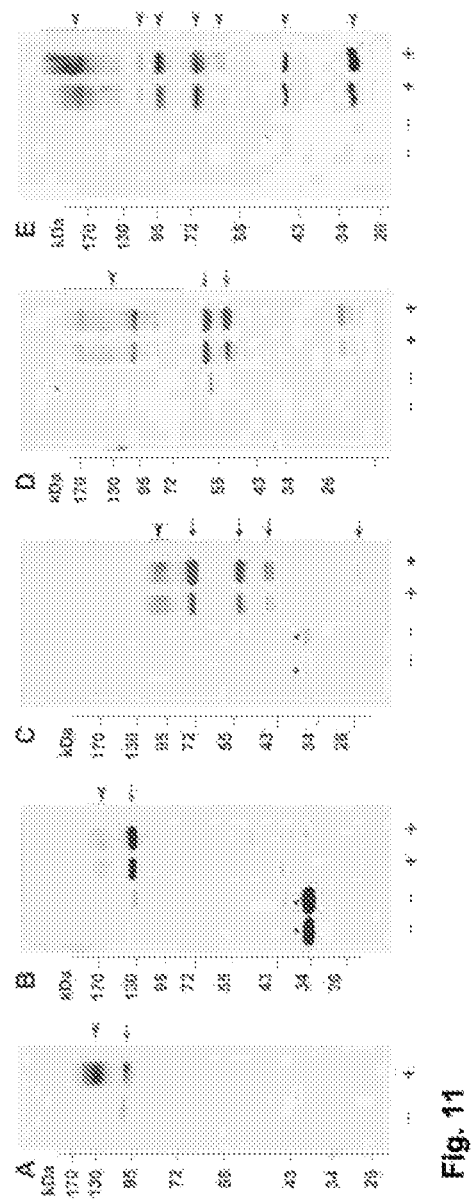

FIG. 11. Immunoblots of hidden ACE antigen designs and detections. Equal protein concentrations and volumes of tissue lysates were subjected to Western blot analysis. The Western blot membranes were treated either without (−) or with (+) trypsin (FIG. 1A-D), or GluC (FIG. 1E). According to the ACE methods, the selection of either trypsin or GluC in this situation must be based on the protease information used for the ACE antigen design. The ubiquitin-to-protein conjugation site ACE structures were designed as CIMESFK(GG)NMVPQQALVIR for $Na^+/K^+$ ATPase or ATP1A1 (FIG. 1A); CHLNK(GG)MQNHGYENPTYK for Amyloid beta precursor-like protein 2 or Aplp2 (FIG. 1B); CLHED-PPQK(GG)PPR for amyloid beta protein precursor intracellular domain associated protein-1b or AIDA-1b (FIG. 1C); and CYQLFEELGK(GG)GAFSVVR (K21) for calcium/calmodulin dependent kinase II or CaMKII (FIG. 1D). These are trypsin-digested segments or their truncated forms. The SUMO2/3-to-protein conjugation ACE structure was designed as CGGKPKEGVK(GGTQQQ)TE (FIG. 1E), which is a GluC-digested segment. Without trypsin or GluC treatment (−), the specific protein bands were hidden and thus could not be or poorly detected with their corresponding antibodies. In contrast, after trypsin or GluC treatment (+) to artificially, specifically and precisely create and/or expose the ACE structures, both the conjugated (arrowheads), and non-conjugated protein hidden bands (arrows) can be detected with their corresponding antibodies. * indicates the nonspecific bands because their molecular sizes do not match with the proteins of interests.

Figure 12:
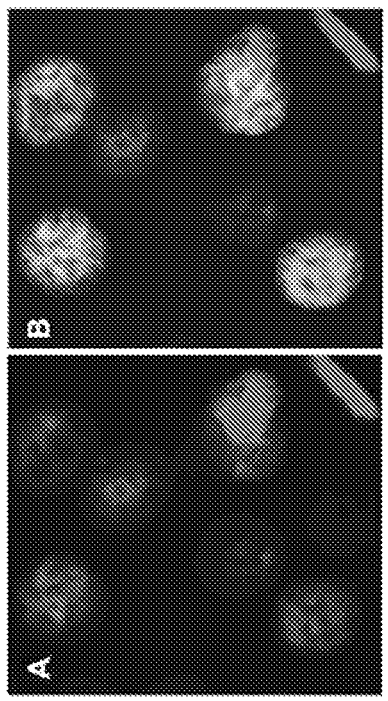

FIG. 12. Immunohistochemistry of tissue sections double-stained with the ubiquitin-to-histone K120 conjugation site-specific ACE antibody (green) and PI (red). Tissue sections were treated without (A) or with (B) trypsin. A: Without trypsin treatment, the hidden ubiquitin-to-histone K120 ACE structure was not artificially, specifically and precisely created and/or exposed. Therefore, only PI-stained nuclei in the red color are seen. B: Both PI-stained red nuclei, and the ubiquitin-to-histone K120 conjugation site-specific antibody-labeled green ACE structure are seen, because the hidden K120 ACE structure was artificially, specifically and precisely created and/or exposed by trypsin treatment.

Figure 13:
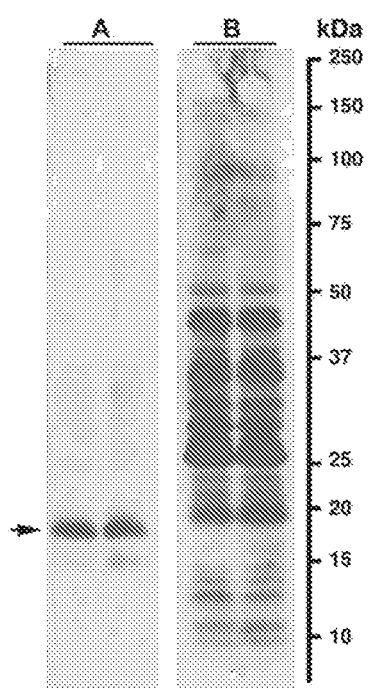

FIG. 13. Immunoblots of the ubiquitin-to-histone K120 conjugation site. Western blot membranes were treated either with trypsin (A) or with the buffer only (B, no trypsin). After washing, membranes were labeled with the ubiquitin-to-histone K120 conjugation site-specific rabbit crude antiserum. After washing, membranes were labeled with a peroxidase-labeled secondary antibody and developed with an enhanced chemiluminescence (ECL) Western blot system. A: The hidden ubiquitin-to-histone conjugation site ACE structure was specifically labeled with the conjugation site-specific antiserum because the hidden ACE structure was artificially, specifically and precisely created and/or exposed with trypsin treatment. Arrow indicates the monoubiquitin-to-histone band. B: The hidden ubiquitin-to-histone conjugation site ACE structure was not labeled with the antiserum because, without trypsin treatment, the hidden ACE structure was not artificially, specifically and precisely created and/or exposed. Therefore, the antiserum-labeled bands on Western blot membrane are likely non-specific bindings.

Figure 14:
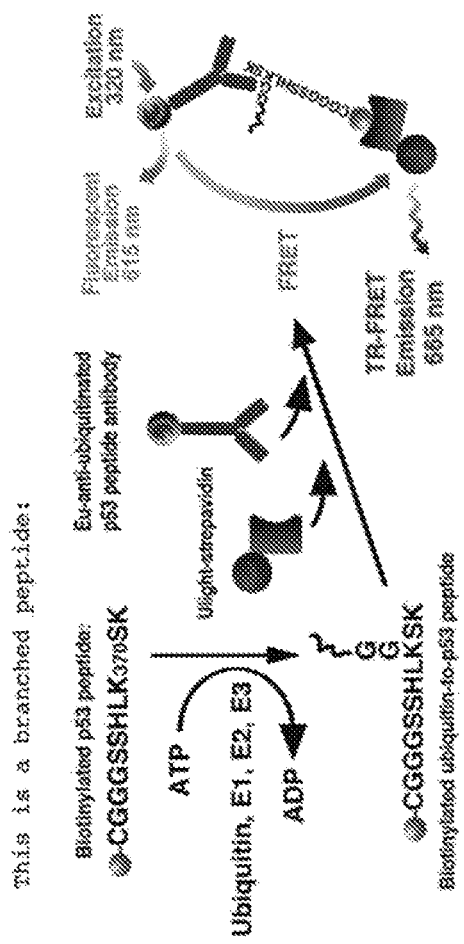

FIG. 14. An antibody-based time-resolved fluorescence resonance energy transfer (TR-FRET) assay design. The human double minute (Hdm2) oncogene E3 ubiquitin ligase catalyzes ubiquitination of p53 at a lysine residue K370. The conjugation site-specific antibody to the ubiquitin-to-p53 K370 site can be made with KLH-CGGGSSHLK$_{370}$(GG)SK) (no SEQ ID NO is assigned to this branched sequence). The assay mixture consists of a biotinylated p53 peptide substrate (biotin-CGGGSSHLKSK), Hdm2, ATP, K48R ubiquitin, E1, and E2 (UbcH5c). After incubation, a stop buffer (e.g., 40 mM EDTA) containing detection mix (ULight-streptavidin and the Europium Cryptate-labeled ubiquitin-to-p53 conjugation site-specific antibody) is then added. The p53 E3 ligase activity can then be measured with a time-resolved fluorometer at excitation of 320 nm and emission 665 nm.

FIG. 15. A-B: Examples of Protein Glycosylation Conjugation Site-Specific ACE Structures. In the following sequences, the ACE structure with branch (GlcNAc or Fuc-alpha1,6-GlcNAc) conjugation is created in a sample preparation by endoglycosidases treatment. In this case, only the polysaccharide chain is cleaved, while the protein polypeptide chain is not cleaved. In the hidden antigen case, however, the sample preparation also needs to be treated with the designated hydrolytic enzyme or hydrolytic agent in order to create and/or expose the hidden antigen for antibody detection.

FIG. 15A. Protein Glycosylation Sequence ID NOS: 1 and 18-28.

FIG. 15B. Protein Glycosylation Sequence ID NOS: 29-39.

FIG. 16. A-E: Examples of Protein Sumoylation Conjugation Site-Specific ACE Structures. In the following sequences, the branch structure (GGTQ) is derived from any isoform of SUMO proteins including, but not limited to, SUMO1 and SUMO2/3. The ACE structure with an E (=glutamate) residue at the C-terminal is created in a sample preparation by GluC treatment, whereas the ACE structure with the C-terminal K (=lysine) or R (=arginine) residue is created by trypsin treatment. There is an exception in the situations that there is no E, K or R residue between the conjugation site and the protein C-terminal.

FIG. 16A. Part A of Sumoylation Conjugation Site-Specific ACE Structures.

FIG. 16B. Part B of Sumoylation Conjugation Site-Specific ACE Structures.

FIG. 16C. Part C of Sumoylation Conjugation Site-Specific ACE Structures.

FIG. 16D. Part D of Sumoylation Conjugation Site-Specific ACE Structures.

FIG. 16E. Part E of Sumoylation Conjugation Site-Specific ACE Structures.

FIG. 17. A-D: Examples of Protein Ubiquitination Conjugation Site-Specific ACE structures. In the following sequences, the ACE structure with branch (GG) conjugation is created in a sample preparation by trypsin treatment, so that the C-terminal is either a K (=lysine) or R (=arginine) residue. The ACE structure with branch (GGRLRLVL-HLTS) conjugation is created by GluC treatment, and, as a result, the C-terminal is E (=glutamate). There is an exception in the situations that there is no E, K or R residue between the conjugation site and the protein C-terminal, or that the sequence between the conjugation site and the next E, K or R residue is too long to expose the hidden antigen.

FIG. 17A. Part A of Ubiquitination Conjugation Site-Specific ACE structures.

FIG. 17B. Part B of Ubiquitination Conjugation Site-Specific ACE structures.

FIG. 17C. Part C of Ubiquitination Conjugation Site-Specific ACE structures.

FIG. 17D. Part D of Ubiquitination Conjugation Site-Specific ACE structures.

FIG. 18. Examples of Protein Neddylation Conjugation Site-Specific ACE Structures. In the following sequences, the ACE structure with branch (GG) conjugation is created in a sample preparation by trypsin treatment, so that the C-terminal is either a K (=lysine) or R (=arginine) residue. The ACE structure with branch (GGRLRLVLHLTS) conjugation is created by GluC treatment, and, as a result, the C-terminal is E (=glutamate). There is an exception in the situations that there is no E, K or R residue between the conjugation site and the protein C-terminal.

FIG. 19. SEQ ID NOS 40-53 are examples of Linear Hidden ACE Structures. In the following sequences, the linear hidden ACE structures are protein-to-protein non-covalent binding sites with the common hydrophobic motif (as indicated with bold/italic letters) or hidden and thus poorly accessible to antibody. They are either Asp-N Endopeptidase (the N-terminal E), or trypsin (with the terminal K or R), or GluC (with the terminal E) cleaved protein segments.

Figure 20:
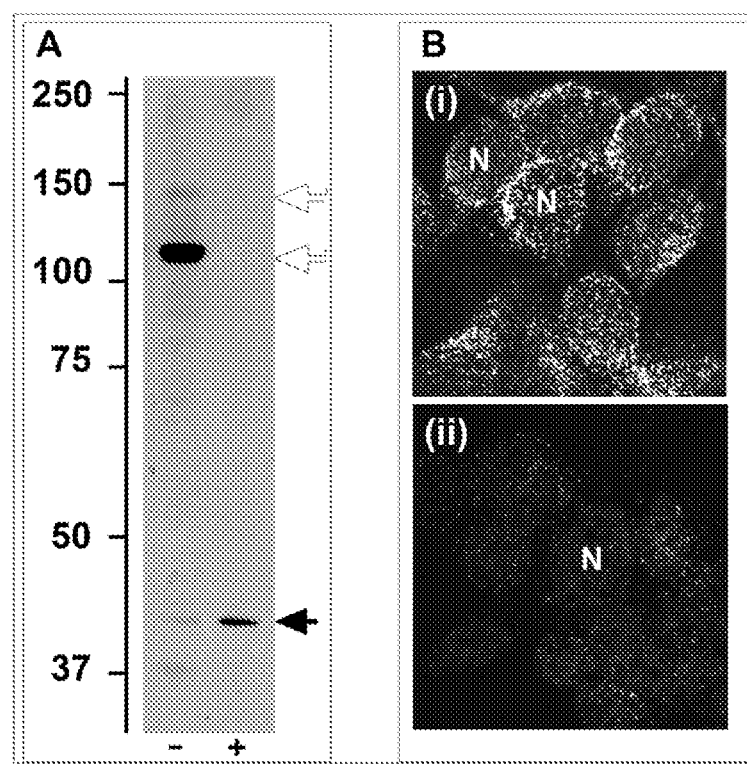

FIG. 20. Example of detecting the hidden linear ACE structure. A: Western blot analysis of the ACE structure. The same cell lysates were loaded to lanes 1 and 2, respectively, and then subjected to Western blot analysis. The Western blot membranes were treated either with (+) or without (−) Asp-N Endopeptidase, and then labeled with the corresponding ACE antibody. Filled arrows point to the protein band with the ACE structure; and open arrows indicate the non-specific binding. The hydrolytic treatment removed the non-specific labeling but markedly increased the antibody specific labeling, as the ACE structure is Asp-N Endopeptidase-resistant. B: The cells were treated with (i) or without (ii) Asp-N Endopeptidase and then immunocytochemically labeled with the corresponding ACE antibody. With the hydrolytic treatment (i) to create or expose the hidden ACE structure, the ACE antibody could access and thus label the ACE structure. Without the hydrolytic treatment (ii), the ACE antibody was pooly accessible to and thus poorly label the hidden ACE structure. N=nucleus.

DETAILED DESCRIPTION

The invention summarized above may be better understood by referring to the following description, which should be read in conjunction with the accompanying claims and drawings in which like reference numbers are used for like parts. This description in which some examples of the embodiments of the inventions are shown, is to enable one to build and use an implementation of the invention, and is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent methods, designs, constructs, antibodies, kits, samples, and cell lines do not depart from the spirit and scope of the invention in its broadest form.

DEFINITIONS

As used herein, the term "detection" or "detecting" is interchangeable with discovering, uncovering, finding, recognizing, revealing, determining, examining, measuring, and the like.

As used herein, "in situ" refers to a phenomenon or event occurred in exactly the original location, both in vivo and in vitro, including but not limited to, in whole or part of biological bodies or organisms, in isolated organs, cells, and organelles, in tissues or tissue sections (with or without fixation), in isolated or cultured cells, in body fluids or cell culture media, as well as on Western blot membranes, and any supporting matrices or surfaces, in chromatographic and centrifuge fractions, in reaction mixtures, and the like.

As used herein, "ex situ" is the opposite of "in situ", and refers to a phenomenon or event that does not occur in the original place both in vivo and in vitro.

As used herein, the term "hidden antigen" is often interchangeable with "hidden hapten or segment" or "ACE structure", and refers to an antigen epitope/segment/structure that, in its intact or natural form, is less antigenic and/or poorly accessible to large molecules including, but not limited to, antibodies. For example, an ACE structure may be a macromolecule-to-macromolecule conjugation site, or a segment normally located inside its parent macromolecule, or may be covered by other surrounding molecules/structure(s)/cell membranes either in situ or ex situ, and thus is poorly or not accessible to antibodies.

As used herein, the term "macromolecule" refers to a polymeric molecule with more than 2 same or different units, either in a linear or branched sequence, including, but not limited to, polypeptides, polysaccharides, lipids or phospholipids, and nucleic acids, poly(ADP-ribose), or any combinations of the above.

As used herein, the term "macromolecule-to-macromolecule conjugation" refers to that process in which one macromolecule conjugates to another same or different macromolecule via a covalent linkage.

As used herein, the term "carbohydrate" is interchangeable with the term "saccharide", typically referring to either polymeric or monomeric sugar molecules.

As used herein, the term "conjugation site" refers to the site where a covalent linkage is formed between two macromolecules, mostly terminal-to-sidechain branched conjugations, and occasionally molecular head-to-tail linear conjugations.

As used herein, the term "conjugation site-specific hapten" refers to a segment that contains a macromolecular conjugation site, which may need to be linked to an immunogenic carrier in order to become a complete antigen.

As used herein, the term "conjugation site-specific antibody" refers to antibody that can specifically recognize a macromolecular-to-macromolecular conjugation site derived from both macromolecular moieties.

As used herein, the term "sidechain" refers to a chemical group that is attached to or branches from a core part of the molecule called the "mainchain" or backbone. In polymers, side chains extend from a backbone structure.

As used herein, the term "hydrolytic enzyme" refers to proteases, glycosidases, lipases or phospholipases, nucleases, and the like, which are currently known or will be identified in the future and are capable of cleaving particular chemical bonds in macromolecules in a site-specific manner.

As used herein, the term "agent", may be interchangeable with "hydrolytic agent" or "chemical agent", and refers to chemicals or any other non-biological materials that are currently known or will be identified in the future, and are capable of cleaving particular chemical bonds in macromolecular backbones in a site-specific manner. Hydrolytic agents may include, but are not limited to, 2-nitro-5-thiocyanobenzoic acid (NTCB) +Ni that cleaves the peptide bond at cysteine loci (Degani and Patchornik, 1974); cyanogen bromide (CNBr) that cleaves at methionine loci; BNPS-skatole [2-(2-nitrophenylsulfenyl)-3-methylindole] that cleaves at tryptophan loci; and formic acid that cleaves at aspartate loci in protein backbones.

Hydrolytic proteases and agents include, but are not limited to, Arg-C proteinase, Asp-N endopeptidase, Asp-N endopeptidase+N-terminal Glu, BNPS-Skatole, caspase1, caspase2, caspase3, caspase4, caspase5, caspase6, caspase7, caspase8, caspase9, caspase10, chymotrypsin, clostripain (clostridiopeptidase B), CNBr, enterokinase, factor Xa, formic acid, glutamyl endopeptidase, granzymeB, hydroxylamine, iodosobenzoic acid, LysC, LysN, NTCB (2-nitro-5-thiocyanobenzoic acid), pepsin, proline-endopeptidase, proteinase K, staphylococcal peptidase I, tobacco etch virus protease, thermolysin, thrombin, trypsin, and the like.

The chemical bond-cleaving site specificities of hydrolytic enzymes or agents can be found in publicly accessible databases including, but not limited, to Swiss-Prot ExPASy and the National Center for Biotechnology Information.

Glycosidases include, but are not limited to, exoglycosylase, endoglycosylase, any combination of exoglycosylase and endoglycosylase, and/or sialidase, fucosidase, mannosidase, galactosidase, xylosidase, and the like.

Lipases include, but are not limited to, triglyceride lipase, pancreatic lipase, lysosomal lipase, hepatic lipase, hormone-sensitive lipase, endothelial lipase, lingual lipase, and the like.

Phospholipases include, but are not limited to, phospholipase A1, phospholipase A2, phospholipase B, phospholipase C, phospholipase D, GPI-phospholipase C, GPI-phospholipase D, and the like.

Macromolecular conjugation enzymes include but are not limited to E3 ubiquitin-protein ligase; UBL ligase, carbohydrate transferase, poly (ADP-ribose) polymerase, fatty acyl transferase; autophagy-related protein ligase [e.g., autophagy-related gene (ATG) 3 and ATG10], sumoylation ligase, neddylation ligase, transglutaminase, and the like.

Macromolecular de-conjugation enzymes may include, but are not limited to, deubiquitination enzymes (DUBs) and UBL proteases; desumoylation enzymes or SUMO proteases; deglycosylation enzymes, lipases, phospholipases, poly (ADP-ribose) glycohydrolases (PARG), and the like.

Enzymes used in the invention may be natural, recombinant or chemically synthesized. They may be substantially pure, partially purified, or present in a crude biological sample.

As used herein, the term "organism" refers to all cellular life-forms including, but not limited to, prokaryotes and eukaryotes, non-cellular life-forms, and nucleic acid-containing entities including, but not limited to, bacteriophages and viruses.

As used herein, the term "sample or sample preparation" refers to a collection of inorganic, organic or biochemical molecules either in a pure or mixture form, either in nature (e.g., in a biological- or other specimen) or artificial type, either in heterogeneous or homogeneous form, either in isolated, partially isolated or non-isolated form, or either in solution or in a form immobilized or semi-immobilized on any supporting materials including but not limited to electrophoresis matrix (e.g., gel or capillary), Western blot membrane (e.g., nitrocellulose membranes), agarose support (e.g., gel or bead), nano particles, any supporting surface, cell culture plates, multiplex beads, or chromatographic supporting matrix, sucrose gradient medium. "Sample" further refers to a biological sample.

As used herein, the term "organism" refers to all cellular life-forms, including but not limited to prokaryotes and eukaryotes, as well as non-cellular life-forms, nucleic acid-containing entities, including but not limited to bacteriophage and viruses.

As used herein, the terms "biological sample" refer to a collection of a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate, subcellular fraction or extract prepared from a whole organism or a subset of its tissues, cells or component parts, or a portion thereof. "Biological sample" also refers to sample preparations including but not limited to on electrophoretic and chromatographic gels, on Western, Southern, and Northern blot membranes, in isolated organelles, and in separated fractions.

As used herein, the term "tissue section" refers to a thin slice prepared from a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen).

As used herein, the term "conjugation site-specific antibody" further refers to one or more antibodies, and also referred to as immunoglobulins. Conjugation site-specific antibody may be natural or partially or wholly produced artificially, e.g. recombinant, or antibody fragments. A conjugation site-specific antibody may be monoclonal or polyclonal, humanized, bispecific, and heteroconjugate antibodies, as well as antibody-like binding partners (e.g., phage display antibody-like fusion protein). Conjugation site-specific antibody may be made in all immunoreactive animals or organisms including but not limited to rabbit, rat, mouse, sheep, horse and donkey. The antibody may, in some cases, be a member of one, or a combination immunoglobulin classes, including: IgG, IgM, IgA, IgD, and IgE, as well as antibody-like molecules.

As used herein, the term "de-conjugation site-specific antibody" refers to one or more antibodies that recognize the conjugation site in the non-conjugated form.

As used herein, the term "pan antibody" refers to one or more antibodies that recognize epitopes that are not located on the conjugation site.

The conjugation site-specific haptens or antigens may be used to select its binding partners by, for example, phage display or yeast display. The haptens or antigens include, but are not limited to, any chemical monomers or polymers, amino acids or peptides, carbohydrates, lipids or phospholipids, nucleotides, poly (ADP-riboses), and the like.

As used herein, the term "antigenicity' refers to the antigen capacity to stimulate the production of antibodies and the capacity to react with antibodies.

As used herein, the term "primary antibody" refers to antibody raised against an epitope of interest. The epitope can be a protein, peptide, carbohydrate, lipid, phospholipid, nucleic acid, any combination of the above, or any other macromolecules.

As used herein, the term "secondary antibody" refers to an antibody that binds to primary antibodies or antibody fragments. They are typically labeled with measurable probes for detection, purification, or cell sorting applications.

As used herein, the term "immunoassay" refers to any antibody-based measurement of the content of any substance in a sample. The presence of antigen and/or antibody can be assayed. The most common method is to label either antigen or antibody with any suitably detectable materials including, but not limited to, enzymes, radioisotopes, magnetic or fluorescent labels, or nanoparticles.

As used herein, the term "Western blot" or its interchangeable term "immunoblot" refers to an analytical method for detection of proteins or modified proteins in a sample. It uses gel electrophoresis to separate molecules in a sample. The separated molecules are then transferred to a membrane (typically nitrocellulose) that can hold the macromolecules, where such macromolecules of interest can be detected specifically with antibodies.

As used herein, the term "Enzyme-Linked ImmunoSorbent Assay" or "ELISA" refers to any method of detecting the presence and level of an antibody or an antigen in a sample. There are several variants of ELISA, including, but not limited to, sandwich ELISA, competitive ELISA, indirect ELISA, ELISA Reverse and the like. The most common procedure is to coat an antibody or antigen onto a surface, and then to add molecules of interest (antigen or antibody) to the precoated surface so that an antibody to antigen complex can form. The tagged antibodies or antigens, or the added secondary antibody with a detectable tag, can then be detected with a readout system.

As used herein, the term "immunohistochemistry" commonly refers to a method of antibody-based localization of antigens in a sample, commonly in a tissue section. An antibody to antigen interaction can be visualized by microscopy at the cellular level via any detectable means including, but not limited to, antibodies tagged by fluorophors, chromospheres or luminescence, or any detectable tags with any combinations of the above, including, but not limited to, peroxidase and its variants, chemiluminescence and its variants, and fluorescent molecules such as fluorescein isothiocyanate (FITC), Texas Red, rhodamine (TRITC), coumarin, cyanine, Alexa Fluors and the DyLight Fluors, and their derivatives.

As used herein, the term "immunocytochemistry" is often interchangeable with immunohistochemistry. Immunocytochemistry emphasizes a method of using antibodies to detect specific antigens at the cellular level. Immunocytochemistry may differ somewhat from immunohistochemistry in that it is often performed on samples of intact cells, whereas immunohistochemical samples are usually on tissue sections.

As used herein, the term "immunoprecipitation" refers to a technique of antibody precipitating its antigen molecule out of mixture samples. This process is often used to isolate and concentrate a particular antigen or antigen complex from other molecules in a sample. Immunoprecipitation often requires coupling antibody-antigen complexes to a solid support substance in the procedure for separation of antibody-antigen complexes from other molecules in a sample.

As used herein, the term "co-immunoprecipitation" refers to immunoprecipitation of intact antigen complexes.

As used herein, the term "flow cytometry" refers to a method of counting, examining, and sorting particles suspended in a stream of fluid. It allows simultaneous multiparametric analysis of the physical and/or chemical characteristics of single cellular particles flowing through an optical and/or electronic detection apparatus.

"Post-translational modification" refers to any chemical modification of a polypeptide chain during and after it is synthesized, including but not limited to phosphorylation, acylation, acetylation, methylation, sulfonation, glycosylation, lipidation, prenylation, isoprenylation, ubiquitination, biotinylation, formylation, citrullination, myristoylation, sumoylation, gamma carboxylation, ADP-ribosylation, amidation, covalent attachment of a moiety including but not limited to flavin, heme, nucleotide or nucleotide derivative, phosphotidylinositol, cyclization, demethylation, formation of covalent cross-links including but not limited to transglutaminase-mediated protein cross-linking, formation of pyroglutamate, GPI anchor formation, hydroxylation, iodination, oxidation, proteolysis processing, racemization, selenoylation, and the like. A post-translational modification may also involve cleavage of the polypeptide chain, proteolytic processing, the formation of disulfide bonds, and the like.

As used herein, the term "glycosylation" refers to the enzymatic or non-enzymatic process that links at least one saccharide moiety to proteins, lipids or other macromolecules. The majority of proteins synthesized in the rough endoplasmic reticulum (ER) undergo glycosylation. Glycosylation also occurs in the cytoplasm and nucleus including, but not limited to, the O-GlcNAc (N-acetylglucosamine) modification. Cells can produce several classes of glycans including, but not limited to: N-linked glycan attached to the amide nitrogen of asparagine sidechain of a polypeptide; O-linked glycan attached to the hydroxyl oxygen of serine and threonine sidechain of a polypeptide; glycosaminoglycans attached to the hydroxyl oxygen of serine in a polypeptide; glycolipids in which glycans are attached to ceramide and hyaluronan, and GPI anchors which link proteins to lipids via glycan linkages.

"Core fucosylation" refers to the linkage of a fucose residue to the core N-acetylglucosamine via alpha1-6 linkage. All N-linked glycan structures have a common structure, referred to as the core, containing three mannose and two N-acetylglucosamine residues.

As used herein, the term "glycoform" refers to a group of proteins having an identical backbone amino acid sequence but different carbohydrate moieties.

As used herein, "artificially cleaved epitope or ACE" refers to an epitope that is artificially cleaved for creating more antigenic and accessible epitope to antibody for detection or forming antibody-to-ACE complex purpose.

The "Artificially Cleaved Epitope" or "ACE" does not include naturally cleaved antigens in vivo.

As used herein, "hydrolysis-guided ACE design or ACE design" refers to antigen design methods that use an artificially cleaved epitope (ACE) as a hapten or antigen. The ACE is not naturally accessible to antibody or antibody-like molecules but can be artificially, specifically and precisely created and/or exposed in a sample by the chemical bond-specific hydrolysis of macromolecules.

As used herein, "hydrolysis-guided ACE antibody production" is interchangeable with "ACE antibody production" refers to making antibody with an ACE hapten or antigen designed by the ACE design methods.

As used herein, "residue" and "monomer" (of macromolecules) is often interchangeable, refers to a specific unit within polymeric chains of peptides, polysaccharides, lipids, nucleic acids, poly(ADP-ribose), and the like.

As used herein, "create or expose" (of ACE antigen) is often interchangeable.

As used herein, the term "create" refers to artificially creating ACE structures with free terminals in samples or sample preparations for antibody detection.

As used herein, "ACE methods" refers to a group of collective techniques including, but not limited to: (i) ACE design, (ii) making ACE antibody, (iii) ACE exposure and detection either in situ or ex situ in a sample, and (iv) ACE method applications. The ACE methods require to use: (a) structural and sequence information of molecular conjugates or linear hidden antigen, (b) chemical bond-cleaving specificities and properties of hydrolytic enzymes and agents, and (c) ACE exposure and detection methods.

1. Methods of Design Ace Antigens

Extensive efforts on generation of macromolecule-to-macromolecule conjugation site-specific antibodies by conventional antibody methods have been proven futile (Matsumoto et al., 2008). Our recent study suggests that these unsuccessful attempts are mainly because most macromolecule-to-macromolecule conjugation sites are either poor antigen or hidden on the inside of the conjugated macromolecules, and thus poorly or not accessible to antibody binding (see FIG. 4 as a example). This invention provides novel methods to solve these problems. These methods are generally and collectively referred to as the "hydrolysis-guided ACE methods" or simply "ACE methods", including, but not limited to, all or part of these steps: (i) selecting a specific hydrolytic enzyme or chemical agent-cleaved conjugation site-specific or a hidden ACE sequence or its truncated form; (ii) the ACE structure is a non-cleaved segment of an intact macromolecule in vivo, and is either poorly antigenic, or inaccessible by antibody, but can be artificially, specifically and precisely created and/or exposed by the residue chemical bond-specific hydrolytic enzyme, agent or their combinations, (iii) conjugate the ACE hapten to an immunogenic carrier for making it a complete antigen, (iv) a spacer including but not limited to GGG (glycine-glycine-glycine) may sometimes be added to increase the flexibility of the ACE, (v) use the complete antigen to make the antibodies or antibody-like molecules or binding partners, (vi) remove antibodies to non-conjugation site by negative absorption with the non-conjugated linear peptide(s), (vii) create and/or expose the ACE artificially, specifically and precisely, rather than randomly or accidentally, either in situ or ex situ in any sample preparations by the specifically designated chemical bond-specific hydrolytic enzyme or means, and (viii) detect or image the ACE structure in sample preparations by antibody-based methods.

Comprehensive information about macromolecule-to-macromolecule conjugation sequence structures, and residue chemical bond-specific hydrolytic enzymes and chemical agents, can be found in the literature and publically accessible databases including but not limited to National Center for Biotechnology Information at www.ncbi.nlm.nih.gov/ and ExPASy at www.expasy.ch/.

1.1. Macromolecular Conjugation Site-Specific ACE Structure Design.

The ACE methods for designing an ACE structure are based on information of: (a) the molecular structure and ACE sequence, (b) availability and property of chemical bond-specific hydrolytic enzymes or agents, and (c) methods of sample analyses (see FIGS. 1-14). Therefore, the ACE methods are highly predictable, reliable and sensitive, as demonstrated in FIGS. 1-14. Generally, the ACE structure at a hidden macromolecule-to-macromolecule conjugation site has all or part of these characters: (i) comprises of a shorter piece (usually 1-6 monomers) derived from one macromolecule and a longer piece (usually 3-100 monomers) derived from another macromolecule; (ii) must be antigenic; and (iii) must be poorly exposed and/or poorly antigenic naturally or in vivo, and thus must be artificially, specifically and precisely created (free terminals) and/or exposed in samples and sample preparations by chemically engineered means, including, but not limited to, by using chemical bond-specific hydrolytic enzymes, agents, or their combinations.

A macromolecule-to-macromolecule conjugation site-specific ACE structure can be described as: Ln------L2-L1 (-S1-S2------Sm)-L1'-L2'------Lm', wherein L(# or #')s stand for residues and their numbers of one (e.g., long) macromolecular segment which has a branched covalent conjugation with a second macromolecule at L1; wherein S(#)s stand for residues and their numbers of the second (e.g., short) macromolecular segment in which S1 is covalently conjugated to L1; wherein L1, L2 etc. are counted toward one direction from the conjugation site (e.g., to the N-terminal direction of a polypeptide); wherein L1', L2' etc. are counted toward the opposite direction from the conjugation site; wherein S1, S2 etc. are counted toward the third or branched direction from the conjugation site; wherein the conjugation site is located between L1 and S1; wherein n, m and m' are residue numbers continuously counted from the L1, L1' and S1, respectively; wherein Ln, Lm', or Sm are not free ends naturally and have natural chemical bonds with residues outside of the ACE structure; and wherein the nature chemical bonds between Ln, Lm' or Sm and their ACE outside residues can be artificially, specifically and precisely cleaved by the chemical bond-specific hydrolysis in any sample preparations to expose the ACE structure(s) for detection.

Examples of the specific ACE structures are listed in various sections of this application, as well as in FIGS. 1-8.

By using the inventive ACE methods, we have successfully made several conjugation site-specific ACE antibodies that are highly specific to macromolecular conjugation sites in tissue sections or Western blot membranes (see FIGS. 3 and 9-13).

1.2. The ACE Antigen Design for Detecting Linear Hidden Antigen.

In addition to macromolecular conjugation site, the inventive ACE methods can also be used to detect any types of hidden antigens in samples or sample preparations, and have an advantage over the conventional antigen design and detection methods. This is because the chemical bond-specific hydrolysis strategy can artificially, specifically and precisely create and/or expose simpler and/or more charged terminal antigenic epitope(s).

The non-branched linear hidden ACE also has a general structure: L1-L2------Ln, wherein L1-L2------Ln is a single polymeric chain (e.g., polypeptide, polysaccharide, lipid, polynucleic acids, or their combinations), and either poorly antigenic or cannot be accessible in its original nature form by antibody, and thus must be artificially, specifically and precisely created and/or exposed by residue chemical bond-specific hydrolysis in situ or ex situ in sample preparations; wherein L(#)s stand for residues of the hidden antigen; wherein L1 and/or Ln are not free ends naturally or in vivo and have chemical bonds naturally with residues outside of the ACE structure; wherein the nature chemical bonds can be artificially, specifically, and precisely cleaved by residue chemical bond-specific hydrolysis in any types of sample preparations to create and/or expose the ACE structures for detection. An example is given in FIG. 2.

1.3. The ACE Antigen Design for Reducing Non-Specific Bindings.

The ACE methods can also be used to reduce antibody non-specific bindings in all antibody-based methods. The reduction of antibody non-specific binding is owing to the fact that the ACE methods can artificially, precisely and specifically create and/or expose the ACE, while breaking up the antibody non-specific binding structures as described below in Section 2, ACE antibodies, Example 4 and FIG. 13).

Examples of the ACE Antigen Design Methods

Example 1

A SUMO-to-Protein Conjugation Site-Specific ACE Structure Design

A SUMO can conjugate to many proteins including itself by an isopeptide bond. As demonstrated in FIG. 1A, a SUMO-to-SUMO conjugation site is between one SUMO C-terminal end glycine (G) and another SUMO internal lysine K11. Based on the ACE methods, a GluC-cleaved SUMO-to-SUMO conjugation site-specific hapten can be designed as GVK(GGTQQQFVDITDC)TE, wherein "C" is added to the hapten and conjugated to an immunogenic carrier, including, but not limited to, KLH or BSA to make the hapten a complete antigen. The conjugation site-specific antibody to GVK(GGTQQQFVDITDC)TE can be made with the complete antigen and purified with the hapten-conjugated resin or other supportive materials [e.g., GVK(GGTQQQFVDITDC-resin)TE]. The non-conjugation site antibodies can be removed by non-conjugated linear peptide-linked resin(s), e.g., (resin-GVKTE) and (GGTQQQFVDITDC-resin). After treatment with a protease or agent such as the designated protease (e.g., GluC) to artificially, specifically and precisely create and/or expose the GluC-cleaved ACE structure in a sample, the SUMO-to-SUMO K11 conjugation site can then be detected with the ACE antibody by any antibody-based methods.

FIG. 1B shows an alternative design, by the same ACE method, of SUMO-to-SUMO K11 conjugation site-specific ACE antigen. A SUMO-to-SUMO K11 conjugation site-specific hapten can also be designed as EGVK(GGTQQQGGGC)TENN, wherein "C" is added and conjugated to an immunogenic carrier including, but not limited to, KLH or BSA to make the peptide hapten a complete antigen; wherein "GGG" next to "C" is a spacer between the hapten and the immunogenic carrier; wherein EGVK(GGTQQQ)TENN is a truncated form of the trypsin-cleaved conjugation site-specific peptide "EGVK(GGTQQQFVDITDEDEMELQAPTDTENIPQGDF)TENNDHINLK"; and wherein the selection of a truncated form as a trypsin-cleaved ACE structure is consistent with the fact that a peptide epitope generally consists of 6-12 amino acids and this structure is preserved after trypsin treatment. The conjugation site-specific antibody to EGVK(GGTQQQGGGC)TENN can be made with the complete antigen and purified with hapten peptide-conjugated resin [e.g., EGVK(GGTQQQGGGC-resin)TENN]. The non-conjugation site-specific antibodies can be removed by non-conjugated linear peptide-linked resin(s), e.g., (GGTQQQGGGC-resin) and (EGVKTENNC-resin). After treatment with a protease or agent such as the designated protease (e.g., trypsin) to artificially, specifically and precisely create and/or expose the ACE structure in a sample, the SUMO-to-SUMO K11 conjugation site can then be detected with the antibody by any antibody-based methods.

FIG. 1C shows a design of SUMO-to-NF-kappa-B essential modifier (NEMO) conjugation site-specific ACE antigen by the ACE methods. NEMO is sumoylated at an internal lysine K277 (Homo sapiens) by SUMO1. A K277 conjugation site-specific hapten can be designed as CGGGALVAK(GGTQ)QE, wherein "C" is added to the peptide hapten and conjugated to KLH to make the hapten a complete antigen; and wherein "GGG" is a spacer. The K277 conjugation site-specific antibody to ALVAK(GGTQ)QE can be made with the complete antigen and purified with the hapten-conjugated resin [e.g., resin-CGGGALVAK(GGTQ)QE]. The non-conjugation site-specific antibodies can be removed by non-conjugated linear peptide-linked resin(s), e.g., (resin-CGGGALVAKQE) and (resin-CGGTQ). After treatment with a protease or agent such as the designated protease (e.g., GluC) to artificially, specifically and precisely create and/or expose the GluC-cleaved ACE structure in a sample, the SUMO-to-NEMO conjugation site can then be detected with the antibody by all antibody-based methods.

FIG. 1D shows an ACE design of SUMO-to-heat shock factor protein 1 (HSF1) conjugation site-specific antigen. HSF1 is sumoylated at a lysine residue K298 (Homo sapiens) by SUMO2/3. A conjugation site-specific hapten can be designed as RVK(GGTQQQGGC)E, wherein "C" is added to the peptide hapten and conjugated to an immunogenic carrier including, but not limited to, KLH or BSA to make the hapten a complete antigen; wherein "GG" is a spacer; and wherein "RVK(GGTQQQ)E" is the ACE structure. The K298 conjugation site-specific antibody to RVK(GGTQQQ)E can be made with the complete antigen and purified with the hapten-conjugated resin [e.g., RVK(GGTQQQGGGC-resin)E]. The non-conjugation site-specific antibodies can be removed by the non-conjugated peptide-linked resin(s), e.g., (resin-RVKE) and (resin-CGGTQQQ). After treatment with a protease or agent such as the designated protease (e.g., GluC) to artificially, specifically and precisely create and/or expose the ACE structure in a sample, the SUMO2/3-to-HSF1 K298 conjugation site can then be detected with the antibody by all antibody-based methods.

FIG. 1E shows an ACE design of SUMO-to-hypoxia-inducible factor 1 alpha (HIF1alpha) conjugation site-specific antigen. HIF1alpha is sumoylated at a lysine residue K391 (Homo sapiens) by SUMO2/3. A K391 conjugation site-specific peptide hapten can be designed as LK(GGTQQQGGC)K, wherein "C" is added to the hapten and conjugated to an immunogenic carrier including, but not limited to, KLH or BSA to make the hapten a complete antigen; and wherein "GG" is a spacer. The conjugation site-specific antibody to LK(GGTQQQ)K can be made with the complete antigen and then purified with hapten-conjugated resin [e.g., LK(GGTQQQGGGC-resin)K]. The non-conjugation site-specific antibodies can be removed by non-conjugated linear peptide-linked resin(s), e.g., (resin-CLKK) and (resin-CGGTQQQ). After treatment with a protease or agent such as the designated protease (e.g., trypsin) to artificially, specifically and precisely create and/or expose the ACE structure in a sample, the SUMO2/3-to-HIF1alpha K391 conjugation site can then be detected with the antibody by all antibody-based methods.

FIG. 1F shows a hydrolysis-guided ACE design of SUMO-to-p53 conjugation site-specific antigen. The p53 tumor suppressor is sumoylated at a lysine residue K386 (Homo sapiens) by SUMO1. A K386 conjugation site-specific peptide hapten can be designed as CGGGKLMFK(GGTQ)TE which is derived from the GluC-cleaved peptide PGGSRAHSSHLKSKKGQSTSRHKKLMFK(GGTQ)TE, wherein "C" is added to the hapten and conjugated to an immunogenic carrier including, but not limited to, KLH or BSA to make the hapten a complete antigen; and wherein "GGG" is a spacer. The ACE antibody to KLMFK(GGTQ)TE can be made with the complete antigen and then purified with hapten-conjugated resin [e.g., resin-CGGGKLMFK(GGT)K]. The non-conjugation site-specific antibodies can be removed by the non-conjugated peptide-linked resin(s), e.g., (resin-CKLMFKTE) and (resin-CGGTQ). After treatment with a protease or agent such as the designated protease (e.g., GluC) to artificially, specifically and precisely create and/or expose the ACE structure in a sample, the SUMO1-to-p53 K386 conjugation site can then be detected with the antibody by all immunological methods.

Example 2

Protein-to-Lipid (Protein Lipidation) ACE Antigen Design

A The ACE methods can be used to design protein lipidation conjugation site-specific antigens. Exemplary protein-to-lipid conjugations include, but are not limited to, the microtubule-associated protein 1A/1B-light chain 3 (LC3); gamma-aminobutyric-acid-type-A-receptor-associated protein (GABARAP); and Golgi-associated ATPase enhancer of 16 kDa (GATE16). Activation of these proteins requires lipidation of the C-terminal glycine (G) with phosphotidylethanolamine (PE). Therefore, antibodies specific to LC3-to-PE, GABARAP-to-PE, or GATE16-to-PE conjugation sites will be very useful in assays of the active forms and the autophagy pathway activities in physiological and pathological conditions. Unfortunately, such antibodies are not currently available. The inventive ACE methods can be used in this situation to design and detect the lipidated form-specific ACE epitope/antigens.

FIG. 2 shows an example of designs of LC3II-specific ACE antigen: Method 1a shows that TFG-phosphotidylethanolamine (PE) with a base sequence set forth by SEQ ID NO: 14 is synthesized with a peptide synthesizer and is used to make a liposome carrier for immunization. The LC3II-specific antibody can be made and purified with TFG-PE-containing liposome, by the method described in the book "Liposome Technology: Vol. III: Interactions of Liposomes with the Biological Milieu" By Gregory Gregoriadis, CRC Press, 1993. The shaded area indicates the expected ACE structure. Method 1b illustrates how the TFG-PE ACE structure is artificially, specifically and precisely created and/or exposed by GluC treatment and detected by the ACE antibody in a lipid membrane sample preparation.

Methods 2a, 2b and 2c of FIG. 2 show GluC-, CNBr- and trypsin-cleaved LC3P-PE-specific ACE antigen designs: TFGGGC; VYASQETFGC; and DEDGFLYMVYASQET-FGC (SEQ ID NOS: 14-16), respectively, wherein "GGG" in the TFGGGGC peptide is a spacer; and wherein the terminal "C" is added for conjugation to an immunogenic carrier. The LC3-PE-specific antibodies to base sequences set forth by SEQ ID NOS: 14-16 can be made with the complete antigens and purified with the hapten-conjugated resins, respectively. After treatment with the designated protease or agent (e.g., GluC, CNBr and trypsin, respectively) to artificially, specifically and precisely create and/or expose the corresponding ACE structures in sample preparations, the LC3-PE active form can be specifically detected with the (protease or agent) corresponding ACE antibodies by all antibody-based methods. Although cellular free pro-LC3 and LC3 also contain the base sequences set forth by SEQ ID NOS: 14-16, without conjugation to PE/membrane, they are too small to be retained in membrane samples or sample preparations and therefore can be washed out after hydrolysis treatment.

Methods 3 and 4 of FIG. 2 show phospholipase-D (PLD) and -C(PLC) cleaved LC3-PE-specific ACE antigen designs with a base sequence set forth by SEQ ID NO: 17: CGGGSQETFG-ethanolamine (for PLD) and CGGGSQETFG-phosphoethanolamine (for PLC), wherein "C" is added for conjugation to an immunogenic carrier, and "GGG" is a spacer. LC3-PE lipidation form-specific antibody can be made with the complete antigens and purified with the ACE hapten conjugated resins. After treatment with PLD or PLC to artificially, specifically and precisely create and/or expose the ACE structures in samples, the LC3-PE conjugated forms can then be detected with their (lipase) corresponding ACE antibodies by all antibody-based methods.

Example 3

Glycosylated Protein ACE Antigen Design

Alpha-fetoprotein (AFP) is glycosylated at the single asparagine (N) residue by a polysaccharide (N-link). Addition of a fucose to the innermost (also referred to as core) N-acetylglucosamine (GlcNAc) of AFP glycan via the alpha (1,6) bond (i.e., core-fucosylated AFP or Fuc-GlcNAc AFP) is seen mainly in cells, body fluids and tissues of many types of cancers, such as hepato-cellular carcinoma (HCC), thus being referred to as cancer-type AFP (Otake et al., 2001). Recent studies show that core-fucosylation of other proteins occurs also in pancreatic, prostate, colon, lung, and gastrointestinal cancers (Kossowska et al., 2005; Hu et al., 2008; Miyoshi et al., 2010; Osumi et al., 2009; Narisada et al., 2010; Moriwaki et al., 2010; Saldova et al., 2010; Wu et al., 2010). For that reason, the core-fucosylation conjugation site-specific antibodies to cancer tissue-specific proteins are very useful in R&D, diagnostics and therapeutics of different types of cancers. However, this type of antibodies cannot be made with general antigens because the antigens cannot be detected owing to steric hindrance from the long and folded polysaccharide chain and its conjugated protein, and thus, has not been available until now.

We produced the core-fucosylated AFP antibody by the ACE methods with the following steps: The glycoform-specific ACE haptens were designed as CGGGKVN(Glc-NAc)FTEI (SEQ ID NO: 1) (for the non-cancer types (non-core fucosylation types), and CGGGKVN[alpha(1,6) Fuc-GlcNAc]FTEI (SEQ ID NO: 1) for the cancer types (core-fucosylation types), respectively, wherein GlcNAc or alpha(1,6) Fuc-GlcNAc was linked to the sidechain of the asparagine (N) of AFP protein; and wherein CGGGKVN (GlcNAc)FTEI and CGGGKVN[alpha(1,6) Fuc-GlcNAc] FTEI were the ACE structures/segments specifically cleaved by Endo-N-acetyl-beta-D-glucosaminidase-D, -H or -F (EndoD/H/F). Conjugation site-specific antibodies to CGGG-KVN(GlcNAc)-FTEI or CGGGKVN[alpha(1,6) Fuc-Glc-NAc]FTEI were made with the KLH-conjugated complete antigen and purified with the hapten-conjugated resins. Non-conjugation site pan antibodies were removed with the non-glycopeptide-conjugated resins. After treatment with EndoD/H/F to artificially, specifically and precisely create and/or expose the hidden ACE structures in a sample, the cancer type and non-cancer type of AFP can be detected with their corresponding ACE antibodies by all antibody-based methods (see FIG. 3).

The method of detecting the core-fucosylated AFP with the glycoform-specific antibody is only an example of the invention. Other glycoproteins with the same core-fucosylation in normal and pathological conditions can be found in the literature (e.g., Goldfarb et al., 1986; Sekine et al., 1987; Matsumoto et al., 1994; Naitoh et al., 1999; Yamashita et al., 1989; Bunkenborg et al., 2004; Block et al., 2005; Mehta and Block, 2008; Communale et al., 2006; Sessom et al., 2008; de Leoz et al., 2008; Li et al., 2009; Szajda et al., 2008; White et al., 2009; Cao et al., 2009). Comprehensive information about updated core-fucosylated glycoproteins can also be found in publically accessible databases. However, conjugation site-specific antibodies to these glycoproteins are not previously available. The inventive ACE methods of making glycoform-specific antibodies and their use thereof can apply for detecting any glycoprotein that is currently known or will be identified in the future in normal or pathological conditions.

FIG. 3, Method 1 shows an example of glycoform-specific ACE antibody-based immunoassays with following steps: (i) two or more different glycoforms of the same protein backbone (e.g., two glycoproteins with the same polypeptide backbone, but with different glycan moieties) in a sample are digested with a single or a combination of endoglycosidases including, but not limited to, Endo D/H, which can artificially, specifically and precisely create (free terminals) and/or expose the innermost N-acetylglucosamine (GlcNAc), the innermost core fucosylated N-acetylglucosamine (Fuc-GlcNAc), or any other modified innermost GlcNAc on proteins; (ii) the digested mixture containing (monosaccharide) GlcNAc- and (disaccharide) Fuc-GlcNAc-glycoproteins is then incubated on a surface precoated with a general antibody (antibody 1) to a non-glycan portion of the protein; and (iii) additions of a fluorophor-1-labeled conjugation site-specific antibody (antibody 2) against the monosaccharide GlcNAc portion of the protein, and/or a fluorophor-2-labeld conjugation site-specific antibody (antibody-3) against the disaccharide Fuc-GlcNAc portion of the protein. The fluorophors can then be detected or imaged with a dual wavelength fluorometer.

FIG. 3, Method 2 shows another example of the glycoform-specific ACE antibody immunoassays in following steps: (i) in this case, two or more different glycoproteins with the same core-fucosylated N-glycan, e.g., glycoproteins-1 and -2 in a sample, are digested with Endo D/H to artificially, specifically and precisely create and/or expose the new conjugation site-specific ACE epitope; (ii) the digested mixture containing disaccharide Fuc-GlcNAc-proteins-1 and -2 is incubated on a surface precoated with a antibody against all Fuc-GlcNAc-asparagine-containing proteins; and (iii) additions of fluorophor-1-labeled antibody against a non-glycan portion of glycoprotein-1, and/or fluorophor-2-labeled antibody against a non-glycan portion of glycoprotein-2. The fluorophors can then be detected or imaged with a dual wavelength fluorometer.

FIG. 3, Method 3 shows a negative control for glycoform-specific antibody labeling. N-glycan glycoproteins are deglycosylated with PNGase F which removes the entire N-glycans from the proteins and creates non-glycosylated proteins in a sample. The PNGase F-deglycosylated proteins can still bind to a general antibody against non-glycan portions of the proteins, but cannot be recognized by conjugation site-specific antibodies to either the (monosaccharide) GlcNAc or (disaccharide) Fuc-GlcNAc portion of the proteins. This method can be used as a negative control for glycoform-specific antibody labeling.

FIG. 3, Method 4 further shows an example of Western blotting with AFP glycoform-specific antibodies. Samples were prepared from hepato-cellular carcinoma cell culture media, treated with non-enzyme solution as a control (Ctr), a mixture of endo-D/H, or with general PNGase-F (F), and then subjected to immunoblot analysis. Immunoblots were labeled with: (a) a general AFP antibody to a non-glycan portion of AFP, (b) a core-fucosylation site-specific AFP antibody, and (c) a monosaccharide GlcNAc (no core-fucosylation) AFP antibody. The general AFP antibody detects all glycosylated and de-glycosylated AFP bands (FIG. 3, Method 4a), the core-fucosylated site-specific AFP antibody labels only the core-fucosylated AFP (FIG. 3, Method 4b), and the (monosaccharide) GlcNAc site-specific AFP antibody labels only the monosaccharide GlcNAc AFP (FIG. 3, Method 4c).

Example 4

The Ubiquitin-to-Protein Conjugation Site-Specific Hidden ACE Antigen Design

As shown in FIG. 4, ubiquitin-to-ubiquitin conjugation site is between one ubiquitin C-terminal end glycine (G) and the internal (K48) residue of another ubiquitin, wherein a conjugation site-specific peptide hapten can be designed as CGGGLIFAGK(GG)QLEDGR, wherein the ubiquitin C-terminal dipeptide glycine-glycine (GG) is linked to the internal lysine K48 sidechain epsilon amino group by an isopeptide bond; and wherein "C" is added for conjugation to an immunogenic carrier, and GGG is a spacer. The conjugation site-specific antibody can be made with the complete antigen and purified with the hapten-conjugated resin. The non-conjugation site pan antibodies can be removed by the linear peptide-linked resin(s). After treatment with the designated protease (e.g., trypsin) to artificially, specifically and precisely create and/or expose the ACE structure in a sample, the hidden ubiquitin-to-ubiquitin K48 conjugation site can then be detected with the ACE antibody by all antibody-based methods.

FIG. 4 also shows a part of the basic rationale for a hidden ACE antigen design. The internal K48 residue of ubiquitin 1 is conjugated by the C-terminal end glycine of ubiquitin 2. The conjugation site LIFAGK$_{48}$(GG)QLEDGR is hidden on the inside of the ubiquitin-to-ubiquitin conjugate structure (FIGS. 4, A and B). Also, this conjugation site LIFAGK$_{48}$(GG)QLEDGR region in the intact conjugation form is poorly antigenic. Therefore, artificial and specific, rather than random or accidental, exposure of the hidden ACE structure with a specific protease(s) or hydrolytic agent(s) can improve the antibody accessibility to the antigen in a sample. In addition, the specific hydrolysis treatment can expose two free N-termini and one C-terminus. These newly created termini are charged and thus more antigenic. Our data show that these ACE methods are highly feasible, effective, and reliable in detecting hidden antigens in sample preparations (see FIGS. 3 and 9-13). The ubiquitin K48 conjugation site-specific antibody made by the ACE methods can specifically recognize both branched GG, and a portion of LIFAGKQLEDGR sequence. The invention also includes the negative absorption methods to remove non-conjugation site-specific antibody.

Similarly, ubiquitin-to-ubiquitin conjugation also occurs between one ubiquitin C-terminal G (glycine) and another ubiquitin either at the internal K6, K11, K27, K29, K33 or K63 residue, wherein conjugation site-specific ACE haptens can be designed as CGGGMQIFVK$_6$(GG)TLT for K6, TGK$_{11}$(GG)TITLEVEPSDTIEGGGC for K11, CGGG-LEVEPSDTIENVK$_{27}$(GG)AK for K27, AK$_{29}$(GG)IQDK-GGGC for K29, IQDK$_{33}$(GG)EGIPPDGGGC for K33, or CGGGTLSDYNI QK$_{63}$(GG)EST for K63, respectively; wherein the ubiquitin C-terminal end dipeptide GG is linked to the K6, K11, K27, K29, K33 or K63 sidechain epsilon amino group by an isopeptide bond or any other linkages; wherein C is added for conjugation to an immunogenic carrier; wherein GGG next to C is a spacer which may sometimes be added to the peptide hapten to increase the hapten structural flexibility and antigenicity; and wherein the MQIFVK$_6$(GG)TLT for K6, TGK$_{11}$(GG)TITLEVE-PSDTIE for K11, LEVEPSDTIENVK$_{27}$(GG)AK for K27, AK$_{29}$(GG)IQDK for K29, IQDK$_{33}$(GG)EGIPPD for K33, or TLSDYNIQK$_{63}$(GG)EST for K63, are truncated forms of the trypsin-cleaved specific peptides. After treatment with trypsin to artificially, specifically and precisely create and/or expose the hidden ACE structures in samples or sample preparations, the ubiquitin-to-ubiquitin K6, K11, K27, K29, K33 or K63 conjugation sites can then be detected, respectively, with their corresponding ACE antibodies by any antibody-based method.

Figure 5:
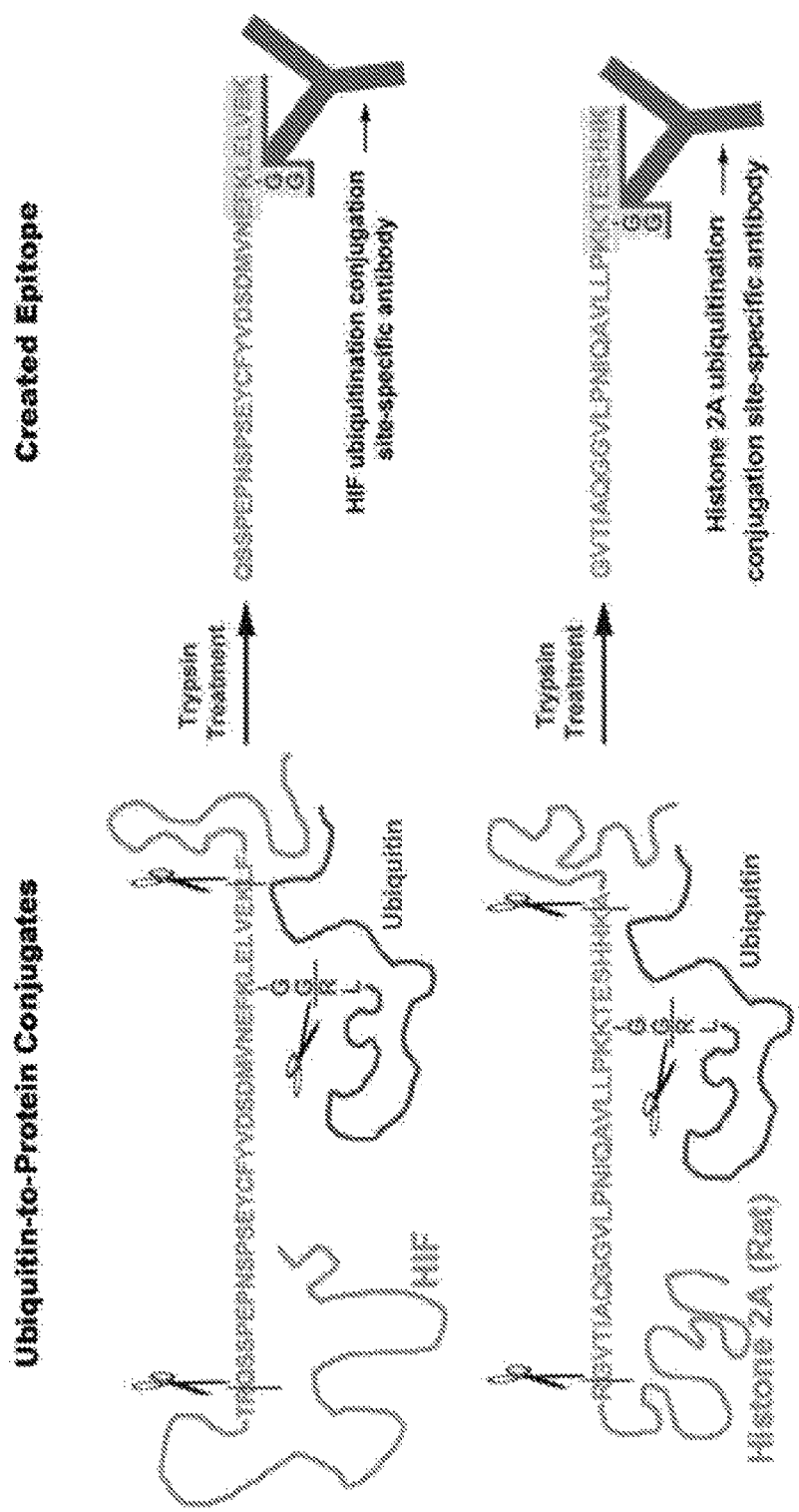

Similarly, ubiquitin-to-protein conjugation occurs between the ubiquitin C-terminal G (glycine) and an internal lysine (K) residue of any substrate protein. Two examples of the ACE antigen design are shown in FIG. 5. Example 1, hypoxia-inducible factor 1 alpha (HIF1alpha) is ubiquitinated at the lysine residue K532 (*Homo sapiens*). Based on the fact that an antigenic epitope generally requires 6-12 amino acids, the shaded area EFK(GG)ELVEK in FIG. 5 is the designated trypsin-cleaved conjugation site-specific ACE segment. A conjugation site-specific ACE hapten can be designed as CMVNEFK(GG)ELVEK, wherein "C" is added for conjugation to an immunogenic carrier. The conjugation site-specific antibody can be made with the complete antigen and purified with the hapten-conjugated resins. After treatment with trypsin to artificially, specifically and precisely create and/or expose the hidden ACE structure in a sample, the ubiquitin-to-HIF conjugation site can then be detected with this antibody by any antibody-based method.

Another example is the K120-ubiquitinated histone 2A (*Rattus norvegicus*) (FIG. 5). A conjugation site-specific ACE hapten is designed as KK(GG)TESHHKGGGC, wherein "C" is added for conjugation to an immunogenic carrier, and "GGG" is a spacer. The conjugation site-specific antibody can be made with the complete antigen and purified with the hapten-conjugated resin. The non-branched peptide-conjugated resin can be used to remove non-conjugation site pan antibodies. After treatment with trypsin to artificially, specifically and precisely create and/or expose the ACE segment in a sample, the ubiquitin-to-histone conjugation site can then be detected with this ACE antibody by all antibody-based methods.

Example 5

The Fatty Acid-to-Protein Conjugation Site-Specific ACE Design

Figure 6:
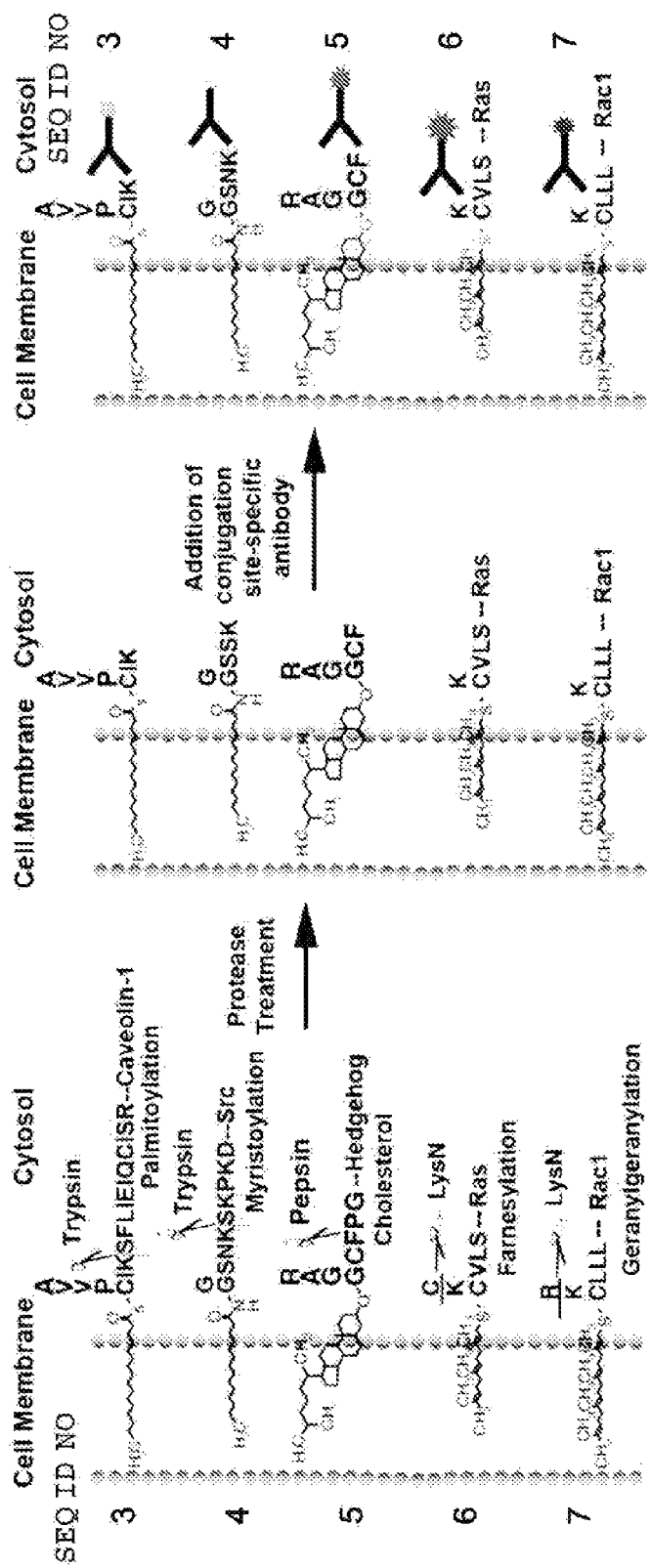

Similar to lipidated proteins described above in Example 2, a wide variety of cellular or viral proteins are covalently conjugated with a 14-carbon fatty acid myristate(s) and/or a 16-carbon fatty acid palmitate(s), as well as other fatty acids or lipid-related molecules. These types of protein lipidation are for associating the proteins to cell membranes from the cytoplasmic sides. Examples of making fatty acid-to-protein conjugation site-specific antibodies and their use thereof are shown in FIG. 6. Caveolin-1 is palmitoylated at three cysteine residues C133, C143 and C156 (*Homo sapiens*). A C133 palmitoylation site-specific ACE contains a base sequence set forth by SEQ ID NO: 3 and can be designed as CGGGAVVPC$_{133}$(palmitate)IK, wherein the N-terminal C is added for conjugation to an immunogenic carrier; wherein "GGG" is a spacer; and wherein palmitate is linked covalently to the C133. The conjugation site-specific antibody can be generated with the complete antigen and purified with the hapten-conjugated resins. The non-branched peptide-conjugated resins can be used to remove non-conjugation site pan antibodies. After treatment with trypsin to artificially, specifically and precisely create and/or expose the hidden ACE segment in a sample, the caveolin-1 C133 palmitoylation conjugation site can then be detected with the ACE antibody by any antibody-based method.

Similarly, proto-oncogene tyrosine-protein kinase Src (EC 2.7.10.2) (pp60c-src) (*Homo sapiens*) is myristoylated at the N-terminal end glycine residue (G2) (FIG. 6). A myristoylation site-specific ACE hapten contains a base sequence set forth by SEQ ID NO: 4 and can be designed as myristate-GSNK, wherein the N-terminal G is myristoylated, and the myristate chain can be conjugated to a liposome carrier to form a complete antigen for immunization. The conjugation site-specific antibody can be made with the complete ACE antigen and purified with myristate-GSNK-containing liposomes by the method described in the book "Liposome Technology: Vol. III: Interactions of Liposomes with the Biological Milieu" Gregory Gregoriadis (Editor), CRC Press, 1993. The non-conjugation site pan antibodies can be removed by the non-conjugated peptide-linked resin(s). After treatment with the designated protease or agent (e.g., trypsin) to artificially, specifically and precisely create and/or expose the hidden ACE structure in a sample or sample preparation, the pp60c-src C133 myristoylation site can then be detected with the ACE antibody by any antibody-based method.

Also, FIG. 6 illustrates: (i) sonic hedgehog protein (SHH) (*Homo sapiens*, BAA24866) that is covalently conjugated to cholesterol at the glycine residue (G197); (ii) the GTPase HRas (p21ras) (*Homo sapiens*) fernesylation at the 4$^{th}$ cysteine residue (C186) from the C-terminal end; and (iii) ras-related C3 botulinum toxin substrate 1 (p21-Rac1) (*Homo sapiens*) geranylgeranylation at the 3rd cysteine (C189) from the C-terminal end. Conjugation site-specific ACE antigens contain base sequences set forth by SEQ ID NOS: 5-7 and can be designed as CGGGAG$_{197}$(cholesterol) GCF for SHH; KC$_{186}$(farnesol)VLSGGGC for p21ras; and KC$_{189}$(geranylgeranyl isoprene)LLLGGGC for p21-Rac1, wherein the cholesterol, farnesol and geranylgeranyl isoprene are linked to the G197, C186 and C189 of their corresponding proteins, respectively; wherein the terminal "C" is added to the hapten for conjugation to an immunogenic carrier; and "GGG" next to "C" is a spacer. The conjugation site-specific antibodies can be made with their corresponding complete antigens and purified with hapten-conjugated resins. The non-conjugation site pan antibody can be removed by the non-branched peptide-linked resin(s). After treatment with pepsin for SHH, or LysN for both p21-ras and p21-Rac1 to artificially, specifically and precisely create and/or expose the ACE structures in sample preparations, the SHH, p21ras, and p21-Rac1 fatty acid conjugation sites can then be detected with their corresponding ACE antibodies by any antibody-based method.

Example 6

GPI-to-Protein Conjugation Site-Specific ACE Design

Figure 7:
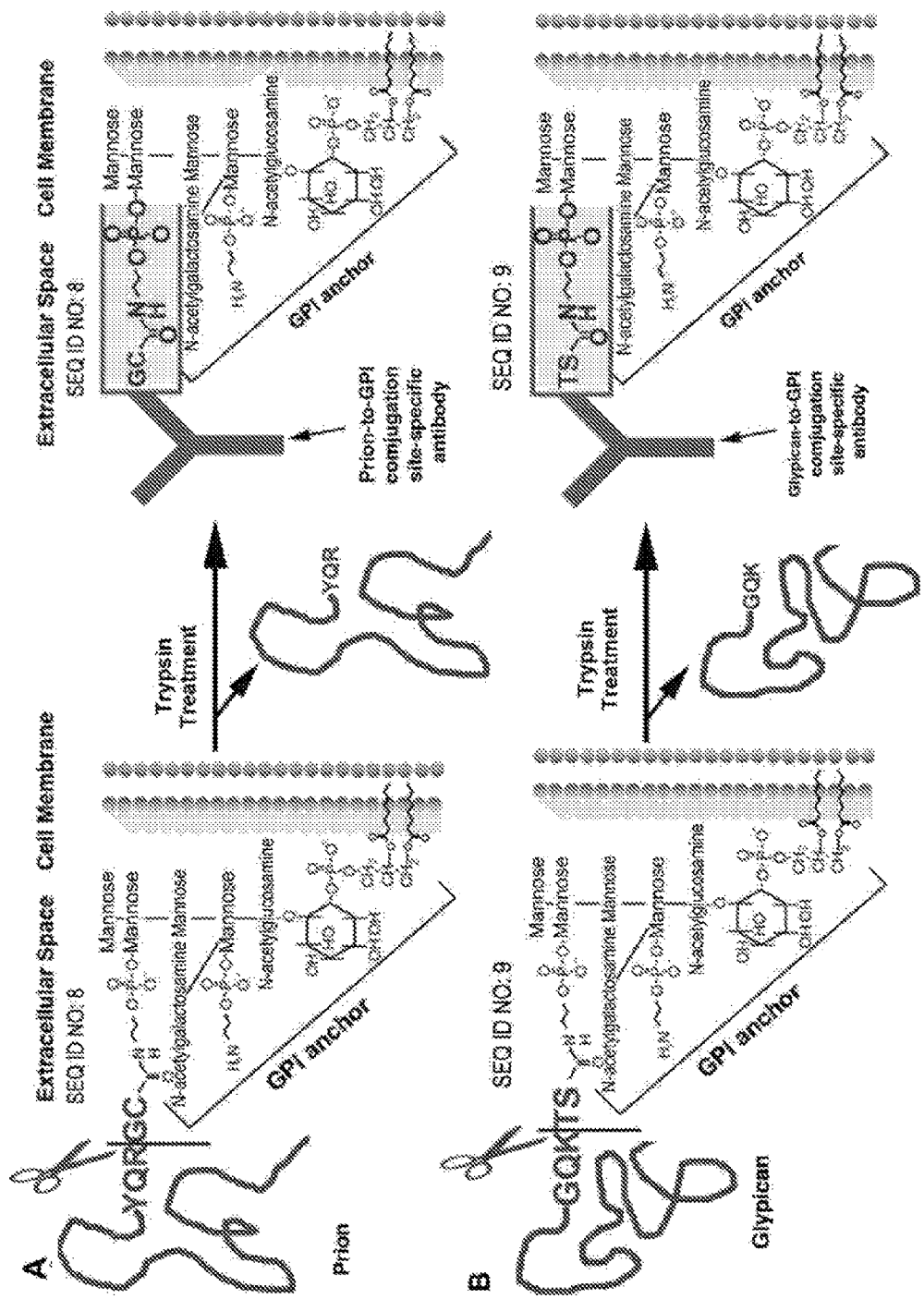

GPI is post-translationally conjugated to a group of structurally and functionally diversified proteins via an ethanolamine linker. This group of proteins is anchored in the outer leaflet of the cell membrane. FIG. 7 shows two examples of the ACE antigen design for making conjugation site-specific antibodies to GPI-anchored proteins and their use thereof. One is the prion protein (PrP) (*Homo sapiens*)

that is conjugated by a GPI-anchor at the cysteine residue C230. A conjugation site-specific ACE hapten contains a base sequence set forth by SEQ ID NO: 8 and can be designed as GC-phosphoethanolamine-SGGGC, wherein "SGGG" is added as a spacer and a linker that, via the serine hydroxyl side chain, links to phosphoethanolamine; wherein C is added for conjugation to KLH or BSA for making the hapten a complete antigen. The conjugation site-specific antibody to GC-phosphoethanolamine can be made with the complete antigen and purified with the hapten-conjugated resin. After treatment with trypsin to artificially, specifically and precisely create and/or expose the ACE structure in a sample, the PrP-to-GPI conjugation site can then be detected with the ACE antibody by any antibody-based method.

Another example is the glypican-1 that is also conjugated to GPI at a serine residue S530. A conjugation site-specific ACE hapten contains a base sequence set forth by SEQ ID NO: 9 and can be designed as TS-phosphoethanolamine-SGGGC, wherein "SGGG" is added as a spacer and linker that, via the serine hydroxyl side chain, links to phosphoethanolamine; wherein C is added for conjugation to KLH or BSA for making the hapten a complete antigen. The conjugation site-specific antibody to GC-phosphoethanolamine can be made with the complete antigen and purified with the hapten-conjugated resin. After treatment with trypsin to artificially, specifically and precisely create and/or expose the ACE structure in a sample, the glypican1-to-GPI conjugation site can then be detected with the ACE antibody by any immunological and antibody-based method.

Example 7

Transglutaminase-Mediated Conjugation Site-Specific ACE Antigen Design

Figure 8:
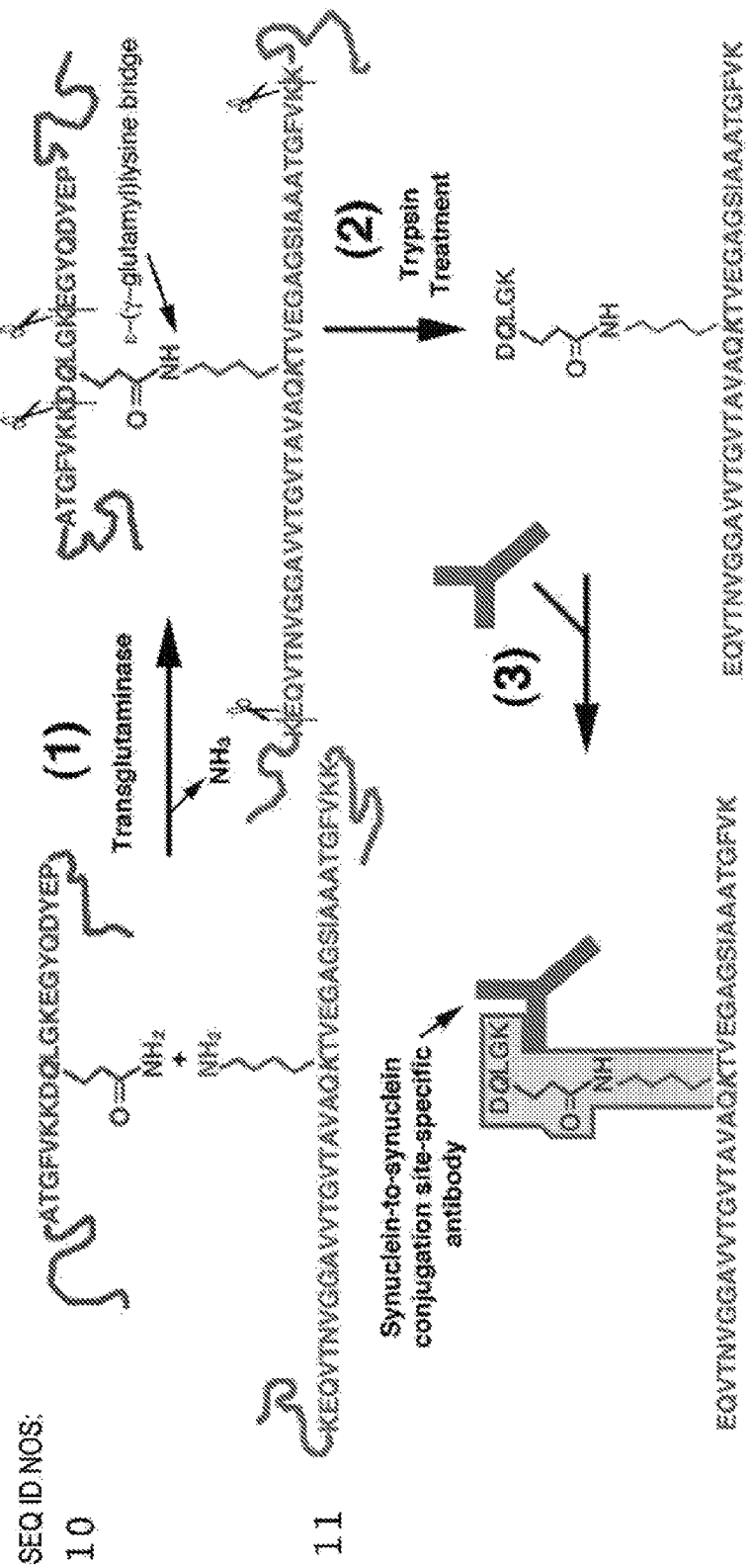

A Transglutaminases (TGs) are a family of structurally and functionally related enzymes that catalyze protein-to-protein conjugation via one protein's asparagine carboxamine to a lysine (K) of another protein. FIG. 8 shows an example of conjugation site-specific ACE hapten design for making antibodies to detect transglutaminase-mediated protein-to-protein conjugates and their use thereof. Transglutaminase-mediated synuclein-to-synuclein conjugation occurs between the glutamine 99 (Q99) and the lysine 80 (K80) residues via an e-(g-glutamyl)lysine bridge. A trypsin-cleaved synuclein-to-synuclein conjugation site-specific ACE hapten has base sequences set forth by SEQ ID NOS: 10-11 and can be designed as CGGGAQK(DQLGK)TV, wherein AQK(DQLGK)TV is a truncated form of the trypsin-cleaved ACE structure; and wherein "C" is added for conjugation to an immunogenic carrier, and "GGG" is a spacer. The conjugation site-specific antibody can be made with the complete antigen and purified with the hapten-conjugated resins. After treatment with the designated trypsin to artificially, specifically and precisely create and/or expose the hidden ACE structure in samples or sample preparations, the synuclein-to-synuclein conjugation site can then be detected with this ACE antibody by any immunological method.

Another example is the amyloid beta A4 peptide (beta/A4) that is the major component of amyloid plaque cores in Alzheimer disease, wherein the conjugation site is between the Q15 of one amyloid beta A4 peptide to the K28 of another amyloid beta A4 peptide by an isopeptide bond. A conjugation site-specific hapten contains base sequences set forth by SEQ ID NOS: 12-13 and can bedesigned as GSNK(YEVHHQK)GAII-GGGC via the Q-to-K conjugation, wherein C is added and conjugated to an immunogenic carrier and GGG is a spacer. The conjugation site-specific antibody can be made with the complete antigen and purified with the hapten-conjugated resins. The non-conjugation site pan antibodies can be removed by the non-branched peptide-conjugated resin(s). After treatment with trypsin to artificially, specifically and precisely create and/or expose the hidden ACE structures in samples or sample preparations, the amyloid beta A4 conjugation sites can be detected with this ACE antibody by all antibody-based methods.

Comprehensive information about normal and disease-related transglutaminase-mediated protein conjugation sequences can also be found in publically accessible databases including, but not limited to, Transdab at genomics.dote.hu/wiki/index.php/MainPage.

Example 8

ADP-Ribosylation Conjugation Site-Specific ACE Antigen Design

ADP-ribosylation is a reversible posttranslational modification by adding one or more ADP-ribose moieties to protein backbone. Both mono- and poly-ADP-ribosylated proteins involve in cell processes including, but not limited to DNA repair, genomic stability, and inflammation. Mono-ADP-ribosylation is initiated by ADP-ribosyltransferases, which transfer an ADP-ribose residue onto arginine, glutamic acid, or aspartic acid residues in their substrate proteins. Poly(ADP-ribosyl)ation is carried out by poly ADP-ribose polymerase (PARP) via transferring multiple ADP-ribosyl groups onto proteins to form long branched chains. Poly-ADP-ribosyl groups can be removed from proteins by poly(ADP-ribose) glycohydrolase (PARG), which catalyzes the hydrolytic removal of the branched poly(ADP-ribose) polymer, and produces mono-ADP-ribose-protein (Gagné et al., 2005). Many bacterial toxins including, but not limited to cholera toxin, diphtheria toxin, heat-labile enterotoxin; exotoxin A; pertussis toxin; and the like, are ribosyltransferases and modify human target proteins by ADP-ribosylation to exert their toxic effects. Therefore, bacterial toxin ADP-ribosylated proteins can be used as biomarkers of bacterial infections of particular diseases.

Several attempts have been made to produce antibodies to ADP-ribosylated residues. However, most of ADP-ribosylated residue antibodies lack specificity, and, more importantly, these antibodies do not recognize any specific protein poly-ADP-ribosylation sites (Liang et al., 2010). The ACE methods of this invention can be used to make an ACE antibody to a specific protein poly-ADP-ribosylation site. For example, P2X purinoceptor-7 (P2XR7) is an ATP receptor acting as a ligand-gated ion channel. Poly ADP-ribosylation of P2XR7 at the R125 residue regulates its function (Liang et al., 2010). A PARG-hydrolyzed P2XR7 ACE hapten can be designed as CPEYPTR(ADP-ribose)R with a base sequence set forth by SEQ ID NO: 2, wherein CPEYPTR(ADP-ribose)R is a segment of P2X7 ribosylation site, and can be synthesized with a peptide synthesizer and conjugated to an immunogenic carrier. ADP-ribose-to-P2XR7 conjugation site-specific ACE antibodies can be made with the complete antigen and purified with the hapten conjugated resins. Non-conjugation site pan antibodies can be removed with the linear peptide-conjugated resins. After treatment with poly ADP-ribosyl hydrolase (PARG), the P2XR7 ADP-ribosylation site can then be detected with the ACE antibody by any antibody-based method.

2. Methods of Making Ace Antibodies.

The present invention further discloses methods of using ACE antigens to make ACE antibodies. Such antibodies can be made with ACE antigens in conjunction with all antibody making methods including but not limited to those described in the books: Antibodies—A Laboratory Manual (1988), Cold Spring Harbor Laboratory Press, and Current Protocols in Immunology (1997), John Wiley & Sons, Inc. Exemplary antibodies may be polyclonal, monoclonal, humanized, bispecific, heteroconjugate antibodies, antibody-like binding partners, and the like.

2.1. ACE Polyclonal Antibodies:

The ACE polyclonal antibody can usually be made by injecting specific ACE antigens into animals including, but not limited to, chickens, goats, guinea pigs, hamsters, horses, mice, rats, sheep and the like. Specific ACE haptens are usually linked to an immunogenic carrier including, but not limited to, KLH, serum albumin, bovine thyroglobulin, soybean trypsin inhibitor, or the like. Adjuvants are normally used to improve or enhance an immune response to antigens. Blood serum from these animals contains polyclonal antibodies, also known as antiserum, that bind to the same ACE hapten or antigen. Antigens may be also injected into chickens for generation of polyclonal antibodies in egg yolks.

2.2. ACE Monoclonal Antibodies:

The ACE monoclonal antibody is normally derived from a single cell line and obtained by fusing antibody-secreting lymphocytes with a cancer cell line. A mouse, hamster, rat, rabbit or other appropriate host animal can typically be immunized with a complete ACE antigen made by attaching an ACE hapten to an immunogenic carrier. Alternatively, the lymphocytes may be immunized in vitro. Spleen cells immunized with ACE antigens are then fused with myeloma cells using a fusing agent to make hybridomas. A mixture of hybridomas is then diluted and subcloned. The clones from single parent cells are then selected. The antibodies produced from the single clones (monoclonal) are then tested for their binding affinity and specificity to the antigens by any single or combinations of antibody-based methods including, but not limited to, immunoblotting, immunohistochemistry, immunocytochemistry, immunoprecipitation, flow cytometry, peptide array, ELISA or all other immunoassays, or immunoelectron microscopy. The clones with the highest binding affinity and specificity to the ACE structures or clones for specific applications are then selected and grown in cultures or in the peritoneal cavity of animals to a high volume for the production of monoclonal antibodies.

Polyclonal and monoclonal antibodies can be purified using ACE hapten-conjugated matrices or resins, or by using Protein A/G or complete antigen-affinity chromatography for separation of antibodies from other molecules in crude antibody preparations. Negative absorptions may be required for separating conjugation site-specific antibodies from the non-conjugation site pan antibodies, such as by using non-branched peptide-linked resins.

2.3. ACE Recombinant Antibodies:

The ACE monoclonal antibodies may be natural or artificial (either partially or wholly), for example, recombinant DNA methods. Recombinant monoclonal antibody involves molecular cloning and expression of immunoglobulin gene segments in cells, viruses or yeasts. Immunoglobulin DNA expression vectors can be made with the DNAs from hybridoma cells immunized with ACE antigen. These vectors can then be transfected into a host cells including, but not limited to, myeloma cells in which recombinant monoclonal antibodies are expressed.

2.4. ACE Binding Partners:

The ACE antibodies or binding partners may also be made by methods including, but not limited to, phage display, yeast display, ribosome display, bacterial display, and mRNA display.

2.5. ACE Humanized Antibodies:

The ACE antigen can be used to make humanized antibodies or human antibodies made by recombinant methods. One approach is to merge an animal DNA sequence that encodes the small binding portion of a monoclonal antibody, with a human DNA sequence that encodes the rest of the large portion of the antibody. The hybrid DNA construct encoding the hybrid antibodies to ACE antigens can be readily isolated, sequenced and expressed for antibody production.

Examples of ACE Antibodies:

In the following immunofluorescence microscopic studies, tissue sections were prepared from animals perfused with ice-cold 4% paraformaldehyde in phosphate-buffered saline (PBS). Tissues were then postfixed in the same fixative at 4° C. for 24 h and then sectioned with a vibratome.

Example 1

Figure 9:
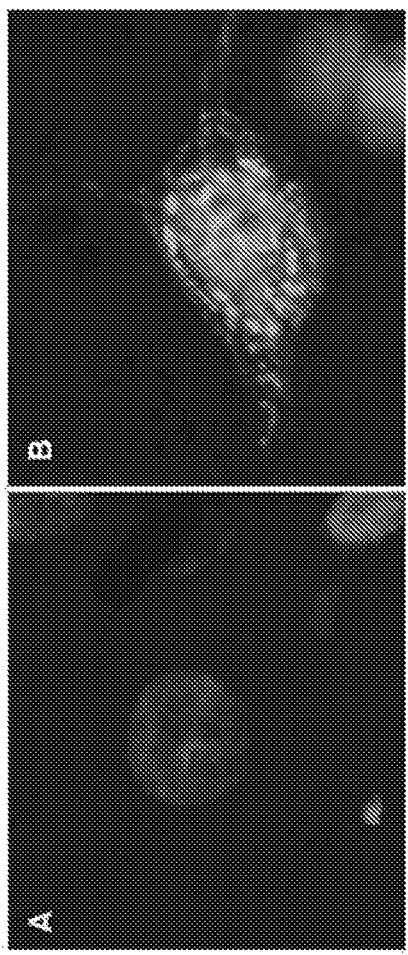

Conjugation site-specific polyclonal antibody to ubiquitin K48 conjugation site was produced with rabbits. This polyclonal antibody was designed to recognize the ubiquitin-to-ubiquitin K48 conjugation site ACE structure. FIG. 9 illustrates immunohistochemistry of tissue sections double-labeled with propidium iodide (PI) in a red color and with the ubiquitin K48 conjugation site-specific antibody in a green color. Tissue sections were treated without (A) or with (B) trypsin. After washing and blocking with BSA, tissue sections were incubated with the ubiquitin-to-ubiquitin K48 conjugation site-specific (primary) antibody at 4° C. overnight. Sections were then further washed and double-labeled with a fluorescein isothiocyanate (FITC)-labeled donkey to rabbit secondary antibody and PI. After washing, sections were mounted onto glass slides and examined under a microscope. The ubiquitin K48 conjugation sites show the green color, and PI-stained nucleic acids show the red color. In FIG. 9A, because, without trypsin treatment, the ubiquitin K48 conjugation site-specific ACE structures were not created and/or exposed and thus not labeled with the ubiquitin K48 conjugation site-specific antibody. Therefore, no green color is shown in tissue sections. In comparison, in FIG. 9B, because the K48 conjugation site-specific ACE structures were created and/or exposed artificially and specifically in tissue sections by trypsin treatment, the ubiquitin K48 conjugation sites were therefore labeled in the green color with the ACE antibody.

In the following Western blot analyses, tissue homogenates were prepared with 10 volumes of 20 mmol/L HEPES, pH 8.0, 0.25 mol/L sucrose, 1.25 µg/ml pepstatin A, 10 µg/ml leupeptin, 2.5 µg/ml aprotinin, and 0.5 mmol/L phenylmethanesulfonylfluoride or phenylmethylsulfonyl fluoride (PMSF). Protein concentration among samples was assayed and equalized with the buffer.

Figure 10:
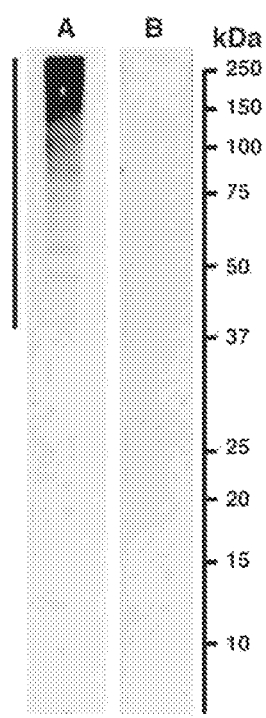

FIG. 10 shows a Western blot application of ACE antibody. Equal amounts of protein in samples were electrophoresed on 10% SDS-PAGE (sodium dodecyl sulfate polyacrylamide gel electrophoresis) and then transferred to nitrocellulose membranes. The membranes were blocked with BSA and 0.1% Tween 20 in PBS, and then treated either with trypsin in a HEPES buffer pH 8.0, or with the HEPES buffer only (as no trypsin control). The membranes were then incubated overnight at 4° C. with the ubiquitin-to-ubiquitin K48 site-specific ACE antibody with Tris/HCl-buffered saline (TBS) and 3% BSA. The membranes were incubated with a horseradish-peroxidase conjugated secondary antibody, and then developed using an ECL system. FIG. 10A shows that ubiquitin K48 conjugation sites were labeled with the ACE antibody because the hidden ubiquitin K48 conjugation site-specific ACE structures were created and/or exposed artificially and specifically with trypsin treatment of Western blot membranes. The high molecular weight smeared patterns or ladder bands were due to different sizes of polyubiquitinated proteins, which is consistent with the results of Western blotting polyubiquitin smeared patterns published in the literature. FIG. 10B shows that the ubiquitin K48 conjugation site-specific ACE antibody could not label polyubiquitin K48 conjugation sites because, without trypsin treatment, the polyubiquitin K48 conjugation site-specific ACE structures were not created and/or exposed.

Example 2

Immunoblot detections of hidden ACE antigens were shown in FIG. 11. Equal protein concentrations and volumes of tissue lysates were subjected to Western blot analysis. Before antibody labeling, the Western blot membranes were treated either without (−) or with (+) trypsin for FIG. 11A-D, or GluC for FIG. 11E. The hidden ACE structures were designed as CIMESFK(GG)NMVPQQALVIR for $Na^+/K^+$ ATPase or ATP1A1 (FIG. 11A); CHLNK(GG)MQNHGY-ENPTYK for Amyloid beta precursor-like protein 2 or Aplp2 (FIG. 11B); CLHEDPPQK(GG)PPR for amyloid beta protein precursor intracellular domain associated protein-1b or AIDA-1b (FIG. 11C); and CYQLFEELGK(GG)GAFSVVR (K21) for calcium/calmodulin dependent kinase II or CaMKII (FIG. 11D). The SUMO2/3-to-protein conjugation site ACE structure was designed as CGGKPKEGVK(GGTQQQ)TE (FIG. 11E). Without trypsin or GluC treatment (−), the specific protein bands were hidden and thus could poorly or not be detected with their corresponding ACE antibodies. In contrast, after trypsin (for FIG. 11A-D) or GluC (for FIG. 11E) treatment (+) to artificially, specifically and precisely create and/or expose the ACE structures, both conjugated (arrowheads), and non-conjugated protein bands (arrows) were detected with their corresponding antibodies.

As mentioned above, polyubiquitinated or polysumoylated protein bands have a character of fluffy/smearing patterns or ladder bands. The ~72 kDa AIDA-1b (see FIG. 11C) is also known as ankyrin repeat and sterile alpha motif domain-containing protein 1B or E2A-PBX1-associated protein (EB1). The protein band(s) above at 120-130 kDa is likely the ubiquitinated AIDA-1b because of its fluffy pattern. This antibody also recognizes AIDA-1d (~60 kDa and ~28 kDa), and AIDA-1e (~49 kDa), as described in a previous study (Jacob et al., 2010). The antibody to CaMKII labels many fluffy proteins bands which are likely the CaMKII conjugated by varied length of polyubiquitin, and their degradation products (FIG. 11D). The conjugation site-specific antibody to sumoylated proteins labeled several sumoylated protein bands, which is consistent with previous studies (e.g., Yang et al., 2008).

Example 3

A conjugation site-specific polyclonal antibody to ubiqutin-to-histone-2A K120 conjugation site was produced from rabbits. This polyclonal antibody recognizes only ubiqutin-to-histone2A K120 conjugation sites, and can be used in all antibody-based applications. FIG. 12 shows microscopic images of ubiquitin-to-histone K120 site immunostaining. Tissue sections were blocked with 3% BSA in Tris-buffered saline (TBS), treated without (A) or with (B) trypsin, and immunolabeled with ubiquitin-to-histone K120 conjugation site-specific ACE antibody (green) and PI (red) by the same method as that described above in Example 1. FIG. 12A shows that the nuclei in tissue sections could only be labeled with PI in the red color, because without trypsin treatment, the K120 conjugation site ACE structures were not artificially created and/or exposed. In comparison, FIG. 12B illustrates both PI-stained red nuclei and K120 conjugation-site specific antibody-labeled green ACE structures because, with trypsin treatment, the ubiquitin-to-histone K120 conjugation sites were artificially, specifically and precisely created and/or exposed.

Example 4

The inventive ACE methods can significantly reduce non-specific binding in all antibody-based applications. A key reason is that the hydrolytic treatment can artificially, specifically and precisely create and/or expose the ACE structures while breaking up antibody non-specific binding macromolecules. FIG. 13A shows that ubiquitin-to-histone K120 conjugation sites were labeled with the conjugation site-specific ACE antiserum because the ubiquitin-to-histone site-specific ACE structures were exposed artificially and specifically with trypsin treatment. The arrow indicates the monoubiquitin-to-histone K120 conjugate band. In comparison, FIG. 13B indicates that, without trypsin treatment, the ubiquitin-to-histone conjugation site-specific ACE antiserum labels many protein bands, which are likely antibody non-specific labeling because molecular sizes of these bands are inconsistent with that of the monoubiquitin-to-histone K120 conjugates. In this case, the ubiquitin-to-histone K120 conjugation site-specific ACE antibody was a crude antiserum. However, this piece of information suggests that the ACE methods are not only able to create or expose the ACE structures in an artificial, specific and precise manner, but also likely to break up macromolecules that otherwise bind to antibody non-specifically. Therefore, after trypsin treatment, most non-specific bands disappeared.

The feature of reducing nonspecific binding provides a further utility of the ACE methods. This is because chief obstacles associated with conventional antigen design and antibody production are: (i) weak antigenicity, (ii) antibody poor accessibility to antigen; and (iii) antibody non-specific binding. The inventive ACE methods can minimize all these obstacles by: (a) creating and/or exposing more antigenic N- and/or C-terminal ACE structure; (b) increasing antibody accessibility to the artificially and specifically created and/or exposed ACE structures; and (c) reducing non-specific bindings by the breakup of non-specific binding molecules.

The feature of reducing non-specific binding in the inventive methods may be also useful in immunoprecipitation (IP) studies. This is because the high levels of added immunoglobulin bands often disturb observing immuno-precipitated proteins/molecules of interest on Western blot membranes. The ACE methods can preserve the ACE structures while breaking up of added immunoglobulins on Western blot membranes, and thus eliminate unwanted immunoglobulin bands.

3. Methods of ACE Exposure and Detection.

The inventive ACE methods can solve the issues inherited in those epitopes that are: (i) hidden/concealed within molecule(s)/structure(s) and thus poorly or not accessible to large proteins/molecules like antibodies; (ii) poorly antigenic; and (iii) interfered with non-specific bindings. Such epitopes include, but are not limited to, those that are folded within their parent proteins/molecules, macromolecule-to-macromolecule covalent conjugation sites, molecule-to-molecule non-covalent binding sites, proteins/molecules that are inserted into cellular membranes, structures or organelles, and proteins/molecules that are interfered with non-specific bindings. In addition, the ACE structures with free terminals are more charged, and thus more antigenic than the internal sequence (Clark et al., 1969). Therefore, the ACE methods are effective in detecting hidden epitopes as shown in FIGS. 1-13.

In one embodiment, the invention provides methods of artificially, specifically and precisely creating and/or exposing ACE structures for detection; thus improving the ACE antigenicity and antibody accessibility in any types of sample preparations, wherein the ACE structures in samples or sample preparations are naturally absent or hidden, and poorly accessible to antibodies, and thus must be artificially and precisely created and/or exposed either in sample preparations by specifically selected hydrolytic enzymes or agents; wherein the artificially creating and/or exposing the ACE structures can be carried out in any type of sample preparations including, but not limited to, in vivo or in vitro, in whole or part of biological bodies or organisms, in isolated organs or organelles, in tissues or tissue sections (with or without fixation), in isolated or cultured cells, in body fluids or cell culture media, in tissue or cell lysates, in cellular or subcellular fractions, on Western blot membranes, in chromatographic or centrifuge fractions, in biochemical assay mixtures, and the like.

The method of creating and exposing the ACE structure in a sample preparation further comprises treating the sample preparation with a fixative before treating the sample preparation with the hydrolytic enzyme or hydrolytic agent. The fixative is selected from the group consisting of an aldehyde, an alcohol, acetone, and osmium tetroxide, including, but not limited to, formaldehyde, paraformaldehyde, and glutaraldehyde.

The said hydrolytic enzymes and agents for artificial ACE creation and/or exposure are specific and precise, rather than random or accidental (also see below). The enzymes and agents should be mostly the same, but can also be very occasionally different, with the one(s) used for the ACE antigen design. If the different hydrolytic enzymes or agents are selected, they must preserve the ACE structures for detection. The availability, property and chemical bond specificity of hydrolytic enzymes and agents for ACE exposures and detections can be found in public disclosures, publications/literatures, and websites including, but not limited to: www.expasy.ch/tools/peptidecutter.

Other methods to improve the accessibility of a hidden epitope are to use detergents (such as Triton X100 or SDS), different pH solutions, or physical measures such as heat to treat sample before performing antibody-based detections. These methods are principally and profoundly different, and usually less, if any, effective, relative to the ACE detecting methods. One explanation is that detergent and heat treatments are non-specific, random or accidental, usually cannot break covalent chemical bonds near the conjugation sites or folded molecules, and sometimes destroy (rather than expose) the epitopes. In comparison, the ACE methods employ the ACE antigen to make antibodies and then use ACE antigen design information to specifically, rather than randomly or accidentally, select residue chemical bond-specific hydrolytic enzyme(s)/agent(s) for artificially, specifically and precisely breaking the designated chemical bonds to create (new terminals) and/or expose the ACE structures for antibody detection. Therefore, the ACE methods not only fully preserve and expose the antigen structure, but also enhance antigenicity of the antigen structure by creating two (for a linear hidden antigen) or three (for a branched conjugation site) antigenic/charged terminals.

A number of antigen retrieval (AR) protocols have been published (Shi, 2011). To date, these protocols were solely for immunochemistry (ICC) or immunohistochemistry (IHC), and have been applied predominantly to archival "paraffin blocks" for IHC in diagnostic surgical pathology (Shi, 2011). Many antibody reagent companies also have antigen retrieval protocols on their websites. However, these protocols are not based on the ACE antigen design and detection described in this application, rather, they are based on random AR attempts and/or reversal of protein formaldehyde adducts and cross-links formed in the course of tissue fixation (Kuhlmann and Krischan, 1981). Therefore, these protocols are used solely for IHC or ICC and usually with a very low success rate, and have potential to destroy the antigen of interest. Therefore, the effectiveness of these protocols is accidental and unpredictable.

For example, the Abcam's protocol acknowledges that "most formalin-fixed tissue requires an antigen retrieval step before immunohistochemical staining can proceed. This is due to the formation of methylene bridges during fixation, which cross-link proteins and therefore mask antigenic sites." The Ihcworld's protocol (www.ihcworld.com) describes that "the use of enzyme digestion method may destroy some epitopes and tissue morphology". The protocol of R&D (www.rndsystems.com) recognizes that "the disadvantages of enzyme digestion method are the low success rate for restoring immunoreactivity and the potential for destroying both tissue morphology and the antigen of interest." It is also noted in the Millipore's protocol (www.millipore.com) that "the listed (enzyme digestion) procedure is only suggested; no warranty or guarantee of performance of the above procedure is made or implied".

For pathologists and morphologists, "seeing is believing" and most cancers are diagnosed by morphologic methods. O'Leary et al. (2010) and Shi (2011), two pioneers in the AR research, have suggested: "the AR technique is in many ways still in the developing stage. Further development of the AR technique must be based on a better scientific understanding of the molecular mechanisms, which represents the key pathways to improved cell/tissue sample preparation and standardization of IHC in clinical diagnostic applications."

The inventive ACE methods can robustly improve immunolabeling not only for IHC or ICC, but all antibody-based preparations including, but not limited to, in tissues or tissue lysates, cellular or subcellular fractions, Western blot membranes, chromatographic or centrifuge fractions, and the like (see FIGS. 3 and 9-14).

An additional step of the ACE methods requires artificially, specifically and precisely create (terminals) and/or exposure of the ACE structure before detection. At first glance, this seems an additional step in compared with conventional antibody detection methods. However, in practice, this step can breakup non-specific binding molecules, thus reducing non-specific bindings significantly in all antibody-based applications (see FIG. 13).

Another issue may be that artificial creation of new terminals and/or exposure of the ACE structure may change the size of the protein/molecule to be detected. This obstacle can be overcome by separation of samples first by, for instance, Western blotting, followed by ACE structure exposure (in situ) on Western blot membranes with specifically selected hydrolytic enzyme(s) or agent(s) for detection (see FIGS. 9-13). For immunohistochemistry, ACE in tissue sections can be exposed directly in situ with the specifically selected hydrolytic enzyme(s) or agent(s). After washing, the artificially exposed ACE structures can then be detected by the ACE antibody (see FIGS. 9-13). For immunoassays, regular two-antibody sandwich methods can be used, i.e., a general antibody binds the non-conjugation sites or the outside of the ACE structure, whereas the ACE antibody binds the conjugation sites or the linear ACE structures.

A host of residue chemical bond-specific hydrolytic enzymes or chemical agents including, but not limited to, proteases, glycosidases, lipases/phospholipases, poly(ADP-ribose) hydrolases, nucleases, and the likes, are available and can be specifically selected for the ACE methods. The criteria for selecting specific hydrolytic enzymes or agents for the ACE antigen design/detection depend on the molecular sequence of the ACE structure, and the substrate chemical bond-cleaving specificities, and the ACE organization, size and antigenicity. The selecting criteria also depend on which antibody-based methods/applications will be used. For Western blot analysis, for example, it is not ideal to select an enzyme that creates too small pieces of ACE structures. Therefore, the use of the ACE methods requires understanding the structure, organization and location information of hidden antigens, the properties of hydrolytic enzymes or chemical agents, and which antibody-based methods/applications are used.

A limitation of the inventive ACE methods in immunoprecipitation (IP) studies may be that the ACE antibody may immunoprecipitate the hydrolytic fragments, rather than entire macromolecule-to-macromolecule conjugates or linear hidden antigens. This limitation can be overcome by IP of molecular conjugates with non-conjugation site-specific antibodies, followed by separation of the IP protein(s), for instance, by Western blotting. The ACE structures of the IP protein(s)/molecule(s) can then be artificially and specifically created and/or exposed by the chemical bond-specific hydrolysis, and be specifically detected with the ACE antibodies. Another potential limitation of the ACE detection methods may be that ACE antigen is sometime too small to be detected by two antibodies in the classical two antibody sandwich enzyme-linked immunosorbent assay (ELISA) methods due to stereo hindrance effect. This potential limitation can also be overcome by selecting different ACE structures (see ACE design), by using a competitive immunoassay or ELISA method, or by ACE elution/extraction methods, followed by ACE detection including, but not limited to: (a) conventional IP method followed by ACE elution; (b) the surface liquid ACE extraction methods described in the website www.advion.com and by Kertesz et al. (2010); (c) antibody-based nanoparticle ACE extraction methods (Gupta et al., 2007; Chan et al., 2008); and the likes. After extraction, ACE can be detected by any methods including, but not limited to, all types of chromatography, spectroscopy, and mass spectrometry.

4. Utilities of Ace Methods, Reagents, Antibodies, Immunoassays and Kits.

In the era of "-omics", including but not limited to genomics, proteomics, glycomics, metabolomics and histomics, our knowledge of structures, sequences, molecular conjugation and modifications, as well as properties of hydrolytic enzymes and chemical agents has grown exponentially. This provides an exceptional opportunity for using the inventive ACE methods, antibodies, reagents, immunoassays and kits to detect, in a conjugation site-specific manner, posttranslational modifications including but not limited to glycosylation, lipidation, ubiquitination, sumoylation, other UBLs, as well as any types of post-translational modifications of numerous individual macromolecules.

The present invention encompasses various utilities and applications of the ACE methods including, but not limited to: (i) research and discovery (R&D), (ii) diagnosing diseases, monitoring of disease stage and response to treatment, and disease prognosis, (iii) screening of therapeutic agents, (iv) determining conjugation or de-conjugation enzyme and agent activities, (v) detecting hidden antigens that are normally difficult to be detected by general antibody-based methods, (vi) reducing antibody non-specific bindings in all antibody-based methods, (vii) therapeutic applications for treatment of abnormal molecular conjugation or de-conjugation-related diseases, and (viii) bio-materials.

4.1. Diagnostic Applications of the ACE Methods, Antibodies, Reagents, Immunoassays and Kits:

Abnormal macromolecular conjugations occur in many diseases, and can be used as disease-specific biomarkers. However, antibodies to macromolecule-to-macromolecule conjugation sites are difficult to make by the conventional antibody design and detecting methods, because, as described above, most, if not all, macromolecule-to-macromolecule conjugation sites are hidden antigens, and thus they are not currently available. The inventive methods of designing and detecting hidden ACE antigens can therefore be used for disease diagnosis, staging, monitoring progress and treatment, and prognosis. The following are a few examples:

4.1.1. Diagnosis of Lysosomal Storage Diseases:

Lysosomal storage diseases (LSDs) are a group of approximately 40 rare inherited metabolic disorders that result from defects in lysosomal function, The incidence of LSDs, together as a group, is about 1:5,000-1:10,000. LSDs including but not limited to Danon disease, Pompe disease, X-linked myopathy and bowel diseases occur mostly as a result of deficiency of a single enzyme required for the metabolism of lipids and glycoproteins.

The common diagnostic features include: (a) accumulation of the lipids and glycoproteins in the cell or body fluids; and (b) accumulation of autophagosome biomarker protein LC3II.

The conjugation site-specific ACE antibodies of the invention can be used for diagnosis of LDS by determining the autophagosome biomarker LC3II, and specific glycoproteins or lipidated protein in tissues or body fluids.

4.1.2. Diagnosis of Neurological, Neurodegenerative and Conformational Diseases:

The presence of positive ubiquitinated aggregates is a common hallmark of neurological and neurodegenerative diseases including, but not limited to, Alzheimer's disease (AD), Parkinson's disease (PD), Huntington's disease (HD), amyotrophic lateral sclerosis (ALS), prion diseases, as well as vascular diseases, diabetes mellitus, and the like. For instance, stroke induces significant increase in ubiquitinated proteins in brain tissue, blood and cerebrospinal fluid (CSF). AD aggregates contain ubiquitin-conjugated beta-amyloid and Tau proteins (Cripps et al., 2008) and AD CSF has "paired helical filaments antigen" (Kudo, 1998; Mehta et al., 1985; Perry et al., 1989). PD aggregates consist of ubiquitin-conjugated alpha-synuclein and/or parkins. HD has ubiquitin-conjugated polyglutamine repeat aggregates. ALS has ubiquitin-conjugated SOD-containing aggregates and TAR DNA binding protein (TDP-43). Prion diseases have ubiquitin-conjugated prion aggregates in the tissue, CSF and sera, but each disease has its own specific ubiquitin-conjugated proteins as indicated above.

Unfortunately, the ubiquitin-to-protein conjugation site-specific biomarkers described above can only be detected by a combination of many sophisticated methods that are not applicable to regular clinical laboratory settings. As a result, no reliable laboratory disease-specific biomarkers are currently available for diagnosing neurodegenerative diseases in living patients, which is critical for stopping disease progression. Early AD and other neurodegenerative disease symptoms are subtle, and thus the clinical diagnosis mostly relies on postmortem histopathology examination, from which only a portion of patients can be diagnosed. For that reason, developing early stage disease-specific diagnostic biomarkers that can unambiguously discriminate among different neurodegenerative diseases is a key step for developing early therapeutic interventions of cell degeneration.

Although still in the infancy, some proteins have been identified in CSF and circulating blood as potential biomarkers of neurodegenerative diseases. For example, high levels of "paired helical filaments antigen" in AD patient CSF can be recognized by antibody against residues 64-76 of ubiquitin, suggesting that CSF of AD patients contains polyubiquitin conjugates (Kudo, 1998; Mehta et al., 1985; Perry et al., 1989).

TAR DNA-binding protein 43 (TDP-43) regulates transcription and splicing and is a major component of ubiquitin-positive and tau-negative neuronal and glial inclusions in the most common form of frontotemporal lobar degeneration (FTLD) and in ALS. High level of ubiquitin-conjugated TDP-43 can be detected in CSF from FTLD and ALS patients. It has been demonstrated that different TDP-43 profiles correspond to clinical phenotypes of FTLD or ALS subgroups. The differential diagnostic potential of TDP-43 was therefore suggested (Jellinger, 2009; Steinacker et al., 2008; Kasai et al. 2009; Bian and Grossman, 2007).

In addition to CSF, general ubiquitin positive immunoreactivities have been detected in nervous and non-nervous tissues virtually in all neurodegenerative disorders, or all other protein conformational diseases (Dickson, 2005). These include, but are not limited to, ubiquitin immunopositive amyloid plaques and neurofibrillary tangles in AD, alpha-synuclein-containing aggregates and Lewy bodies in PD, ubiquitin-TDP43 aggregates in ALS and FTLD, Huntingtin nuclear inclusion in HD, and ubiquitin immunoreactivity in and around areas with spongiform changes in prion diseases. The types and manifestations of ubiquitin positive immunoreactivities in neurodegenerative diseases are quite complicated and thus hard to discriminate one disease from another. Therefore, new diagnostic tools that can discriminate different types of ubiquitinated proteins as disease biomarkers are desperately needed.

Because of the diversity of ubiquitin-conjugated proteins in tissue, cell and body fluids, conjugation site-specific antibody that recognizes a specific ubiquitin-conjugated protein and its conjugation site(s) is extremely useful for diagnosis or differential diagnosis of a particular disease, as suggested by Iwatsubo et al. (1996) and Dickson (2005). However, such conjugation site-specific antibodies are not currently available because of no effective methods for making them against conjugation site-specific hidden epitopes/antigens. The present invention provides the ACE methods and conjugation site-specific antibodies for designing and detecting disease-specific ubiquitin-to-protein conjugation sites in tissue samples or body fluids, thus offering unique tools for diagnosis of specific diseases.

For example, monoubiquitination of alpha-synuclein via the E3 ubiquitin-ligase SIAH leads to formation of Lewy body. Monoubiquitinated alpha-synuclein also works as a seed to recruit PD-related proteins, including, but not limited to, ubiquitinated synphilin-1 and ubiquitin carboxyl-terminal esterase L1 (UCH-L1) (Engelender, 2008; Szargel et al., 2008). The inventive conjugation site-specific antibodies to the ACE structures GLSK(GG)AK and AK(GG)EGVVAAAEK of monoubiquitinated alpha-synuclein, and/or EGVVAAAEK(GG)-TK of ubiquitinated synphilin-1, and ubiquitinated UCH-L1 in circulating blood samples, CSF, or other body fluids, have great potential as a cohort of biomarkers to diagnose PD of the alpha-synuclein type. Therefore, to detect a cohort of PD biomarkers of the alpha-synuclein type in tissue, circulating blood, and/or other body fluids, the following conjugation site-specific ACE antibodies can be used: (i) conjugation site-specific antibodies to two different ubiquitin-to-alpha-synuclein conjugation sites made with GLSK(GG)AK and AK(GG)EGVVAAAEK, respectively; (ii) conjugation site-specific antibody to ubiquitinated synphilin-1 made with EGVVAAAEK(GG)TK; (iii) conjugation site-specific antibodies to four different sites of ubiquitinated UCH-L1 (ubiquitin carboxyl-terminal esterase L1) made with $MQLK_4(GG)PMEINPEMLNK$, $K_{65}(GG)QIEEL$, $QIEELK_{71}(GG)GQEVSPK$, and $VDDK_{157}(GG)VNFHFILFNNVDGHLYELDGR$, respectively (Meray and Lansbury, 2007; Engelender, 2008; Szargel et al., 2008).

To detect a cohort of AD biomarkers in tissue, circulating blood, and/or other body fluids, the following conjugation site-specific ACE antibodies can potentially be used: (i) conjugation site-specific antibody to ubiquitin-to-amyloid precursor protein (APP) made with an ACE peptide HLSK(GG)MQQNGYENPC; (ii) conjugation site-specific antibody to ubiquitin-to-Tau made with an ACE peptide $CHVPGGGSVQIVYK_{311}(GG)PVDLSK$; (iii) conjugation site-specific antibody to ubiquitin-to-enolase1 made with an ACE peptide CIEEELGSK(GG)AK; (iv) conjugation site-specific antibody to ubiquitin-to-ubiquitin K48 conjugation made with an ACE peptide LIFAGK(GG)QLEDGRC; (v) conjugation site-specific antibody to the Toll-interacting protein made with an ACE peptide LAK(GG)NYGMTRC; and (vi) conjugation site-specific antibody to ubiquitin-conjugating enzyme E2 UbcH-ben made with an ACE peptide IDILK(GG)DKWSPALQIRC. These potential AD-specific biomarker candidates are selected based on literature and our recent studies showing that their levels in brain tissues were dramatically increased in AD transgenic animals.

A further example is to detect a cohort of HD biomarkers in tissue, circulating blood and/or body fluids. The following conjugation site-specific ACE antibodies may be used: (i) antibody to ubiquitinated huntingtin made with an ACE peptide MATLEK(GG)LMK; and (ii) antibody to sumoylated huntingtin made with an ACE peptide KLMK(GGTQ)AFE (Finkbeiner et al., 2008, Waelter et al., 2001, Steffan et al., 2004).

A additional example is that the conjugation site-specific antibody made with the ACE epitope $CMATLEK_6(GG)LMK$ (of TDP-43) may be used to detect a biomarker of frontotemporal lobar degeneration (FTLD) and ALS in tissue, circulating blood, and/or body fluids (Jellinger, 2009; Steinacker et al., 2008; Kasai et al. 2009; Bian and Grossman, 2007).

The diagnostic biomarkers listed above are only a few examples. The inventive ACE methods can be used to make conjugation site-specific antibodies and antibodies to any hidden antigens for all biomarkers that are currently known and will be identified in the future.

4.1.3. Diagnosis of Aberrant Glycoprotein-Related Diseases:

Aberrant glycosylation of proteins changes protein function and activities, and thus can lead to diseases or be byproducts/biomarkers of diseases (Durand et al., 2000; Tong et al., 2003; Troyer et al., 2004; Valmu et al., 2006; Saffroy et al., 2007; Arnold et al., 2008; Debruyne et al., 2008; Ressom et al., 2008; Zhao et al., 2008). For instance, the following diseases contain aberrant glycoproteins: I-cell disease, congenital disorders of glycosylation, leukocyte adhesion deficiency type II, hereditary erythroblastic multinuclearity with a positive acidified serum test, and Wiskott-Aldrich syndrome. In addition, some disease cells, including, but not limited to, those in alcoholism and cancers, can produce unique diseased forms of glycoproteins that can be used as biomarkers for disease diagnosis, staging, monitoring treatment, and prognosis.

A classic example is aberrant glycosylation of alpha-fetoprotein (AFP) in cancer cells. AFP is an oncofetal serum protein consisting of 591 amino acids (*Homo sapiens*) and containing only a single asparagine-linked (N-link) polymeric carbohydrate chain (Debruyne et al., 2008). AFP is a major fetal plasma glycoprotein produced in normal embryonic tissues, but its level becomes barely detectable after birth. In hepatocellular carcinoma (HCC) and seminomatous germ-cell tumors, serum AFP is greatly increased. The reappearance of AFP in HCC patient serum is currently being used as a cancer biomarker. However, the use of AFP as a cancer biomarker is severely limited by the fact that its level is also increased in patients with benign liver diseases including but not limited to hepatitis and liver cirrhosis.

There are several glycosylated forms (known as glycoforms hereafter) of AFP. The glycoform specific for hepatocellular carcinoma (HCC) is the one with the alpha (1,6)-fucosylated innermost GlcNAc known as the core-fucosylation, whereas the glycoform in benign liver diseases does not have this core alpha(1,6)-fucosylation.

The binding capacity of different AFP glycoforms varies towards *lens culinaris* agglutinin A (LCA) lectin. Therefore, LCA lectin has been used to isolate three different glycoforms of AFP, namely AFP-L1 (LCA non-reactive), AFP-L2 (LCA intermediate reactive) and AFP-L3 (LCA-affinitive reactive) (Breborowicz et al., 1981). AFP-L3 contains a high level of the AFP glycoform with the core-fucosylation. The AFP-L3 assay (owned by Wako Diagnostics, Japan) was approved as a biomarker for diagnosis of HCC by the U.S. Food and Drug Administration in 2006.

However, the routine measurement of AFP-L3 as a biomarker is somewhat hampered by relatively high cost, low sensitivity, expensive instrumentation, and complexity of currently available assays. Other methods for diagnosis of HCC such as ultrasound imaging are expensive and cannot detect the appearance of HCC with tumor masses less than 3 cm in size.

In addition to the lectin-based AFP-L3 assay, Comunale et al. (2009) published another lectin-based method for detection of the core fucosylated forms of fetuin-A and hemopexin (United States Patent Application Number: 20070037221). The core-fucosylation of serum proteins and their lectin binding activities have been known for many years (Goldfarb et al., 1986; Matsumoto et al., 1994; Yamashita et al., 1989; Block et al., 2005; Communale et al., 2006; Mehta and Block, 2008). The lectin-based detections of core-fucosylated serum proteins in cancer patients have frequently been reported as reviewed by Hirabayashi in 2008.

Lectins are a diverse group of carbohydrate-binding proteins. Each lectin has its own specific binding profile. Lectin-binding affinity to glycoproteins, however, is generally about $10^3$ lower than antibody-binding affinity to antigen (Hirabayashi, 2008). Another disadvantage of lectin-based assays is that lectin can bind to many different types of glycan moieties; thus its binding specificity is low relative to antibodies. For example, lectin-fucose interaction is not specific for the core fucosylation (the innermost alpha1,6-fucosylation) but also for other types of fucosylation. Furthermore, lectin-to-sugar interaction is not protein-specific. A further practical disadvantage of using lectin is that, unlike antibodies, immobilization of lectin usually leads to reduction of lectin-to-glycan binding affinity and capacity (Hirabayashi, 2008). Despite these weaknesses, lectin is the only currently available agent to separate core-fucosylated proteins from non-fucosylated ones.

Ideally, a biomarker assay should possess high specificity, affinity and capacity, as well as, being convenient to use, high throughput, highly reproducible and with a low cost. According to these criteria, antibody possesses many significant advantages relative to lectin and other binding partners. Unfortunately, antibodies that can specifically recognize core-fucosylated serum proteins are currently not available.

The present invention provides unique immunoassays to detect core-fucosylated proteins by using the core-fucosylation conjugation site-specific ACE antibodies (see above Section 1, ACE antigen design, Example 3 and FIG. 3). For example, the glycoform conjugation site-specific antibodies of the invention can either recognize only the core-fucosylated peptide VN[alpha(1,6)-GlcNAc]FTEI of AFP (the HCC glycoform), or only the non-fucosylated peptide ACE VN[GlcNAc]FTEI of AFP (the non-cancer form) (see FIG. 3). Similarly, the ACE methods can be used to detect tissue-specific core-fucosylated proteins (see below) for diagnosis of different types of cancers. The antibody-based immunoassays of the present invention are specific for particular glycoproteins. and technically sound, as well as simpler, more sensitive, higher throughput. and with lower cost, relative to lectin-based assays.

As described in SECTION 1: METHODS OF DESIGNING ACE ANTIGENS, Example 3: Glycosylated protein ACE antigen design, FIG. 3 shows two examples of glycoform-specific ACE immunoassays. Example 1: (a) two or more different glycoforms of the same protein are digested with a single or mixture of endoglycosidases, e.g., Endo D/F/H, which will leave only the innermost N-acetylglucosamine (GlcNAc) or the core-fucosylated Fuc-GlcNAc on the protein backbones; (b) the resulting (monosaccharide) GlcNAc- or (disaccharide) Fuc-GlcNAc-to-protein conjugates are incubated on a surface precoated with a general antibody (antibody 1) to a non-glycan portion of the protein; and (c) addition of the fluorophor-1-labeled conjugation site-specific antibody (antibody 2) to the GlcNAc portion of the protein, and/or the fluorophor-2-labeled conjugation site-specific antibody (antibody-3) unique to the Fuc-GlcNAc portion of the protein. The fluorophors are detected and quantified with, for example, a dual wavelength fluorometer.

FIG. 3 example 2 further shows another type of immunoassay in which: (a) two or more different proteins with the same core-fucosylated moiety, e.g., glycoproteins-1 and -2, are digested with a single or mixture of Endo D/F/H; (b) the resulting disaccharide Fuc-GlcNAc-proteins-1 and -2 are incubated with a surface precoated with the core-fucosylation site-specific ACE antibody generally to the common disaccharide Fuc-GlcNAc-asparagine (ACE) structure; and (c) addition of a fluorophor-1-labeled antibody to a non-glycan portion of glycoprotein-1 and/or a fluorophor-2-labeled antibody to a non-glycan portion of glycoprotein-2. The fluorophors can be then detected or imaged with, for example, a dual wavelength fluorometer.

Increase in core-fucosylated proteins in cancer patient serum is not restricted to AFP. Many other glycoproteins are also core-fucosylated in many different types of cancers including, but not limited to, lung and pancreatic cancers, as described in previous publications (Goldfarb et al., 1986; Sekine et al., 1987; Matsumoto et al., 1994; Naitoh et al., 1999; Yamashita et al., 1989; Chang et al., 2000; Bunkenborg et al., 2004; Block et al., 2005; Communale et al., 2006; Li et al., 2007; de Leoz et al., 2008; Li et al., 2009; Szajda et al., 2008; White et al., 2009; Cao et al., 2009). For example, core-fucosylation of E-cadherin is upregulated during cancer metastasis including, but not limited to, lung cancer and colon carcinoma (Hu et al., 2008; Osumi et al., 2009). Decrease in core-fucosylated proteins in leukocyte adhesion deficiency/congenital disorder is also observed (Sturla et al., 2005; Wang et al., 2006). Therefore, as mentioned above, specific core-fucosylated proteins can be used as biomarkers for diagnosis of specific cancer types. The inventive ACE methods can be used to design and develop antibodies to detect specific core-fucosylated proteins as listed below for diagnosis of specific types of cancers. Information on core-fucosylated proteins in tissue, body fluids and other biological samples is well documented in publically accessible databases including but not limited to National Center for Biotechnology Information at www.ncbi.nlm.nih.gov/ and ExPASy at www.expasy.ch/, and in public disclosures, literatures and publications (e.g., Mehta and Block, 2008; Cao et al., 2009).

Some examples of core fucosylation site-specific ACE structures of the invention include, but are not limited to, (the bold letter indicates the conjugated asparagine): serotransferrin NYN[Fuc(alpha1,6)-GlcNAc]KSD; alpha-1-acid glycoprotein-1: QDQCIYN[alpha(1,6)-Fuc-GlcNAc]TTYLNVQR; alpha-1-acid glycoprotein-2: QNQCFYN[alpha(1,6)-Fuc-GlcNAc]SSYLNVQR; alpha-1-antitrypsin: ADTHDEILEG LNFN[alpha(1,6)-Fuc-GlcNAc]LTEIPEAQI; alpha 2-HS glycoprotein: VCQDCPLLAPLN[alpha(1,6)-Fuc-GlcNAc]DTRVVHAAK; alpha-2-glycoprotein-1: DIVEYYNDSN[alpha(1,6)-Fuc-GlcNAc]GSHVLQGR; apolipoprotein: ADGTVNQI EGEATPVN[alpha(1,6)-Fuc-GlcNAc]LTEPAK; complement factor h (isoform 1): IPCSQPPQIEHGTIN[alpha(1,6)-Fuc-GlcNAc]SSR; haptoglobin: NLFLN[alpha(1,6)-Fuc-GlcNAc]HSEN[alpha(1,6)-Fuc-GlcNAc]ATAKDIAPT; hemopexin: SWPAVGN[alpha(1,6)-Fuc-GlcNAc]CSSALR; immunoglobulin G: GLTFQQN[alpha(1,6)-Fuc-GlcNAc]ASSMCVPDQDT; kininogen: HGIQYFNN[alpha(1,6)-Fuc-GlcNAc]NTQHSSLFMLN, or LNAENN[alpha(1,6)-Fuc-GlcNAc]ATFYFK; serotransferrin: CGLVPVLAENYN[alpha(1,6)-Fuc-GlcNAc]KSDNCEDT or QQQHLFGSN[alpha(1,6)-Fuc-GlcNAc]VTDCSGNFCL; ceruloplasmin: EHEGAIYPDN[alpha(1,6)-Fuc-GlcNAc]TTDFQR; transthyretin: VVFTAN[alpha(1,6)-Fuc-GlcNAc]DSGPR; alpha-1-microglobulin: YFYN[alpha(1,6)-Fuc-GlcNAc]GTSMACETFQ; galectin-3-binding protein: PFYLTN[alpha(1,6)-Fuc-GlcNAc]SSGVD; GP-73: AVLVNN[alpha(1,6)-Fuc-GlcNAc]ITTGER; E-calherin-1: EHVKN[alpha(1,6)-Fuc-GlcNAc]STYTA or ELTHGASAN[alpha(1,6)-Fuc-GlcNAc]WTIQY (SEQ ID NOs: 1 and 18 through 39).

4.1.4. p53 Ubiquitination-, Sumoylation- and Neddylation-Related Biomarkers.

The p53 tumor suppressor functions as a transcription factor that is maintained at low levels in unstressed cells. In response to oncogenesis, p53 levels and transcriptional activity are significantly altered, in part by post-translational modification, including, but not limited to, ubiquitination, sumoylation, neddylation, phosphorylation and acetylation. The murine double minute (mdm2) oncogene-encoded protein Mdm2 is a RING-like E3 ubiquitin ligase and acts as a negative regulator/inhibitor of the p53 tumor suppressor. Mdm2 is up-regulated in many tumors, and promotes ubiquitination of p53 at multiple lysine residues, such as K370, K372, K373, K381, K382 and K386, as well as neddylation of p53 at K370, K372, and K373 residues. p53 can also be sumoylated at the K386 residue.

The present invention provides methods of detecting ubiquitinated, neddylated or sumoylated p53. For example, ubiquitinated and neddylated p53 K370, K372 and K373 site-specific ACE antigens can be designed as (i) KLH-CGGGSSHLK$_{370}$(GG)SK, (ii) SK$_{372}$(GG)KGGGC-KLH, and (iii) SKK$_{373}$(GG)GQSTRGGGC-KLH, respectively. A sumoylated p53 K386 site-specific ACE antigen can be designed as LMFK$_{386}$(GGQT)TEGPDGGGC-KLH. Ubiquitined K381, K382 and K386 conjugation site-specific p53 ACE antigens can be designed as K$_{381}$(GG)K$_{382}$(GG)GQSTSRGGGC-KLH and LMFK$_{386}$(GG)TEGPDGGGC-KLH. Therefore, these ACE antibodies to ubiquitinated, neddylated and sumoylated p53 may be used to monitor progression of tumors and cellular responses to DNA damage.

4.1.5. ACE Antibodies to Ubiquitinated Proliferating Cell Nuclear Antigen (PCNA).

PCNA is an auxiliary protein of DNA polymerase delta, and involved in the control of eukaryotic DNA replication by increasing the polymerase's processibility during elongation of the leading strand. In response to DNA replication or damage, this protein is ubiquitinated at K164. A ubiquitin-to-PCNA K164 conjugation site-specific ACE antibody can be made with an ACE structure KLH-CDAVVISCAK(GG) DGVK and can potentially be used to detect the ubiquitinated PCNA as a cancer biomarker by all antibody-based methods.

4.1.6. ACE Antibodies to Ubiquitinated Tubulin:

A growing number of cancer drugs including, but not limited to, taxanes, vinca alkaloids and epothilone ixapebilone can bind to tubulins and thus alter their ubiquitination. Microtubules are composed of α- and β-tubulin heterodimer filaments in the hollow cylinder. Many cancer drugs can bind to tubulins and thus alter their assembly state and increase their degradation by the ubiquitin proteasome system. This type of cancer drugs has been used in the clinic for over 2 decades. The inventive ubiquitin-to-tubulin conjugation site-specific antibodies to tubulin ACE epitopes/antigens such as KLH-CANQMVK(GG)CDPR can be used to detect the ubiquitin-to-tubulin biomarkers in tissues and body fluids in all antibody-based applications for monitoring tubulin-affecting drug treatment efficiency or efficacy.

4.1.7. GPI-Anchored Proteins and Disease Biomarkers.

Several well-established cancer biomarkers are GPI-anchored membrane proteins including, but not limited to, glypican-3, carcinoembryonic antigen (CEA), semaphorins, and urokinase receptor (uPAR). GPI-anchored proteins are often release to body fluids, including, but not limited to, blood and CSF. A technical challenge is the low levels of GPI-anchors in body fluids. The inventive methods and GPI-anchor conjugation site-specific antibodies can potentially be used to detect GPI-anchored proteins in a specific manner (see FIG. 7).

4.2. Discovery of Molecular Conjugation Sites and Sequences:

In bioreagent or R&D area, ACE methods, reagents, antibodies, immunoassays and kits can be used in all antibody-based applications including but not limited to detect, identify, isolation, locate and characterize macromolecular conjugation sites or hidden antigens including, but not limited to, protein, saccharide, lipid and nucleic acid, or any combination of the above in a sample. The ACE structures can be artificially created and/or exposed directly either in situ or ex situ on Western blot membranes, tissue sections or any other type of biological sample preparations.

ACE methods, antibodies, reagents, immunoassays, and kits can be used directly for all antibody-based separations of conjugation site-specific and any types of hidden ACE structures including, but not limited to, peptides, saccharide, lipid, nucleic acids, or any combination of the above, followed by identification with methods of genomics, proteomics, glycomics, histomics, metabolomics, and the likes.

An example is to separate molecules in a biological sample with 2-dimensional electrophoresis gel, followed by exposing ACE structures with designated hydrolytic enzymes or agents, and then labeling the spots on the gel/blotting membranes with the ACE antibodies. The ACE positive spots on the gel or membrane can be cut, extracted, and identified with any mass spectrometry (MS)-related methods.

Another example is that ACE structures/segments can be captured with the ACE antibodies in a mixture or biological sample lysates, and then detected by any analytical methods. In the MS method, ACE parent macromolecules in a sample may need to be denatured, and then digested with designated hydrolytic enzymes or agents, to artificially, specifically and precisely expose the ACE structures. After isolation from the sample with the corresponding immobilized ACE antibodies, and then elution from antibody, the ACE structures can then be identified by MS-related methods.

A further example is to separate glyco-, lipidated, UBL- and GPI-anchored proteins with the general ACE antibodies to the common portion of the ACE structures in a sample including, but not limited to: (i) ACE antibodies recognizing the common N-linked glycoprotein ACE structures [Fuc (alpha1,6)-GlcNAc-asparagine, or GlcNAc-asparagine asparagine] (see FIG. 3), (ii) ACE antibodies to the common GPI structures, (iii) ACE antibodies to the common lipid portion of lipidated ACE structures (see FIG. 6), and the like. The ACE structures separated by the general antibody can then be identified by analytical methods including, but not limited to, MS-methods.

An additional example is to identify ACE structures in samples by the method of antibody array-coupled peptide surface liquid extraction. The procedure includes: (i) coat ACE antibodies to surfaces or matrices mostly by covalent means; (ii) treat samples with specifically selected ACE hydrolytic enzymes or agents; (iii) inhibit the hydrolytic enzymes or agents with inhibitors or any other means, or separate the hydrolytic enzymes or agents from the samples by any biochemical means; (iv) incubate ACE segment-containing samples with ACE antibody-coated surfaces or matrices; (v) separate bound from non-bound ACE segments on the surfaces or matrices by washing; (vi) extract bound ACE segments by appropriate liquid including, but not limited to, low pH buffers or organic solvents; (vii) detect ACE segments in the liquid by any analytical means including, but not limited to, liquid chromatography, fluorescent, ultraviolet and visible spectrometry, or any MS-related methods.

4.3. Utilities in Enzymatic Activity Assays:

There are a number of approaches for measuring enzyme activities associated with discoveries of therapeutic agents. For example, antibody-based immunoassays of protein kinase activities currently represent the largest drug target class screened in high throughput screening (HTS) laboratories, mostly because phospho-specific antibodies are widely available.

Similar to protein phosphorylation, macromolecule-to-macromolecule conjugation also plays a central role virtually in all cellular metabolic processes. However, unlike protein kinase activity assays, there are no macromolecular conjugation site-specific antibodies currently available for assaying macromolecule-to-macromolecule conjugation enzyme activities.

The present invention provides ACE methods, reagents, antibodies, immunoassays and kits for assaying macromolecular conjugation-related enzyme activities, modulators, cofactor, and the regulatory chemicals. The following are a few examples:

4.3.1. Methods of Assays of Autophagy Activities with LC3II (LC3-PE)-Specific ACE Antibodies.

The macroautophagy (autophagy hereafter) pathway is the chief route for bulk degradation of aberrant cellular contents. A biomarker unique to autophagy is the LC3II (=LC3-PE conjugates). LC3 is a mammalian homologue of yeast autophagy-related gene (ATG) product ATG8. LC3/ATG8 is synthesized as a pro-LC3/ATG8, and then cleaved by ATG4 protease to become a 16-18 kDa LC3I/ATG8I. Upon activation of autophagy, LC3I/ATG8I is conjugated or lipidated with phosphatidylethanolamine (PE). The lipidated form is the active form and referred to as LC3II/ATG8II. The formation of LC3II conjugates is carried out by two consecutive ubiquitination-like enzyme systems, involving ATG7 (activating enzyme) and ATG3 (conjugating enzyme) for LC3II (or LC3-PE)/ATG8II formation.

Classical methods to measure autophagy activities are quantitative EM and degradation rate of a long-lived protein. The EM method is labor-intensive and requires dedicated personnel and expensive equipment, whereas the method of a long-lived protein turnover rate is poorly autophagy-specific. A new biomarker unique to autophagy is the LC3II which is formed via conjugation of LC3I with PE (lipidation, see FIG. 2). However, there is no antibody that recognizes only the active form LC3II. The present invention provides ACE methods to detect only (lipidated or active) LC3II, and can be used to assay autophagy activities by all antibody-based methods (see FIG. 2).

The LC3II-specific ACE antibodies of the invention can be used to assay LC3II formation-related enzyme activities including, but not limited to, ATG3, ATG7, ATG10 and ATG4, as well as these enzyme modulators, cofactors, or LC3II-related pharmacological agents. The assay system should contain LC3I or its peptides, PE, adenosine triphosphate (ATP), as well as ATG3, ATG7, or ATG4, or the enzyme modulators, cofactors or LC3II-related pharmacological agents. After the reaction, enzymes or their modulator activities as reflected by the formation of LC3II, can be determined with the LC3II-specific antibody.

4.3.2. Methods of Assays of Fatty Acid-to-Protein Conjugation Enzymes and their Modulators:

Fatty acid-to-protein conjugations play key roles in the localizations and functions of proteins and thus are directly involved in endocytosis, cellular signaling, and many diseases. Numerous cellular and viral proteins are known to contain covalently bound lipid groups. Myristoylation occurs at the N-terminal glycine residue by addition of, via an amide bond, a 14-carbon saturated acyl group. Palmitoylation takes place at a C-terminal domain cysteine residue by a thioester bond. Prenylation is mediated by the formation of a thioester bond between a C-terminal domain cysteine and isoprenoids, farnesol or geranylgeraniol. Protein prenylation substrate proteins include, but are not limited to H-Ras, K-Ras, Rheb (Ras homolog enriched in brain), CENP-E (centromere-associated protein E), and RhoB. The C-terminal glycine residues can be covalently attached with a cholesterol moiety by an ester bond. Cell outside surface proteins can be anchored to the membrane by linking to a GPI moiety (Ferri et al., 2005).

Many proto-oncogenes including, but not limited to, pp60src family and Ras family, are post-translationally lipidated and thus, they have been drug targets for developing cancer drugs (see FIG. 6). For example, protein farnesyl transferase (FPTase) inhibitors (FTIs), protein geranylgeranyl transferase type I (GGPTase-I) inhibitors (GG-TIs), as well as the dual prenylation inhibitors (DPIs) inhibit lipidation of Ki-ras and are currently in clinical trials for the treatment of cancers. HDJ2 is an FPTase-specific substrate, and Rap1A is a GGPTase-I-specific substrate, and thus have been used as biomarkers for measurement of geranylgeranylation and farnesylation activities, respectively (Lobell et al. 2002). FTIs may also be used to inhibit farnesylation in parasites including, but not limited to, *trypanosoma* (African sleeping sickness) and *plasmodium falciparum* (malaria) (Cardoso et al., 1983).

Statins are used to inhibit cellular cholesterol and isoprenoid biosynthesis, resulting in a decrease in protein lipidation in vivo. For example, statins inhibit the dimerization of beta-secretase [BACE (beta-site amyloid precursor protein-cleaving enzyme)] by inhibiting the lipidation of BACE and its associated proteins (Parsons et al., 2007). Therefore, lipidated BACE may be used as a biomarker for evaluation of statin treatment efficiency and efficacy.

The present invention provides methods of designing and detecting lipidation site-specific ACE structures, and can be used to evaluate protein lipidation status and effect of protein lipidation modulators or pharmaceutical drugs in vivo. Lipidation state-specific ACE antibodies may further be used to assay activities of protein lipidation enzymes and their modulators. The antibody-based assays typically contain a non-lipidated protein or peptide substrate (including, but not limited to, HDJ2 and Rap1), a lipid donor, ATP, and a lipidation enzyme including, but not limited to, N-myristoyltransferases (NMTs), palmitoyl acyltransferases (PATs), farnesyltransferases, geranylgeranyltransferases, or the likes. After incubation, the lipidation enzyme activity as reflected by the rate of formation of the lipidated conjugates, can be determined with the lipidation conjugation site-specific ACE antibodies. Information about enzymes and substrates of protein lipidation can also be found at: mendel.imp.ac.at; bioinformatics.lcd-ustc.org; and expasy.org.

4.3.3. Methods of Assays of Protein Glycosylation Enzymes and their Modulators:

N-linked glycoproteins are covalent polysaccharide-to-protein conjugation via GlcNAc-to-N chemical bond. The N-linked amino acid consensus sequence is N-X-S/T (X=any amino acid except proline). N-linked glycosylation is important for protein folding and many other functions of proteins. O-linked glycoproteins are another covalent saccharide-to-protein conjugation via GlcNAc-to-S/T chemical bond. Currently there is not an O-linked amino acid consensus sequence. O-linked glycosylation involves cell-to-cell adhesion by sugar complexes of proteoglycans. Proteins that circulate in the blood are not normally O-glycosylated, with the exception of IgA1/IgD and C1-inhibitor.

Glycosyltransferases are a group of enzymes (EC 2.4) that catalyze transferring saccharide unit from an activated sugar phosphate (known as the "glycosyl donor") to an acceptor molecule. Protein glycosylation belongs to a co-translational and posttranslational modification and is processed in different cellular compartments, particularly in the endoplasmic reticulum (ER) and Golgi apparatus, by glycosyltransferases and glycosidases. Most, if not all, membrane and secretory proteins are glycosylated.

The present invention provides ACE methods and conjugation site-specific antibodies for measuring protein glycosylation-related enzymatic activities including, but not limited to, glycosidases, glycosyltransferases, and their modulators, cofactors or pharmacological agents. These antibody-based assays are typically carried out in a system that contains non-glycosylated substrates including, but not limited to, proteins or peptides, activated glycosyl donors (e.g. UDP-glucose, UDP-galaxies, UDP-GlcNAc, UDP-GalNAc, UDP-xylose, UDP-glucuronic acid, GDP-mannose, GDP-fucose, or CMP-sialic acid), ATP regenerating systems, and glycosylation-related enzymes (either natural or recombinant), or glycosylation-related enzyme modulators, cofactors, chemical activators or inhibitors. After the reaction, the glycosylation enzyme activity as reflected by the rate of formation of the glycosylated proteins or glycosylated peptides, can then be determined with the conjugation site-specific ACE antibody.

4.3.4. Methods of Assays of Ubiquitination and De-Ubiquitination Enzyme Activities and their Modulators:

Ubiquitin is a highly conserved regulatory 76 amino acid polypeptide found in all eukaryotic cells either free or covalently bound to other proteins. Ubiquitination (or ubiquitylation) is an enzymatic, protein post-translational modification process in which the carboxylic acid terminal glycine of the activated ubiquitin forms an amide bond to the epsilon amine of the lysine in the modified protein. Protein ubiquitination is carried out consecutively by ubiquitin activating enzyme (E1), ubiquitin conjugating enzyme (E2), and ubiquitin ligase (E3) to catalyze conjugation of ubiquitin to a protein. Successive conjugation of activated ubiquitin to the K-48, or K-63 lysine of the previously conjugated ubiquitin form polyubiquitin chains. Polyubiquitin via K48-linkage is generally recognized by the proteasome for degradation, whereas K63-linked polyubiquitin and monomeric ubiquitination is generally thought, at least in part, to function as proteasome-independent processes including but not limited to endocytosis, and regulation of enzymatic or transcriptional activities.

The present invention provides ACE methods, antibodies, reagents, immunoassays and kits for measuring activities of protein ubiquitination-related enzymes including, but not limited to, ubiquitin ligases, ubiquitin hydrolases as well as their modulators, cofactors or chemical agents. The antibody-based assays of ubiquitin ligase activities can typically be carried out in a system that contains ubiquitin and its substrates (including ubiquitin itself), a ubiquitin conjugation enzyme fraction (s) that contains E1, E2 and E3 enzymes, ATP regenerating systems, and ubiquitin-related enzymes (either natural or recombinant), and ubiquitin-related enzyme modulators, cofactors or chemical agents. Ubiquitination-related enzymatic activities can be measured as the rate of formation of the ubiquitin-to-protein/peptide conjugates with their corresponding conjugation site-specific antibodies.

For example, the human double minute (Hdm2) oncogene is an E3 ubiquitin ligase for ubiquitination of p53 at a lysine residue K370 (FIG. 14). The Hdm2 activity is significantly up-regulated in many type of cancers. The ACE antibody to the ubiquitin-to-p53 K370 site can be made with KLH-CGGGSSHLK$_{370}$(GG)SK). The assay mixture consists of a biotinylated p53 peptide substrate (biotin-CGGGSSHLKSK), Hdm2, ATP, K48R ubiquitin, E1, and E2 (UbcH5c) (FIG. 14). After incubation, a stop buffer (e.g., 40 mM EDTA) containing detection mix (ULight-streptavidin, and the Europium Cryptate-labeled ubiquitin-to-p53 conjugation site-specific antibody) will be added. The p53 E3 ligase activity will be measured with a time-resolved fluorometer at excitation of 320 nm and emission 665 nm.

This TR-FRET method can be applied for all E3 ligase activity immunoassays with the corresponding conjugation site-specific antibodies.

Similarly, determination of ubiquitin hydrolase activity can typically be performed in a system that contains specific ubiquitin-to-protein/peptide conjugates, and ubiquitin hydrolases (either natural or recombinant), or ubiquitin hydrolase modulators or cofactors. The ubiquitin hydrolase activity can then be measured as the rate of reduction of the ubiquitin-to-protein/peptide conjugates with their corresponding conjugation site-specific ACE antibodies.

In parallel to ubiquitin, there is a growing family of other small posttranslation protein modifiers that conjugate to proteins in similar enzymatic pathways as those of protein ubiquitination, commonly known as either ubiquitin-like molecules (ULMs) or ubiquitin-like proteins (UBLs). UBLs include, but are not limited to: small ubiquitin-like modifier (SUMO), interferon-stimulated gene-15 (ISG15, also known as ubiquitin cross-reactive protein), ubiquitin-related modifier-1 (URM1), neuronal-precursor-cell-expressed developmentally downregulated protein-8 (NEDD8, also called Rub1 in *S. cerevisiae*), human leukocyte antigen F-associated (FAT10), ATG8 or LC3, and ATG12, Fau ubiquitin-like protein (FUB1), MUB (membrane-anchored UBL), ubiquitin fold-modifier-1 (UFM1), and ubiquitin-like protein-5 [UBL5, which is also known as homologous to ubiquitin-1 (Hub1) in *Schizosaccharomyces pombe*].

UBLs share only modest primary sequence identity with ubiquitin, but they have a similar three-dimensional structure. Most UBLs use their C-terminal glycine to conjugate a substrate protein at a lysine (K) residue by an isopeptide bond, with exceptions of yeast ATG8 and ATG12. UBLs conjugate to substrate proteins also via E1 (activating), E2 (conjugating) and E3 (ligating) enzymatic systems, similar to those for protein ubiquitination. UBL-conjugates can also be reversed by UBL-specific hydrolases in a similar fashion as that of deubiquitinating enzymes.

The present invention provides ACE methods, antibodies, reagents, immunoassays and kits for measuring UBL-related enzyme activities including, but not limited to, UBL ligases, UBL hydrolases and their modulators or cofactors. The antibody-based assays can typically be carried out in a system that contains a UBL, the substrate, the E1-, E2- and E3-like conjugation enzyme fraction (either natural or recombinant), an ATP regenerating system, and UBL-related enzyme modulators or cofactors. After the enzymatic reaction, UBL-related enzyme activity as reflected by the rate of formation of the UBL-conjugated ACE structures can be determined with their corresponding conjugation site-specific ACE antibodies.

Similarly, the methods of assays of UBL hydrolase activity can typically be performed in a system that contains a UBL-conjugated substrate, a UBL hydrolase (either natural or recombinant), and UBL hydrolase modulators or cofactors. After the enzymatic reaction, the UBL hydrolase activity as reflected by the rate of reduction of the UBL-conjugated ACE structures, can be determined with their corresponding ACE antibodies.

5. Therapeutic Applications of the Ace Methods, Antibodies and Reagents.

The ACE antibodies of the invention may be useful, for example, in targeting the conjugation sites, for treating macromolecular conjugation- and aggregation-related diseases including, but not limited to neurodegenerative diseases, cancer, vascular diseases, inflammatory diseases, macular degeneration, transplant rejection, multiple sclerosis, stroke, heart diseases, diabetes, infectious diseases and all protein conjugation-related diseases.

The present invention may be relevant to the delivery of ACE antibodies to the target by carriers including, but not limited to, liposomes. This may be done by packing liposomes with conjugation-site-specific antibodies and hydrolytic enzymes including, but not limited to proteases, glycosidases/deglycosylases, lipases or phospholipases, nucleases, or cytotoxic agents such as chemotherapeutic agents, toxins, or radioactive isotopes. Review articles about immunoliposome and immunoliposome-mediated delivery can be found in publications (e.g., Pirollo et al., 2008; Brignole and Marimpietri et al., 2005; Bendas 2001; Maruyama, 2000).

The ACE antigen design of the invention may be used for preparations of vaccines to particular diseases including, but not limited to, neurodegenerative diseases, cancers, conformation diseases (e.g. cystic fibrosis, Celiac diseases, and lysosomal storage diseases), vascular diseases, diabetes-related diseases, and aging-related diseases. The vaccines may be preventive or therapeutic.

6. Bio-Material Applications of the Ace Methoids, Antibodies and Reagents.

Conjugation site-specific or other linear hidden antigen antibodies may be useful in biomaterial applications, such as making collagen-like biomaterials for tissue repair. Cell-binding sequences and enzyme crosslink sites of collagen-like biomaterials are crucial in creating collagen mimics that can reproduce biological activities of natural collagens. Transglutaminase catalyzes formation of fibronectin-like, and hyaluronic acid and glycosaminoglycans-like, as well as collagen-like biomaterials. These biomaterials are components of the tissue extracellular matrices. Conjugation site-specific ACE antibodies of the invention may be useful in determining covalent crosslink sites of biomaterials.

The ACE methods, reagents, antibodies, and immunoassays can be used to measure hydrolytic enzymes or chemical agent activities in industrial applications including, but not limited to cellulases and esterase activities in the paper industry, hydrolytic enzyme activities in the leather, pigment removal, biodegradable plastic, or bioethanol industries, and the like.

7. Kits

In another aspect, the present invention provides kits for detecting the ACEs in biological samples. Such kits comprise ACE antibodies, hydrolytic enzymes or agents, and other items including, but not limited to secondary antibodies, enzyme modulators, cofactors, and buffer systems.

REFERENCES CITED

Patent Documents

| | | |
|---|---|---|
| U.S. Pat. No. 7,491,501 | Feb. 17, 2009 | Wooten et al., (p62 as probe for protein ubiquitination) |
| U.S. Pat. No. 7,223,556 | May 29, 2007 | Zhou et al. (A method for targeting a target polypeptide for ubiquitin-dependent proteolysis) |
| US 20070218069A | Sep. 20, 2007 | Gordon et al. (about Polyubiquitin antibody) |
| US 20070037221 | Feb. 15, 2007 | Block et al. (Lectin-based diagnosis of liver cancer) |
| U.S. Pat. No. 7,022,493 | Apr. 4, 2006 | Issakani et al. (Ubiquitin conjugation assays) |
| U.S. Pat. No. 6,911,335 | Jun. 28, 2005 | Kapeller-Libermann et al. |
| U.S. Pat. No. 6,465,199 | Oct. 15, 2002 | Craig et al. (Compositions and methods for monitoring the modification of natural binding partners. This invention instead encompasses the use of FRET or other detection procedures to monitor the association of polypeptides). |
| U.S. Pat. No. 4,626,507 | Dec. 2, 1986 | Trowbridge et al. (Monoclonal antibody to a glycoprotein, but not specific to the glycosylation site) |
| U.S. Pat. No. 7,460,960 | Mar. 17, 2009 | Lee et al., Proteome epitope tags and methods of use thereof in protein modification analysis |
| WO 02/25287 | Mar. 4, 2003 | Soloviev et al., Detection of Peptide |
| U.S. Pat. No. 5,972,623 | Oct. 14, 1999 | Krane et al., Collagen-peptide assay method |
| U.S. Pat. No. 7,803,553 | Sep. 28, 2010 | Kojima et al., Methods of use of antibodies which recognize a protease cleavage site of an LAP fragment of TGF-β |
| U.S. Pat. No. 6,762,045 | Mar. 20, 2002 | Membrane derived caspase-3, compositions comprising the same and methods of use therefor |

OTHER REFERENCES

Arnold J N, Saldova R, Hamid U M, Rudd P M (2008) Evaluation of the serum N-linked glycome for the diagnosis of cancer and chronic inflammation. Proteomics. 8:3284-3293.

Bendas G (2001) Immunoliposomes: A Promising Approach to Targeting Cancer Therapy. BioDrugs. 15:215-224.

Bian H, Grossman M. Frontotemporal lobar degeneration: recent progress in antemortem diagnosis. Acta Neuropathol. 2007, 114:23-9.

Block T M, Comunale M A, Lowman M, Steel L F, Romano P R, Fimmel C, Tennant B C, London W T, Evans A A, Blumberg B S, Dwek R A, Mattu T S, Mehta A S. Use of targeted glycoproteomics to identify serum glycoproteins that correlate with liver cancer in woodchucks and humans. Proc Natl Acad Sci USA. 2005, 102:779-84.

Breborowicz J, Mackiewicz A, Breborowicz D. Microheterogeneity of alpha-fetoprotein in patient serum as demonstrated by lectin affino-electrophoresis. Scand J Immunol. 1981, 14:15-20.

Brignole C, Marimpietri D, Pagnan G, Di Paolo D, Zancolli M, Pistoia V, Ponzoni M, Pastorino F. Neuroblastoma targeting by c-myb-selective antisense oligonucleotides entrapped in anti-GD2 immunoliposome: immune cell-mediated anti-tumor activities. Cancer Lett. 2005, 228: 181-6.

Bunkenborg J, Pilch B J, Podtelejnikov A V, Wisniewski J R. Screening for N-glycosylated proteins by liquid chromatography mass spectrometry. Proteomics. 2004 4:454-65.

Cao J, Shen C, Wang H, Shen H, Chen Y, Nie A, Yan G, Lu H, Liu Y, Yang P. Identification of N-glycosylation sites on secreted proteins of human hepatocellular carcinoma cells with a complementary proteomics approach. J Proteome Res. 2009, 8:662-72.

Cardoso de Almeida M L, Turner M J. The membrane form of variant surface glycoproteins of Trypanosoma brucei. Nature. 1983, 302:349-52.

Chan C P, Cheung Y C, Renneberg R, Seydack M. New trends in immunoassays. Adv Biochem Eng Biotechnol. 2008, 109:123-54.

Chan M H, Shing M M, Poon T C, Johnson P J, Lam C W (2000) Alpha-fetoprotein variants in a case of pancreatoblastoma. Ann Clin Biochem. 37:681-685.

Clark L G, Maurer P H. Antigenicity of polypeptides (poly-alpha-amino acids). Immunological reactions of sheep antisera to a polymer of glutamic acid, alanine and tyrosine. Int Arch Allergy Appl Immunol. 1969, 35:58-64.

Comunale M A, Lowman M, Long R E, Krakover J, Philip R, Seeholzer S, Evans A A, Hann H W, Block T M, Mehta A S. Proteomic analysis of serum associated fucosylated glycoproteins in the development of primary hepatocellular carcinoma. J Proteome Res. 2006, 5:308-15.

Comunale M A, Wang M, Hafner J, Krakover J, Rodemich L, Kopenhaver B, Long R E, Junaidi O, Bisceglie A M, Block T M, Mehta A S. Identification and development of fucosylated glycoproteins as biomarkers of primary hepatocellular carcinoma. J Proteome Res. 2009, 8:595-602.

Cripps D, Thomas S N, Jeng Y, Yang F, Davies P, Yang A J, Alzheimer disease-specific conformation of hyperphosphorylated paired helical filament-Tau is polyubiquitinated through Lys-48, Lys-11, and Lys-6 ubiquitin conjugation. J Biol Chem. 2008, 281:10825-38.

de Leoz M L, An H J, Kronewitter S, Kim J, Beecroft S, Vinall R, Miyamoto S, de Vere White R, Lam K S, Lebrilla C. Glycomic approach for potential biomarkers on prostate cancer: profiling of N-linked glycans in human sera and pRNS cell lines. Dis Markers. 2008, 25:243-58.

Debruyne E N, Delanghe J R. Diagnosing and monitoring hepatocellular carcinoma with alpha-fetoprotein: new aspects and applications. Clin Chim Acta. 2008, 395:19-26.

Denis N J, Vasilescu J, Lambert J P, Smith J C, Figeys D (2007) Tryptic digestion of ubiquitin standards reveals an improved strategy for identifying ubiquitinated proteins by mass spectrometry. Proteomics. 7:868-874.

Dickson D W. Required techniques and useful molecular markers in the neuropathologic diagnosis of neurodegenerative diseases. Acta Neuropathol. 2005, 109:14-24.

Dohm C P, Kermer P, Bähr M (2008) Aggregopathy in neurodegenerative diseases: mechanisms and therapeutic implication. Neurodegener Dis. 5:321-38.

Durand G, Seta N (2000) Protein glycosylation and diseases: blood and urinary oligosaccharides as markers for diagnosis and therapeutic monitoring. Clin Chem. 46:795-805.

Engelender S. Ubiquitination of alpha-synuclein and autophagy in Parkinson's disease. Autophagy. 2008, 4:372-4.

Ferri N, Paoletti R, Corsini A. Lipid-modified proteins as biomarkers for cardiovascular disease: a review. Biomarkers. 2005, 10:219-37.

Finkbeiner S, Mitra S. The ubiquitin-proteasome pathway in Huntington's disease. ScientificWorldJournal. 2008, 8:421-33.

Fujimuro M, Yokosawa H. Production of antipolyubiquitin monoclonal antibodies and their use for characterization and isolation of polyubiquitinated proteins. Methods Enzymol. 2005; 399:75-86.

Gagné J P, Bonicalzi M E, Gagné P, Ouellet M E, Hendzel M J, Poirier G G. Poly(ADP-ribose) glycohydrolase is a component of the FMRP-associated messenger ribonucleoparticles. Biochem J. 2005, 392:499-509.

Goldfarb V, Trimble R B, De Falco M, Liem H H, Metcalfe S A, Wellner D, Muller-Eberhard U. An avian serum alpha 1-glycoprotein, hemopexin, differing significantly in both amino acid and carbohydrate composition from mammalian (beta-glycoprotein) counterparts. Biochemistry. 1986, 25:6555-62.

Gupta A K, Naregalkar R R, Vaidya V D, Gupta M. Recent advances on surface engineering of magnetic iron oxide nanoparticles and their biomedical applications. Nanomedicine (Lond), 2007, 2:23-39.

Hirabayashi J. Concept, strategy and realization of lectin-based glycan profiling. J Biochem. 2008, 144:139-47.

Hu P, Shi B, Geng F, Zhang C, Wu W, Wu X Z. E-cadherin core fucosylation regulates nuclear beta-catenin accumulation in lung cancer cells. Glycoconj J. 2008, 25:843-850.

Iwatsubo T, Yamaguchi H, Fujimuro M, Yokosawa H, Ihara Y, Trojanowski J Q, Lee V M. Purification and characterization of Lewy bodies from the brains of patients with diffuse Lewy body disease. Am J Pathol. 1996, 148:1517-29.

Jacob A L, Jordan B A, Weinberg R J. Organization of amyloid-beta protein precursor intracellular domain-associated protein-1 in the rat brain. J Comp Neurol. 2010, 518:3221-36.

Jellinger K A. Criteria for the neuropathological diagnosis of dementing disorders: routes out of the swamp? Acta Neuropathol. 2009, 117:101-10.

Kasai T, Tokuda T, Ishigami N, Sasayama H, Foulds P, Mitchell D J, Mann D M, Allsop D, Nakagawa M. Increased TDP-43 protein in cerebrospinal fluid of patients with amyotrophic lateral sclerosis. Acta Neuropathol. 2009, 117:55-62.

Kertesz V, Van Berkel G J. Fully automated liquid extraction-based surface sampling and ionization using a chip-based robotic nanoelectrospray platform. J Mass Spectrom. 2010, 45:252-60.

Kossowska B, Ferens-Sieczkowska M, Gancarz R, Passowicz-Muszyfiska E, Jankowska R. Fucosylation of serum glycoproteins in lung cancer patients. Clin Chem Lab Med. 2005; 43:361-9.

Kudo T, Iqbal K, Ravid R, Swaab D F, Grundke-Iqbal I. Alzheimer disease: correlation of cerebro-spinal fluid and brain ubiquitin levels. Brain Res. 1994, 639:1-7.

Kuhlmann W D, Krischan R. Resin embedment of organs and postembedment localization of antigens by immunoperoxidase methods. Histochemistry. 1981, 72:377-89.

Li C, Simeone D M, Brenner D E, Anderson M A, Shedden K A, Ruffin M T, Lubman D M. Pancreatic cancer serum detection using a lectin/glyco-antibody array method. J Proteome Res. 2009, 8:483-92.

Li Y, Cozzi P J (2007) MUC1 is a promising therapeutic target for prostate cancer therapy. Curr Cancer Drug Targets. 7:259-271

Liang M, Liang Y Y, Wrighton K, Ungermannova D, Wang X P, Brunicardi F C, Liu X, Feng X H, Lin X (2004) Ubiquitination and proteolysis of cancer-derived Smad4 mutants by SCFSkp2. Mol Cell Biol. 24:7524-37.

Lobell R B, Omer C A, Abrams M T, Bhimnathwala H G, Brucker M J, Buser C A, Davide J P, deSolms S J, Dinsmore C J, Ellis-Hutchings M S, Kral A M, Liu D, Lumma W C, Machotka S V, Rands E, Williams T M, Graham S L, Hartman G D, Oliff A I, Heimbrook D C, Kohl N E. Evaluation of farnesyl:protein transferase and geranylgeranyl:protein transferase inhibitor combinations in preclinical models. Cancer Res. 2001, 61:8758-68.

Mai S, Garini Y (2006) The significance of telomeric aggregates in the interphase nuclei of tumor cells. J Cell Biochem. 97:904-915.

Maruyama K. In vivo targeting by liposomes. Biol Pharm Bull. 2000, 23:791-9.

Matsumoto K, Maeda Y, Kato S, Yuki H (1994) Alteration of asparagine-linked glycosylation in serum transferrin of patients with hepatocellular carcinoma. Clin Chim Acta. 224:1-8.

Matsumoto M L, Wertz I E, Kirkpatrick D S, Lill J R, Tan J, Dugger D, Gordon N, Sidhu S S, Fellouse F A, Komuves L, French D M, Ferrando R E, Lam C, Compaan D, Yu C, Bosanac I, Hymowitz S G, Kelley R F, Dixit V M. (2008) Ubiquitin chain editing revealed by polyubiquitin linkage-specific antibodies. Cell. 134:668-78.

Meerwaldt R, van der Vaart M G, van Dam G M, Tio R A, Hillebrands J L, Smit A J, Zeebregts C J (2008) Clinical relevance of advanced glycation endproducts for vascular surgery. Eur J Vasc Endovasc Surg. 36:125-31.

Mehta A, Block T M. Fucosylated glycoproteins as markers of liver disease. Dis Markers. 2008, 25:259-65.

Mehta A S, Long R E, Comunale M A, Wang M, Rodemich L, Krakover J, Philip R, Marrero J A, Dwek R A, Block T M (2008) Increased levels of galactose-deficient anti-Gal immunoglobulin G in the sera of hepatitis C virus-infected individuals with fibrosis and cirrhosis. J Virol. 82:1259-70.

Mehta P D, Thal L, Wisniewski H M, Grundke-Iqbal I, Iqbal K. Paired helical filament antigen in CSF. Lancet. 1985, 2:35.

Meray R K, Lansbury P T Jr. Reversible monoubiquitination regulates the Parkinson disease-associated ubiquitin hydrolase UCH-L1. J Biol Chem. 2007, 282:10567-10575

Miyoshi E, Shinzaki S, Moriwaki K, Matsumoto H (2010) Identification of fucosylated haptoglobin as a novel tumor marker for pancreatic cancer and its possible application for a clinical diagnostic test. Methods Enzymol. 478:153-64.

Moriwaki K, Miyoshi E (2010) Fucosylation and gastrointestinal cancer. World J Hepatol. 2:151-61.

Naitoh A, Aoyagi Y, Asakura H (1999) Highly enhanced fucosylation of serum glycoproteins in patients with hepatocellular carcinoma. J Gastroenterol Hepatol. 14:436-45.

Narisada M, Kawamoto S, Kuwamoto K, Moriwaki K, Nakagawa T, Matsumoto H, Asahi M, Koyama N, Miyoshi E (2008) Identification of an inducible factor secreted by pancreatic cancer cell lines that stimulates the production of fucosylated haptoglobin in hepatoma cells. Biochem Biophys Res Commun. 377:792-796.

O'Leary T J, Fowler C B, Evers D L, Cunningham R E, Mason J T. Commentary: future directions. In: Shi S-R, Taylor C R, editors. Antigen retrieval immunohistochemistry based research and diagnostics. Hoboken (N.J.): John Wiley. 2010, p. 323-331.

Osumi D, Takahashi M, Miyoshi E, Yokoe S, Lee S H, Noda K, Nakamori S, Gu J, Ikeda Y, Kuroki Y, Sengoku K, Ishikawa M, Taniguchi N. Core fucosylation of E-cadherin enhances cell-cell adhesion in human colon carcinoma WiDr cells. Cancer Sci. 2009, 100:888-95.

Otake Y, Fujimoto I, Tanaka F, Nakagawa T, Ikeda T, Menon K K, Hase S, Wada H, Ikenaka K (2001) Isolation and characterization of an N-linked oligosaccharide that is significantly increased in sera from patients with non-small cell lung cancer. J Biochem. 129:537-42.

Parsons R B, Farrant J K, Price G C, Subramaniam D, Austen B M. Regulation of the lipidation of beta-secretase by statins. Biochem Soc Trans. 2007, 35:577-82.

Peng J, Schwartz D, Elias J E, Thoreen C C, Cheng D, Marsischky G, Roelofs J, Finley D and Gygi S P (2003) A proteomics approach to understanding protein ubiquitination. Nat Biotechnol. 21:921-926.

Perry G, Mulvihill P, Fried V A, Smith H T, Grundke-Iqbal I, Iqbal K. Immunochemical properties of ubiquitin conjugates in the paired helical filaments of Alzheimer disease. J Neurochem. 1989, 52:1523-8.

Pirim I (1998) Production of anti-polyubiquitin and anti-ubiquitin carboxyl terminal hydrolase antibodies and immunohistochemically assessment of them on brain sections of Alzheimer's disease and Lewy body disease. Int J Neurosci. 95:33-42.

Pirollo K F, Chang E H. Targeted delivery of small interfering RNA: approaching effective cancer therapies. Cancer Res. 2008, 68:1247-50.

Ressom H W, Varghese R S, Goldman L, An Y, Loffredo C A, Abdel-Hamid M, Kyselova Z, Mechref Y, Novotny M, Drake S K, Goldman R. Analysis of MALDI-TOF mass spectrometry data for discovery of peptide and glycan biomarkers of hepatocellular carcinoma. J Proteome Res. 2008, 7:603-10.

Saffroy R, Pham P, Reffas M, Takka M, Lemoine A, Debuire B (2007) New perspectives and strategy research biomarkers for hepatocellular carcinoma. Clin Chem Lab Med. 45:1169-1179.

Saldova R, Fan Y, Fitzpatrick J M, Watson R W, Rudd P M (2010) Core fucosylation and {alpha}2-3 sialylation in serum N-glycome is significantly increased in prostate cancer comparing to benign prostate hyperplasia. Glycobiology. [Epub ahead of print]

Sato S, Johnson W (2007) Antibody-mediated neutralization and simian immunodeficiency virus models of HIV/AIDS. Curr HIV Res. 5:594-607.

Sekine C, Aoyagi Y, Suzuki Y, Ichida F. The reactivity of alpha-1-antitrypsin with Lens culinaris agglutinin and its usefulness in the diagnosis of neoplastic diseases of the liver. Br J Cancer. 1987, 56:371-5.

Shi S R, Shi Y, Taylor C R. Antigen retrieval immunohistochemistry: review and future prospects in research and diagnosis over two decades. J Histochem Cytochem. 2011, 59:13-32.

Sou Y S, Tanida I, Komatsu M, Ueno T, Kominami E. Phosphatidylserine in addition to phosphatidylethanolamine is an in vitro target of the mammalian Atg8 modifiers, LC3, GABARAP, and GATE-16. J Biol Chem. 2006, 281:3017-24.

Steffan J S, Agrawal N, Pallos J, Rockabrand E, Trotman L C, Slepko N, Illes K, Lukacsovich T, Zhu Y Z, Cattaneo E, Pandolfi P P, Thompson L M, Marsh J L. SUMO modification of Huntingtin and Huntington's disease pathology. Science. 2004, 304:100-4.

Steinacker P, Hendrich C, Sperfeld A D, Jesse S, von Arnim C A, Lehnert S, Pabst A, Uttner I, Tumani H, Lee V M, Trojanowski J Q, Kretzschmar H A, Ludolph A, Neumann M, Otto M. TDP-43 in cerebrospinal fluid of patients with frontotemporal lobar degeneration and amyotrophic lateral sclerosis. Arch Neurol. 2008, 65:1481-7.

Sturla L, Fruscione F, Noda K, Miyoshi E, Taniguchi N, Contini P, Tonetti M. Core fucosylation of N-linked glycans in leukocyte adhesion deficiency/congenital disorder of glycosylation IIc fibroblasts. Glycobiology. 2005, 15:924-34.

Szargel R, Rott R, Engelender S. Synphilin-1 isoforms in Parkinson's disease: regulation by phosphorylation and ubiquitylation. Cell Mol Life Sci. 2008, 65:80-8.

Thornalley P J (2002) Glycation in diabetic neuropathy: characteristics, consequences, causes, and therapeutic options. Int Rev Neurobiol. 50:37-57.

Tong L, Baskaran G, Jones M B, Rhee J K, Yarema K J (2003) Glycosylation changes as markers for the diagnosis and treatment of human disease. Biotechnol Genet Eng Rev. 20:199-244.

Troyer D A, Mubiru J, Leach R J, Naylor S L (2004) Promise and challenge: Markers of prostate cancer detection, diagnosis and prognosis. Dis Markers. 20:117-128

Valmu L, Alfthan H, Hotakainen K, Birken S, Stenman U H. Site-specific glycan analysis of human chorionic gonadotropin beta-subunit from malignancies and pregnancy by liquid chromatography—electrospray mass spectrometry. Glycobiology. 2006, 16:1207-18.

Waelter S, Boeddrich A, Lurz R, Scherzinger E, Lueder G, Lehrach H, Wanker E E. Accumulation of mutant huntingtin fragments in aggresome-like inclusion bodies as a result of insufficient protein degradation. Mol Biol Cell. 2001,12:1393-1407.

Wang H, Matsuzawa A, Brown S A, Zhou J, Guy C S, Tseng P H, Forbes K, Nicholson T P, Sheppard P W, Hacker H, Karin M, Vignali D A. Analysis of nondegradative protein ubiquitylation with a monoclonal antibody specific for lysine-63-linked polyubiquitin. Proc Natl Acad Sci USA. 2008, 105:20197-202.

Wang X, Gu J, Miyoshi E, Honke K, Taniguchi N. Phenotype changes of Fut8 knockout mouse: core fucosylation is crucial for the function of growth factor receptor(s). Methods Enzymol. 2006, 417:11-22.

Ward R (2002) Antibody phage display. Immunology and Cell Biology. 80:316-317,

White K Y, Rodemich L, Nyalwidhe J O, Comunale M A, Clements M A, Lance R S, Schellhammer P F, Mehta A S, Semmes O J, Drake R R. Glycomic characterization of prostate-specific antigen and prostatic acid phosphatase in prostate cancer and benign disease seminal plasma fluids. J Proteome Res. 2009, 8:620-30.

Wu L H, Shi B Z, Zhao Q L, Wu X Z (2010) Fucosylated glycan inhibition of human hepatocellular carcinoma cell migration through binding to chemokine receptors. Glycobiology. 20:215-23.

Xu G, Paige J S and Jaffrey S R (2010) Global analysis of lysine ubiquitination by ubiquitin remnant immunoaffinity profiling. Nat Biotechnol. 28:868-73.

Yamashita K, Koide N, Endo T, Iwaki Y, Kobata A. Altered glycosylation of serum transferrin of patients with hepatocellular carcinoma. J Biol Chem. 1989, 264:2415-23.

Yang W, Sheng H, Warner D S, Paschen W. Transient global cerebral_ischemia induces a massive increase in protein sumoylation. J Cereb Blood Flow Metab. 2008, 28:269-279.

Young L S, Gascon R, Alam S, Bermudez L E. Monoclonal antibodies for treatment of gram-negative infections. Rev Infect Dis. 1989 November-December; 11 Suppl 7:S1564-71.

Zhao J, Patwa T H, Lubman D M, Simeone D M (2008) Protein biomarkers in cancer: natural glycoprotein microarray approaches. Curr Opin Mol Ther. 10:602-610.

---

We claim:

1. A method of detecting a linear hydrolysis-created Artificially Cleaved Epitope (ACE) structure in a biological sample, wherein the linear ACE structure is hidden in its intact or natural form in a polymeric molecule and is poorly accessible to antibodies, comprising steps of:

(i) designing a linear ACE structure of formula L1-L2---Ln, wherein L1-L2---Ln is a linear polymeric biomolecule (e.g., a linear peptide), wherein L1 and Ln are each terminal residues that are artificially created via chemical bond-specific cleavage by at least one hydrolytic enzyme or hydrolytic agent;

(ii) chemically synthesizing the ACE structure described in step (i) and isolating the ACE structure;

(iii) producing an antibody against the isolated ACE structure of step (ii), wherein the antibody specifically recognizes the ACE structure;

(iv) creating the ACE structure in the sample by treating the sample with the same hydrolytic enzyme or hydrolytic agent that is/are being used to create the terminal residues in step (i), thereby exposing the formerly hidden ACE structure in the sample to specific interaction with the antibody; and (v) detecting the ACE structure created in step (iv) with the antibody, wherein the antibody specifically binds to at least one of the artificially created L1 or Ln terminal residues or residue(s) between L1 and Ln.

2. The method of claim 1 wherein the antibody is a polyclonal antibody, a monoclonal antibody, a bi-specific antibody, a recombinant antibody, a humanized antibody, a single chain or domain antibody, an antibody fragment, or an antibody-like molecule.

3. The method of claim 1 wherein the hydrolysis-created ACE is a linear structure selected from the group consisting of a protein segment, a lipid segment, a saccharide segment, a nucleic acid segment, a protein-to-protein conjugation segment, a protein-to-saccharide conjugation segment, a protein-to-phosphatidylethanolamine conjugation segment, a protein-to-ubiquitin conjugation segment, a protein-to-lipid conjugation segment, a protein-to-GPI conjugation segment, a protein-to-UBL conjugation segment, and a protein-to-(ADP-ribose) conjugation segment.

4. The method of claim 1 wherein the hydrolytic enzyme is selected from the group consisting of a protease, a glycosidase, a lipase, a phospholipase, a nuclease, a polyribosyl hydrolase, and their combinations.

5. The method of claim 1 wherein the hydrolytic agent(s) is selected from a substance with chemical bond-specific hydrolysis activity.

6. The hydrolytic agents of claim 5 wherein the hydrolytic agent is selected from the group consisting of BNPS-skatole (3-bromo-3-methyl-2-[(2-nitrophenyl)thio]-3H-indole), CNBr (cyanogen bromide), formic acid, hydroxylamine ($NH_2OH$), iodosobenzoic acid, and NTCB +Ni (2-nitro-5-thiocyanobenzoic acid).

7. The method of claim 1 wherein the sample is in a sample preparation selected from the group consisting of a blot membrane, a tissue section, an isolated organ, an isolated cell, an isolated organelle, isolated tissue, an isolated body fluid, cell culture media, cell lysate, tissue lysate, an isolated fraction, a subcellular fraction, a chromatographic fraction, an immunocomplex, and a centrifuge fraction.

8. The method of claim 1 wherein the step of preparing the ACE structure further comprises treating the synthesized ACE structure with a fixative.

9. The method of claim 8 wherein the fixative is selected from the group consisting of an aldehyde, an alcohol, acetone, and osmium tetroxide.

* * * * *